(12) United States Patent
Belson et al.

(10) Patent No.: US 10,918,332 B2
(45) Date of Patent: Feb. 16, 2021

(54) SYSTEMS AND METHODS FOR MONITORING PHYSICAL THERAPY OF THE KNEE AND OTHER JOINTS

(71) Applicant: ZipLine Medical, Inc., Campbell, CA (US)

(72) Inventors: Amir Belson, Savyon (IL); Keiichiro Ichiryu, Campbell, CA (US); Zachary Kimura, San Jose, CA (US); Mark Shughart, Redwood City, CA (US); Harold Sampson, Sunnyvale, CA (US); Daren Stewart, Belmont, CA (US); Eric Storne, Menlo Park, CA (US); John Tighe, Los Gatos, CA (US)

(73) Assignee: ZipLine Medical, Inc., Campbell, CA (US)

( * ) Notice: Subject to any disclaimer, the term of this patent is extended or adjusted under 35 U.S.C. 154(b) by 0 days.

(21) Appl. No.: 16/387,446

(22) Filed: Apr. 17, 2019

(65) Prior Publication Data
US 2019/0290198 A1    Sep. 26, 2019

Related U.S. Application Data

(63) Continuation of application No. PCT/US2017/059286, filed on Oct. 31, 2017.
(Continued)

(51) Int. Cl.
*G08B 1/08*      (2006.01)
*A61B 5/00*     (2006.01)
(Continued)

(52) U.S. Cl.
CPC ............ *A61B 5/4848* (2013.01); *A41D 1/002* (2013.01); *A61B 5/00* (2013.01); *A61B 5/002* (2013.01);
(Continued)

(58) Field of Classification Search
CPC ....... A61B 5/4848; A61B 5/00; A61B 5/0002; A61B 5/0004; A61B 5/002; A61B 5/1121;
(Continued)

(56) References Cited

U.S. PATENT DOCUMENTS 2,012,755 A    8/1935    De Muth
2,371,978 A    3/1945    Perham
(Continued)

FOREIGN PATENT DOCUMENTS

CN    1126430 A    7/1996
CN    1442119 A    9/2003
(Continued)

OTHER PUBLICATIONS

U.S. Appl. No. 10/159,825, filed Dec. 25, 2018, Amir et al.
(Continued)

*Primary Examiner* — Zhen Y Wu
(74) *Attorney, Agent, or Firm* — Howard & Howard Attorneys PLLC

(57) ABSTRACT

Systems, devices, and methods for post-surgical joint range of motion measurement, activity monitoring, as well as monitoring compliance with post-operative extremity elevation and cooling recommendations are provided. The system comprises sensor(s) to be attached adjacent a joint of the patient, with limb attachment element(s), applications running on a computing device of the patient and medical practitioner, and a cloud-based backend system.

23 Claims, 20 Drawing Sheets

Related U.S. Application Data

(60) Provisional application No. 62/455,986, filed on Feb. 7, 2017, provisional application No. 62/415,155, filed on Oct. 31, 2016.

(51) Int. Cl.

| | | |
|---|---|---|
| *A41D 1/00* | (2018.01) | |
| *A61B 5/11* | (2006.01) | |
| *G06F 3/0481* | (2013.01) | |
| *G06F 3/0484* | (2013.01) | |
| *A41D 13/12* | (2006.01) | |

(52) U.S. Cl.
CPC .......... *A61B 5/0002* (2013.01); *A61B 5/0004* (2013.01); *A61B 5/1121* (2013.01); *A61B 5/4528* (2013.01); *A61B 5/4585* (2013.01); *A61B 5/4878* (2013.01); *G06F 3/0481* (2013.01); *A41D 13/1281* (2013.01); *A61B 2505/09* (2013.01); *G06F 3/0484* (2013.01)

(58) Field of Classification Search
CPC ... A61B 5/4528; A61B 5/4585; A61B 5/4878; A61B 2505/09; A41D 1/002; A41D 13/1281; G06F 3/0481; G06F 3/0484
USPC .................................................. 340/539.12
See application file for complete search history.

(56) References Cited

U.S. PATENT DOCUMENTS

| | | |
|---|---|---|
| 2,747,248 A | 5/1956 | Mercer |
| 3,118,201 A | 1/1964 | Beghetto, Jr. |
| 3,487,836 A | 1/1970 | Benjamin et al. |
| 3,516,409 A | 6/1970 | Robert |
| 3,863,640 A | 2/1975 | Haverstock |
| 3,926,193 A | 12/1975 | Hasson |
| 3,933,158 A | 1/1976 | Haverstock |
| 3,971,384 A | 7/1976 | Hasson |
| 3,972,328 A | 8/1976 | Chen |
| 3,983,878 A | 10/1976 | Kawchitch |
| 4,038,989 A | 8/1977 | Romero-Sierra et al. |
| 4,114,624 A | 9/1978 | Haverstock |
| 4,210,148 A | 7/1980 | Stivala |
| 4,222,383 A | 9/1980 | Schossow |
| 4,224,945 A | 9/1980 | Cohen |
| 4,526,173 A | 7/1985 | Sheehan |
| 4,531,521 A | 7/1985 | Haverstock |
| 4,535,772 A | 8/1985 | Sheehan |
| 4,605,005 A | 8/1986 | Sheehan |
| 4,612,230 A | 9/1986 | Liland et al. |
| 4,676,245 A | 6/1987 | Fukuda |
| 4,780,168 A | 10/1988 | Beisang et al. |
| 4,871,367 A | 10/1989 | Christensen et al. |
| 4,881,546 A | 11/1989 | Kaessmann |
| 4,905,694 A | 3/1990 | Will |
| 4,950,282 A | 8/1990 | Beisang et al. |
| 4,966,605 A | 10/1990 | Thieler |
| 4,976,726 A | 12/1990 | Haverstock |
| 5,176,703 A | 1/1993 | Peterson |
| 5,190,032 A | 3/1993 | Zacoi |
| 5,259,835 A | 11/1993 | Clark et al. |
| 5,306,236 A | 4/1994 | Blumenfeld et al. |
| 5,336,219 A | 8/1994 | Krantz |
| 5,377,695 A | 1/1995 | An Haack |
| 5,514,155 A | 5/1996 | Daneshvar |
| 5,533,519 A | 7/1996 | Radke et al. |
| 5,562,705 A | 10/1996 | Whiteford |
| 5,665,108 A | 9/1997 | Galindo |
| 5,725,507 A | 3/1998 | Petrick |
| 5,788,660 A | 8/1998 | Resnik |
| 5,823,983 A | 10/1998 | Rosofsky et al. |
| 5,843,123 A | 12/1998 | Brazeau |
| 6,007,564 A | 12/1999 | Haverstock |
| 6,033,654 A | 3/2000 | Stedronsky et al. |
| 6,074,965 A | 6/2000 | Bodenschatz et al. |
| 6,126,615 A | 10/2000 | Allen et al. |
| 6,176,868 B1 | 1/2001 | Detour |
| 6,194,629 B1 | 2/2001 | Bernhard |
| 6,629,949 B1 | 10/2003 | Douglas |
| 6,689,100 B2 | 2/2004 | Connelly et al. |
| 6,726,706 B2 | 4/2004 | Dominguez |
| 7,066,182 B1 | 6/2006 | Dunshee |
| 7,361,185 B2 | 4/2008 | O'Malley et al. |
| 7,455,681 B2 | 11/2008 | Wilke et al. |
| 7,641,682 B2 | 1/2010 | Palmaz et al. |
| 7,645,285 B2 | 1/2010 | Cosgrove et al. |
| 7,799,042 B2 | 9/2010 | Williamson, IV et al. |
| 8,246,590 B2 | 8/2012 | Hu et al. |
| 8,592,640 B2 | 11/2013 | Zepeda et al. |
| 8,663,275 B2 | 3/2014 | O'Malley et al. |
| 9,008,784 B2 * | 4/2015 | Chan .................. A61N 1/36031 607/48 |
| 9,050,086 B2 | 6/2015 | Belson et al. |
| 9,089,328 B2 | 7/2015 | Belson et al. |
| 9,179,914 B2 | 11/2015 | Belson et al. |
| 9,248,049 B2 | 2/2016 | Gurtner et al. |
| 9,271,858 B2 | 3/2016 | Ben-Meir et al. |
| 9,474,529 B2 | 10/2016 | Belson et al. |
| 9,554,799 B2 | 1/2017 | Belson et al. |
| 9,554,800 B2 | 1/2017 | Belson et al. |
| 9,561,034 B2 | 2/2017 | Amir et al. |
| 9,642,621 B2 | 5/2017 | Belson et al. |
| 9,642,622 B2 | 5/2017 | Belson et al. |
| 9,735,893 B1 * | 8/2017 | Aleksov ............... H04B 5/0012 |
| 10,123,800 B2 | 11/2018 | Belson et al. |
| 10,123,801 B2 | 11/2018 | Belson et al. |
| 2002/0099315 A1 | 7/2002 | Lebner |
| 2003/0065294 A1 | 4/2003 | Pickup et al. |
| 2003/0108352 A1 | 6/2003 | Hellman |
| 2003/0120198 A1 | 6/2003 | Barkell et al. |
| 2003/0163160 A1 | 8/2003 | O'Malley et al. |
| 2003/0220596 A1 | 11/2003 | Dunshee |
| 2004/0072964 A1 | 4/2004 | Udding et al. |
| 2004/0106904 A1 | 6/2004 | Gonnelli et al. |
| 2004/0204740 A1 | 10/2004 | Weiser |
| 2004/0210176 A1 | 10/2004 | Diana |
| 2004/0260234 A1 | 12/2004 | Srinivasan et al. |
| 2005/0020956 A1 | 1/2005 | Lebner |
| 2005/0020957 A1 | 1/2005 | Lebner |
| 2005/0070956 A1 | 3/2005 | Rousseau |
| 2005/0080453 A1 | 4/2005 | Lebner et al. |
| 2005/0085757 A1 | 4/2005 | Santanello |
| 2005/0153090 A1 | 7/2005 | Marchitto et al. |
| 2005/0234485 A1 | 10/2005 | Seegert et al. |
| 2005/0277959 A1 | 12/2005 | Cosgrove et al. |
| 2005/0284801 A1 | 12/2005 | Tacklind |
| 2006/0030886 A1 | 2/2006 | Clark |
| 2006/0122522 A1 | 6/2006 | Chavan et al. |
| 2006/0200198 A1 | 9/2006 | Riskin et al. |
| 2006/0259033 A1 | 11/2006 | Nesbitt |
| 2007/0026078 A1 | 2/2007 | Almarsson et al. |
| 2007/0038247 A1 | 2/2007 | Lebner et al. |
| 2007/0078366 A1 | 4/2007 | Haggstrom et al. |
| 2007/0088339 A1 | 4/2007 | Luchetti et al. |
| 2007/0106277 A1 | 5/2007 | Hood et al. |
| 2007/0141130 A1 | 6/2007 | Villanueva et al. |
| 2007/0179419 A1 | 8/2007 | Simpson |
| 2007/0185432 A1 | 8/2007 | Etheredge |
| 2007/0260278 A1 | 11/2007 | Wheeler et al. |
| 2008/0033334 A1 | 2/2008 | Gurtner et al. |
| 2008/0081951 A1 | 4/2008 | Frasier et al. |
| 2008/0103550 A1 | 5/2008 | Wenzel et al. |
| 2008/0114396 A1 | 5/2008 | Cory et al. |
| 2008/0147115 A1 | 6/2008 | O'Malley et al. |
| 2008/0161731 A1 * | 7/2008 | Woods ................... A61B 5/112 600/595 |
| 2008/0228219 A1 | 9/2008 | Weiser |
| 2008/0287864 A1 | 11/2008 | Rosenberg |
| 2009/0036922 A1 | 2/2009 | Riskin et al. |
| 2009/0062531 A1 | 3/2009 | Kanda |
| 2009/0099496 A1 | 4/2009 | Heegaard et al. |
| 2009/0149869 A1 | 6/2009 | Lhun |
| 2009/0158131 A1 | 6/2009 | Choi et al. |

(56) References Cited

U.S. PATENT DOCUMENTS

| | | |
|---|---|---|
| 2009/0162531 A1 | 6/2009 | Nesbitt |
| 2009/0177225 A1 | 7/2009 | Nunez et al. |
| 2009/0177227 A1 | 7/2009 | Warren |
| 2009/0264709 A1 | 10/2009 | Blurton et al. |
| 2009/0299255 A1 | 12/2009 | Kazala, Jr. et al. |
| 2009/0299257 A1 | 12/2009 | Long et al. |
| 2009/0299303 A1 | 12/2009 | Seegert |
| 2010/0023074 A1* | 1/2010 | Powers ............... A61N 1/3925 607/5 |
| 2010/0036209 A1 | 2/2010 | Ferren et al. |
| 2010/0100022 A1 | 4/2010 | Greener et al. |
| 2010/0121286 A1 | 5/2010 | Locke et al. |
| 2010/0228287 A1 | 9/2010 | Jeekel et al. |
| 2011/0077667 A1 | 3/2011 | Singhatat et al. |
| 2011/0106026 A1 | 5/2011 | Wu et al. |
| 2011/0118698 A1* | 5/2011 | Eckhoff ............... A61B 5/1126 604/503 |
| 2011/0144470 A1 | 6/2011 | Mazar et al. |
| 2012/0029266 A1 | 2/2012 | Holmes et al. |
| 2012/0095502 A1 | 4/2012 | Bargon et al. |
| 2012/0116485 A1 | 5/2012 | Burgmann |
| 2012/0203273 A1 | 8/2012 | Riskin et al. |
| 2012/0221044 A1 | 8/2012 | Archibald et al. |
| 2012/0226214 A1 | 9/2012 | Gurtner et al. |
| 2012/0232587 A1 | 9/2012 | Burke et al. |
| 2013/0066365 A1 | 3/2013 | Belson et al. |
| 2013/0072969 A1 | 3/2013 | Zhang |
| 2013/0108352 A1 | 5/2013 | Ruiz, Sr. et al. |
| 2013/0178897 A1 | 7/2013 | Wu et al. |
| 2013/0211259 A1* | 8/2013 | Komistek ........... A61B 5/6828 600/440 |
| 2013/0217998 A1* | 8/2013 | Mahfouz ................ A61B 5/11 600/409 |
| 2013/0267928 A1 | 10/2013 | Imran et al. |
| 2013/0281885 A1 | 10/2013 | Rowbottom et al. |
| 2013/0281981 A1 | 10/2013 | Shamir |
| 2013/0282049 A1 | 10/2013 | Peterson et al. |
| 2013/0331757 A1 | 12/2013 | Belson |
| 2014/0074156 A1 | 3/2014 | Belson et al. |
| 2014/0171849 A1 | 6/2014 | Fischell et al. |
| 2014/0222070 A1 | 8/2014 | Belson et al. |
| 2014/0228712 A1 | 8/2014 | Elliott et al. |
| 2014/0278229 A1 | 9/2014 | Hong et al. |
| 2014/0316323 A1 | 10/2014 | Kanevsky et al. |
| 2015/0045700 A1* | 2/2015 | Cavanagh ........... A61B 5/4528 600/595 |
| 2015/0105423 A1 | 4/2015 | Haudenschild et al. |
| 2015/0148653 A1 | 5/2015 | Fleig et al. |
| 2015/0209563 A1 | 7/2015 | Amir |
| 2015/0216527 A1 | 8/2015 | Belson et al. |
| 2015/0309535 A1 | 10/2015 | Connor et al. |
| 2015/0313593 A1 | 11/2015 | Patenaude et al. |
| 2015/0332004 A1* | 11/2015 | Najafi ................ G16H 50/20 706/46 |
| 2015/0351690 A1 | 12/2015 | Toth et al. |
| 2016/0007909 A1* | 1/2016 | Singh .................. A61B 5/4585 606/102 |
| 2016/0015319 A1* | 1/2016 | Billi ..................... A61B 5/1122 600/301 |
| 2016/0095597 A1 | 4/2016 | Belson et al. |
| 2016/0106931 A1 | 4/2016 | Belson et al. |
| 2016/0114146 A1 | 4/2016 | Belson et al. |
| 2016/0202755 A1 | 7/2016 | Connor |
| 2016/0206311 A1 | 7/2016 | Belson et al. |
| 2016/0206312 A1 | 7/2016 | Belson et al. |
| 2016/0206313 A1 | 7/2016 | Belson et al. |
| 2016/0213924 A1* | 7/2016 | Coleman ............ A61N 1/0452 |
| 2016/0220175 A1* | 8/2016 | Tam .................... A61B 5/1127 |
| 2016/0220252 A1 | 8/2016 | Belson et al. |
| 2016/0242646 A1* | 8/2016 | Obma .................... A61B 5/01 |
| 2016/0249924 A1 | 9/2016 | Belson et al. |
| 2016/0262685 A1* | 9/2016 | Wagner ............... A61B 5/1123 |
| 2016/0296149 A1 | 10/2016 | Polsky et al. |
| 2016/0302721 A1* | 10/2016 | Wiedenhoefer ...... A61B 5/0013 |
| 2016/0310140 A1 | 10/2016 | Belson et al. |
| 2016/0338621 A1* | 11/2016 | Kanchan ............... A61B 5/002 |
| 2016/0338644 A1* | 11/2016 | Connor ............... A61B 5/1071 |
| 2017/0000386 A1* | 1/2017 | Salamatian ........... G06Q 50/22 |
| 2017/0042541 A1 | 2/2017 | Belson et al. |
| 2017/0055896 A1* | 3/2017 | Al-Ali ................. A61B 5/0408 |
| 2017/0143341 A1 | 5/2017 | Belson et al. |
| 2017/0156664 A1 | 6/2017 | Belson et al. |
| 2017/0188875 A1* | 7/2017 | Banet .................. A61B 5/6826 |
| 2017/0196507 A1* | 7/2017 | Singh ..................... A61B 5/112 |
| 2017/0265800 A1* | 9/2017 | Auchinleck .......... A61B 5/6828 |
| 2017/0281074 A1* | 10/2017 | D'Lima ................... A61B 5/11 |
| 2017/0367644 A1* | 12/2017 | Sharman ............... A61B 5/1118 |
| 2018/0160966 A1* | 6/2018 | Inan ....................... A61B 7/006 |
| 2018/0279919 A1* | 10/2018 | Bansbach ............. A61B 5/1121 |
| 2019/0060128 A1 | 2/2019 | Belson |

FOREIGN PATENT DOCUMENTS

| | | |
|---|---|---|
| CN | 1524507 A | 9/2004 |
| CN | 101938944 A | 1/2011 |
| CN | 202537562 U | 11/2012 |
| CN | 102946812 A | 2/2013 |
| CN | 104755033 A | 7/2015 |
| CN | 104825200 A | 8/2015 |
| EP | 1600108 A2 | 11/2005 |
| GB | 1401877 A | 8/1975 |
| JP | S5223497 | 6/1977 |
| JP | S62243557 A | 10/1987 |
| JP | H07502913 A | 3/1995 |
| JP | 2001149485 A | 6/2001 |
| JP | 2005512678 A | 5/2005 |
| JP | 2005532134 A | 10/2005 |
| JP | 2010504835 A | 2/2010 |
| JP | 2013515417 A | 5/2013 |
| JP | 2013538603 A | 10/2013 |
| WO | WO-8401805 A1 | 5/1984 |
| WO | WO-9629013 A1 | 9/1996 |
| WO | WO-03053296 A1 | 7/2003 |
| WO | WO-2006124671 A2 | 11/2006 |
| WO | WO-2007004603 A1 | 1/2007 |
| WO | WO-2007044647 A2 | 4/2007 |
| WO | WO-2008019051 A2 | 2/2008 |
| WO | WO-2008060532 A2 | 5/2008 |
| WO | WO-2009066116 A1 | 5/2009 |
| WO | WO-2011043786 A1 | 4/2011 |
| WO | WO-2011139912 A1 | 11/2011 |
| WO | WO-2011159623 A1 | 12/2011 |
| WO | WO-2013067024 A1 | 5/2013 |
| WO | WO-2014066879 A2 | 5/2014 |
| WO | WO-2014070922 A1 | 5/2014 |
| WO | WO-2015012887 A1 | 1/2015 |
| WO | WO-2015103556 A1 | 7/2015 |
| WO | WO-2015168165 A1 | 11/2015 |
| WO | WO-2017027075 A1 | 2/2017 |
| WO | WO-2017044120 A1 | 3/2017 |
| WO | WO-2017181059 A1 | 10/2017 |
| WO | WO-2017184825 A1 | 10/2017 |
| WO | WO-2018081795 | 5/2018 |

OTHER PUBLICATIONS

Ann; Davis et al., "Effect of Surgical Incision Closure Device on Skin Perfusion Following Total Ankle Arthroplasty", UFHealth, 2017, Poster.

Bauback; Safa et al., "In Vivo Efficacy Study Showing Comparative Advantage of Bacterial Infection Prevention with Zip-type Skin Closure Device vs. Subcuticular Sutures", Cureus, Aug. 4, 2018, 3102, 1-11.

Cody; C. Wyles et al., "Running Subcuticular Closure Enables the Most Robust Perfusion After TKA: A Randomized Clinical Trial", Clinical Orthopaedics and Related Research, Springer, Mar. 3, 2015, 1-10.

"Dictionary.com definition of "fixed", Available at http://www.dictionary.com/browse/fixed, accessed on Sep. 13, 2017".

European search report and opinion dated Jan. 7, 2014 for EP Application No. 11778067.6.

(56) References Cited

OTHER PUBLICATIONS

European search report and opinion dated Jan. 7, 2014 for EP Application No. 11796253.0.
"European search report and opinion dated Feb. 17, 2017 for EP Application No. 140829202."
"European search report and opinion dated Apr. 29, 2015 for EP Application No. 10822334.8."
European search report and opinion dated Jul. 12, 2016 for EP Application No. 13851258.
"European search report and written opinion dated Aug. 12, 2015 for EP Application No. 12844746.3."
European search report with written opinion dated Jul. 12, 2016 for EP13851258.
"Extended European search report and opinion dated Jul. 27, 2017 for EP Application No. 15733186".
"International search report and written opinion dated Jan. 12, 2016 for PCT Application No. US2015/049671."
International search report and written opinion dated Feb. 6, 2014 for PCT/US2013/067563.
International search report and written opinion dated Mar. 19, 2013 for PCT/US2012/062820.
"International search report and written opinion dated Apr. 29, 2015 for PCT/US2015/010188."
International search report and written opinion dated Jul. 29, 2011 for PCT/US2011/034649.
International search report and written opinion dated Jul. 30, 2010 for PCT/US2010/000430.
International search report and written opinion dated Aug. 30, 2016 for PCT/US2016/028297.
International search report and written opinion dated Sep. 10, 2014 for PCT/US2014/016587.
"International search report and written opinion dated Sep. 30, 2015 for PCT Application No. US2015/28066."
International search report and written opinion dated Oct. 21, 2011 for PCT Application No. US11/40213.
International search report with written opinion dated Jul. 14, 2017 for PCT/US2017/027695.
International search report with written opinion dated Jul. 18, 2017 for PCT/US2017/028537.
International search report with written opinion dated Aug. 30, 2016 for PCT/US2016/028297.
"K984204, 510(k) Premarket Notification Summary, Silverlon™ Direct Pressure Wound Closure Strip, May 19, 2007."
Kemal; Levi et al., "Mechanics of Wound Closure: Emerging Tape-Based Wound Closure Technology vs. Traditional Methods", Cureus, Oct. 12, 2016, 827, 1-5.
"Merriam-webster definition of "integral", accessed on Sep. 13, 2017, https://www.merriam-webster.com/dictionary/integral".
Merriam-Webster Dictionary. Definition of "lateral". http://www.merriam-webster.com/dictionary/lateral. Accessed on May 5, 2016.
Notice of allowance dated Jan. 17, 2013 for U.S. Appl. No. 13/096,602.
Notice of allowance dated Feb. 10, 2015 for U.S. Appl. No. 14/180,524.
Notice of allowance dated Feb. 21, 2017 for U.S. Appl. No. 14/625,366.
Notice of allowance dated Feb. 23, 2016 for U.S. Appl. No. 15/081,595.
"Notice of Allowance dated Jun. 15, 2018 for U.S. Appl. No. 13/665,160."
"Notice of Allowance dated Jun. 20, 2018 for U.S. Appl. No. 15/130,764."
Notice of allowance dated Jun. 21, 2016 for U.S. Appl. No. 15/081,526.
Notice of allowance dated Sep. 17, 2012 for U.S. Appl. No. 13/286,378.
Notice of allowance dated Sep. 20, 2012 for U.S. Appl. No. 13/286,757.
"Notice of allowance dated Sep. 22, 2015 for U.S. Appl. No. 13/414,176."
Notice of allowance dated Sep. 30, 2016 for U.S. Appl. No. 15/130,149.
Notice of allowance dated Oct. 5, 2016 for U.S. Appl. No. 15/096,083.
Notice of allowance dated Oct. 14, 2016 for U.S. Appl. No. 15/081,550.
Notice of allowance dated Dec. 19, 2014 for U.S. Appl. No. 14/180,564.
Notice of allowance dated Dec. 19, 2016 for U.S. Appl. No. 15/130,149.
"Notice of Allowance dated Aug. 9, 2018 for U.S. Appl. No. 14/851,059."
Office action dated Feb. 1, 2017 for U.S. Appl. No. 15/130,764.
"Office action dated Feb. 14, 2019 for U.S. Appl. No. 15/201,088".
"Office action dated Feb. 25, 2019 for U.S. Appl. No. 15369293."
Office action dated Feb. 26, 2015 for U.S. Appl. No. 13/414,176.
Office action dated Mar. 4, 2016 for U.S. Appl. No. 13/874,046.
Office action dated Mar. 21, 2014 for U.S. Appl. No. 13/414,176.
"Office action dated Mar. 26, 2019 for U.S. Appl. No. 16/132,736".
"Office action dated Apr. 7, 2015 for U.S. Appl. No. 13/685,909."
Office action dated May 2, 2012 for U.S. Appl. No. 13/096,602.
Office action dated May 3, 2016 for U.S. Appl. No. 13/665,160.
Office action dated May 11, 2016 for U.S. Appl. No. 15/081,595.
Office action dated May 12, 2016 for U.S. Appl. No. 15/081,550.
Office action dated May 26, 2016 for U.S. Appl. No. 15/081,526.
Office action dated May 31, 2016 for U.S. Appl. No. 15/096,083.
"Office action dated Jun. 1, 2017 for U.S. Appl. No. 15/442,382."
"Office action dated Jun. 2, 2017 for U.S. Appl. No. 13/665,160."
"Office action dated Jun. 5, 2015 for U.S. Appl. No. 13/874,046."
"Office action dated Jun. 6, 2018 for U.S. Appl. No. 15/201,088."
Office action dated Jun. 17, 2014 for U.S. Appl. No. 13/414,176.
Office action dated Jun. 17, 2016 for U.S. Appl. No. 15/130,149.
Office action dated Jul. 20, 2016 for U.S. Appl. No. 15/130,764.
"Office action dated Jul. 27, 2017 for U.S. Appl. No. 14/851,059".
Office action dated Aug. 18, 2014 for U.S. Appl. No. 14/180,564.
"Office action dated Aug. 24, 2017 for U.S. Appl. No. 14/958,803".
Office action dated Sep. 19, 2014 for U.S. Appl. No. 13/685,909.
"Office Action dated Sep. 22, 2017 for U.S. Appl. No. 13/665,160".
"Office Action dated Sep. 26, 2017 for U.S. Appl. No. 13/685,909".
"Office Action dated Oct. 5, 2017 for U.S. Appl. No. 14/958,818".
"Office action dated Oct. 14, 2015 for U.S. Appl. No. 13/685,909."
"Office action dated Oct. 23, 2015 for U.S. Appl. No. 13/665,160."
"Office action dated Nov. 2, 2018 for U.S. Appl. No. 15/442,382."
Office action dated Nov. 17, 2016 for U.S. Appl. No. 15/081,595.
Office action dated Nov. 19, 2012 for U.S. Appl. No. 13/096,602.
"Office Action dated Nov. 22, 2017 for U.S. Appl. No. 15/130,764".
"Office Action dated Nov. 28, 2017 for U.S. Appl. No. 15/442,382".
Office action dated Dec. 1, 2016 for U.S. Appl. No. 13/665,160.
Office action dated Dec. 29, 2014 for U.S. Appl. No. 13/685,909.
"PCT/US2017/059286 International Search Report and Written Opinion dated Mar. 6, 2018".
Thakral; et al., "Electrical stimulation to accelerate wound healing", CoAction, 2013, 4:22061, 1-9.
"U.S. Appl. No. 14/958,803, Notice of Allowance dated Apr. 4, 2018".
U.S. Appl. No. 14/958,803, Notice of Allowance dated May 11, 2018.
"U.S. Appl. No. 14/851,059, Notice of Allowance dated Mar. 14, 2018".
Zip® Surgical Skin Closure. Fast, non-invasive alternative to staples, sutures and glue. Accessed Aug. 17, 2016. http://www.ziplinemedical.com/products/zip-surgical-skin-closure/.

\* cited by examiner

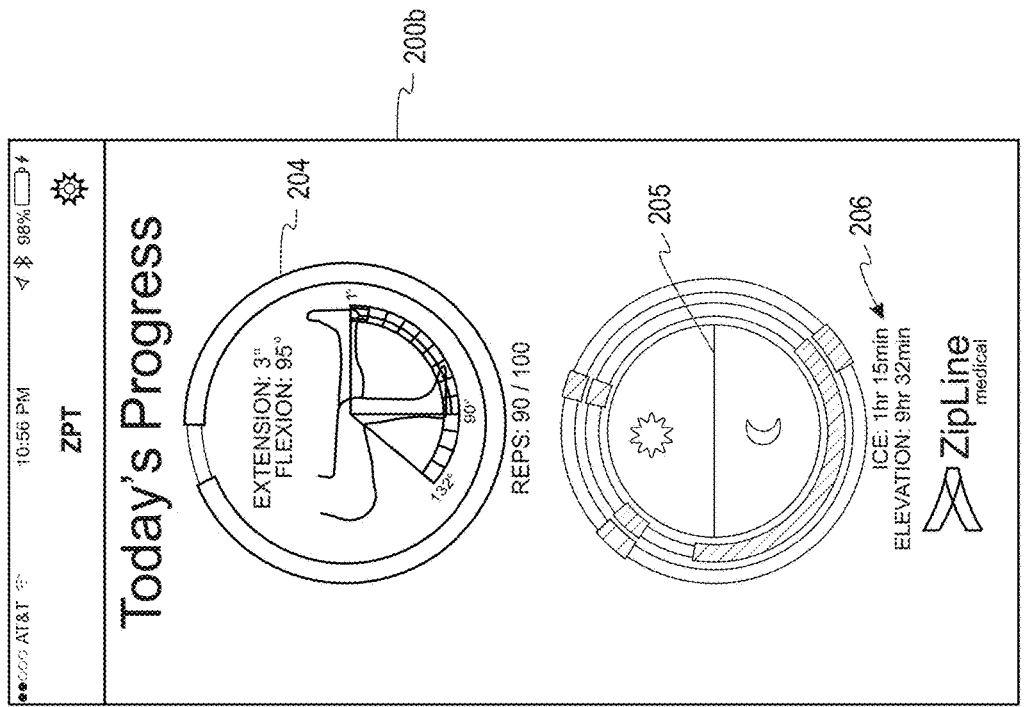
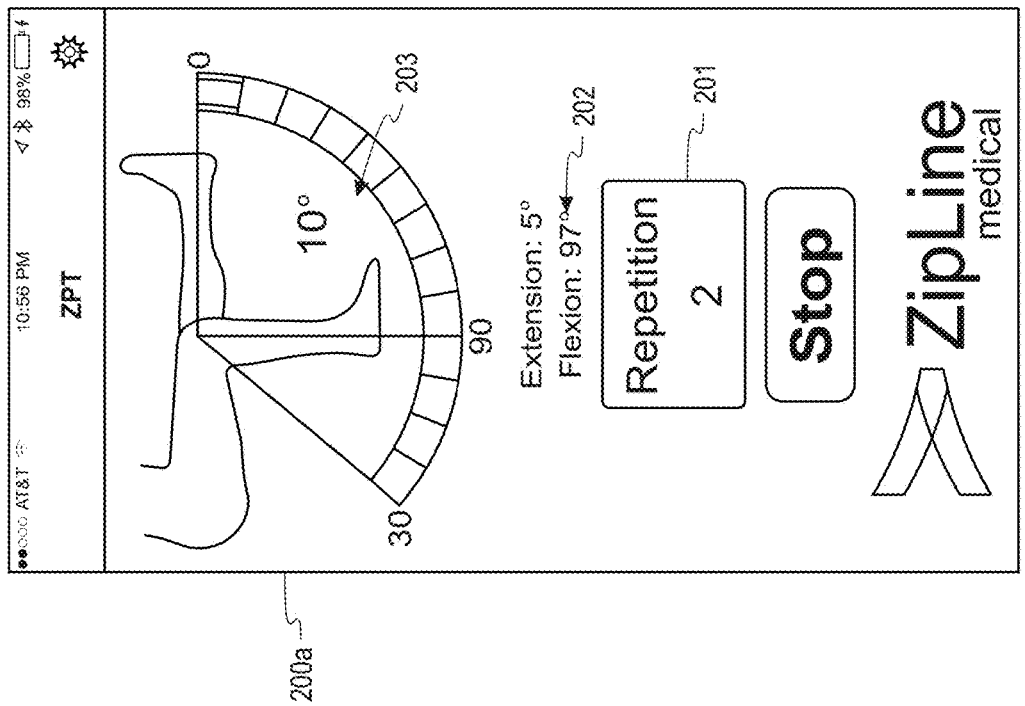
Fig. 2A
Fig. 2B

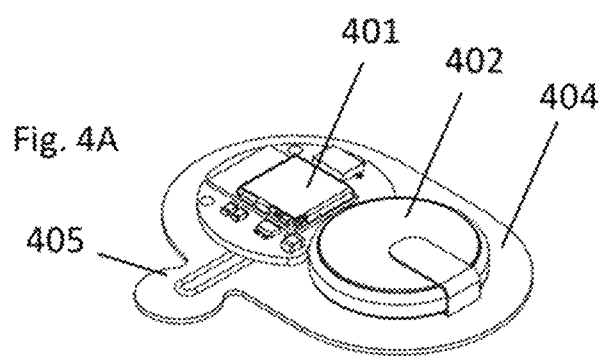
Fig. 4A
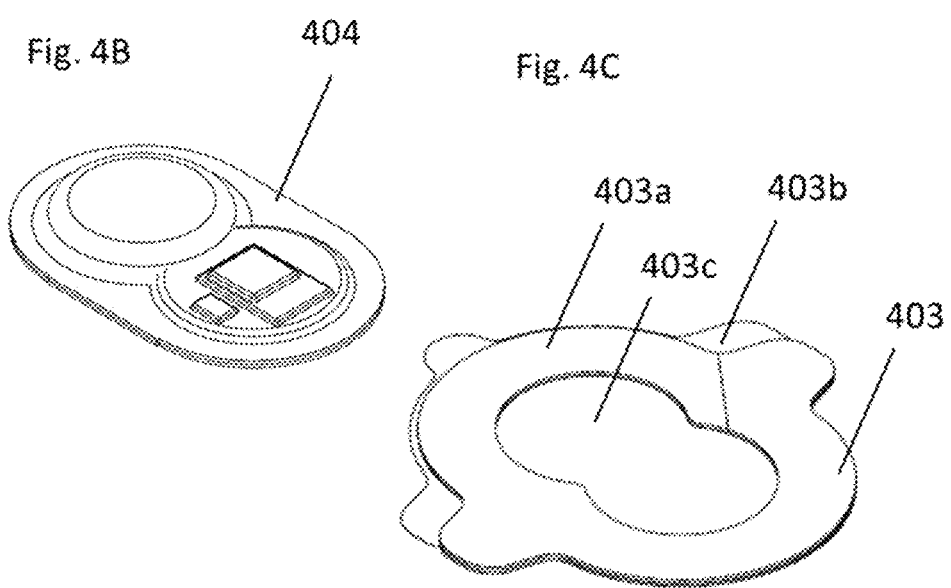
Fig. 4B
Fig. 4C

Fig. 5A
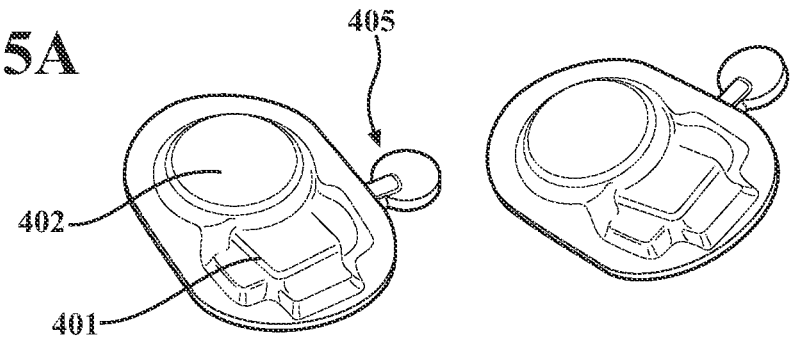
Fig. 5B
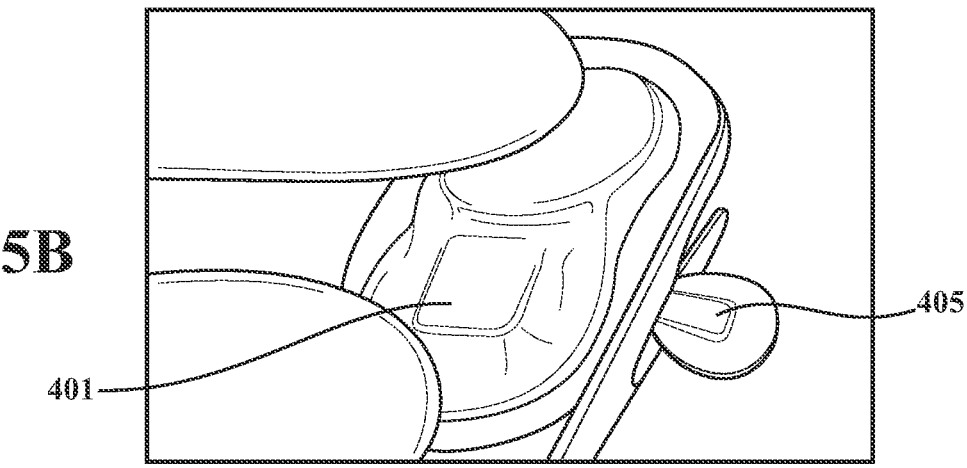
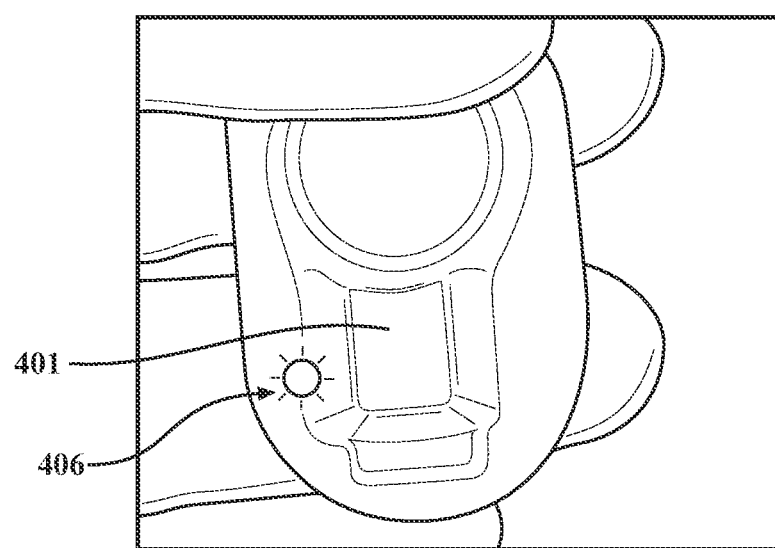
Fig. 5C

Fig. 7A
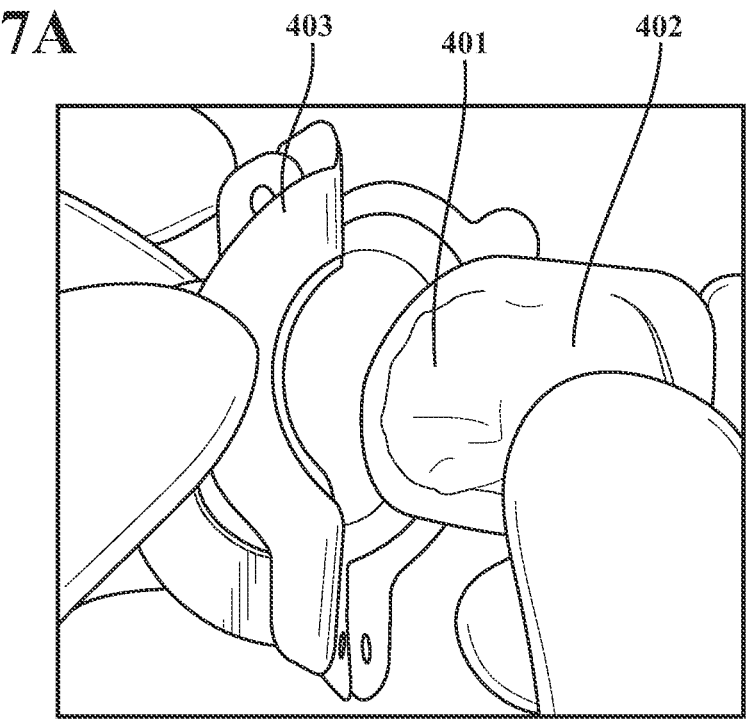
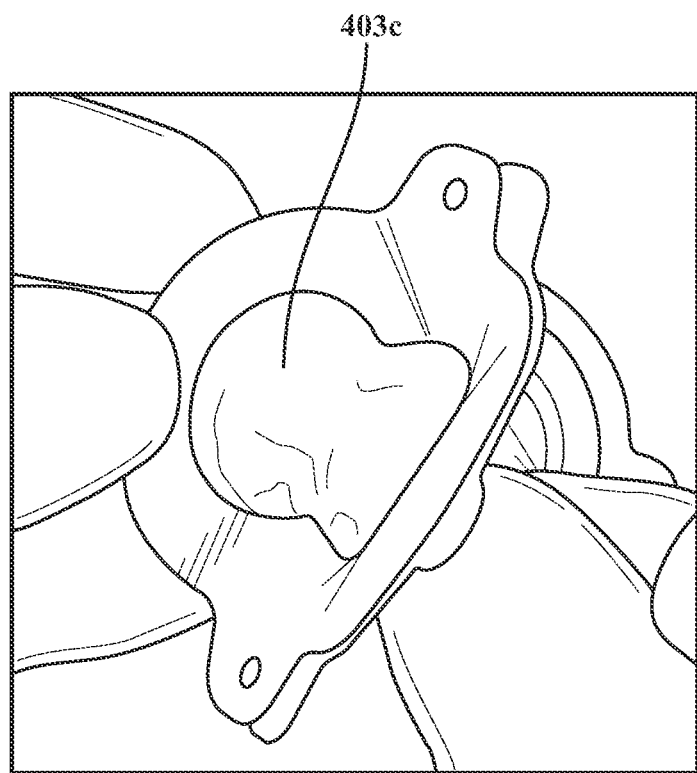
Fig. 7B

Fig. 7C
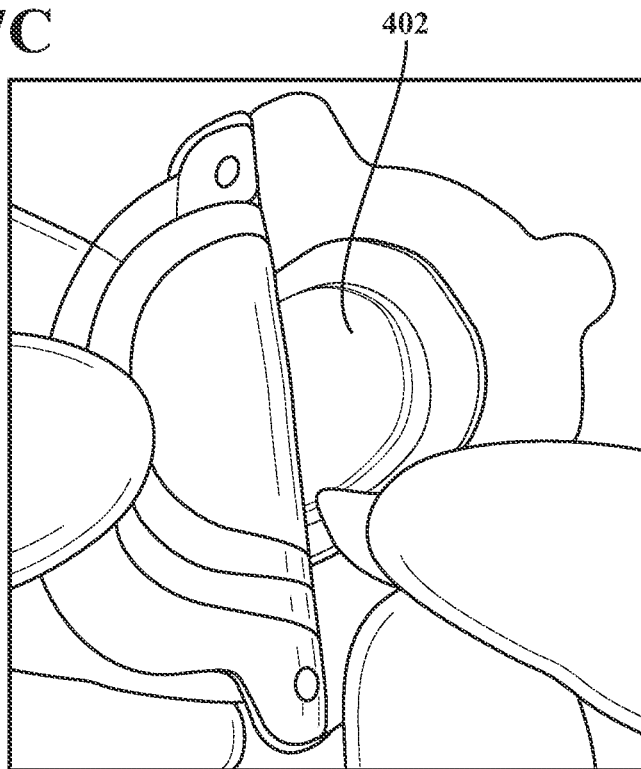
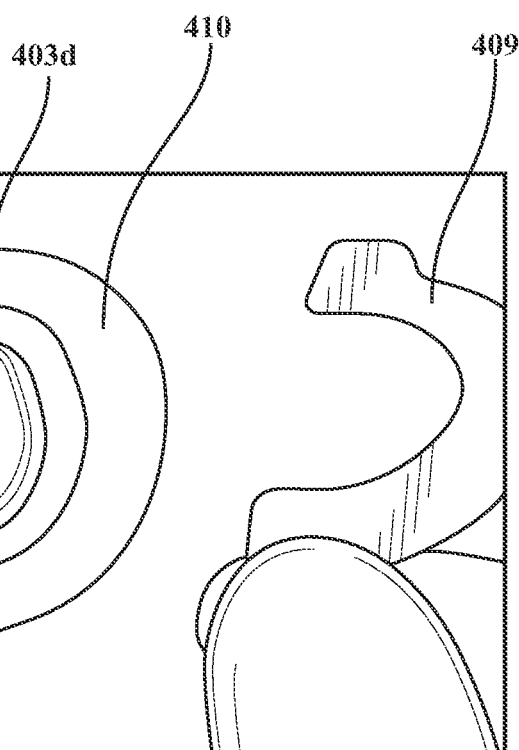
Fig. 7D

Fig. 8A
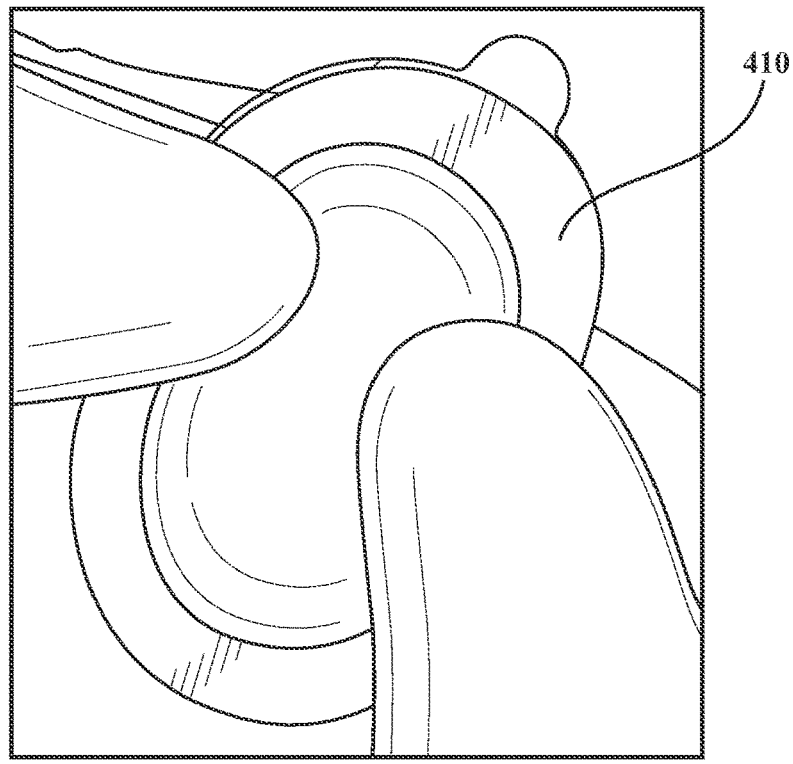
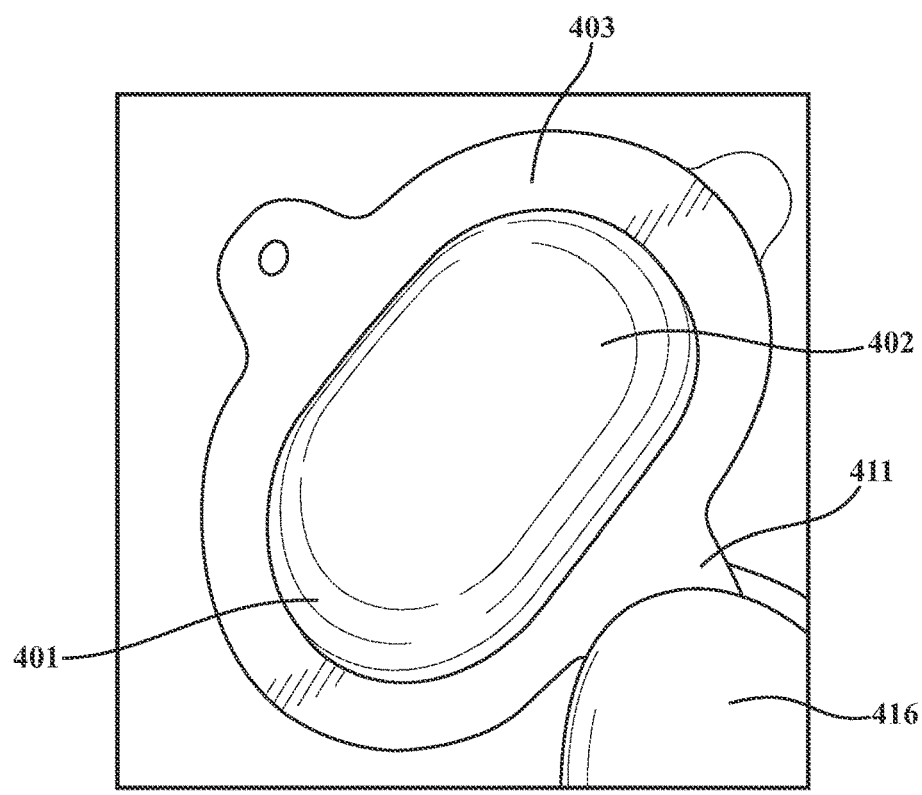
Fig. 8B

Fig. 9C
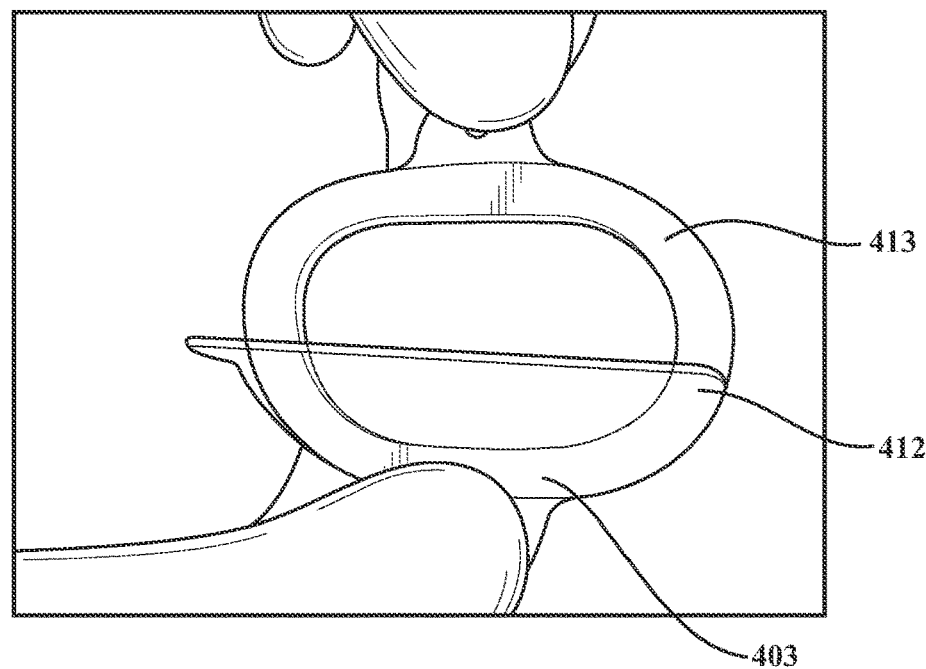
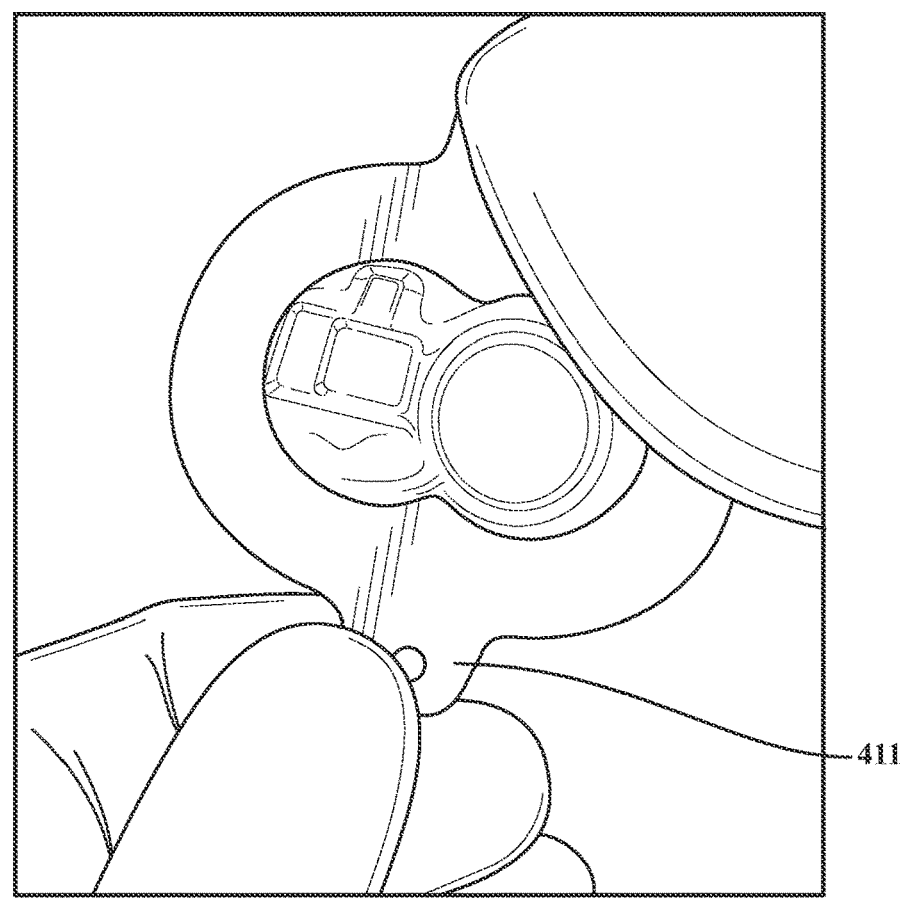
Fig. 9D

Fig. 9E
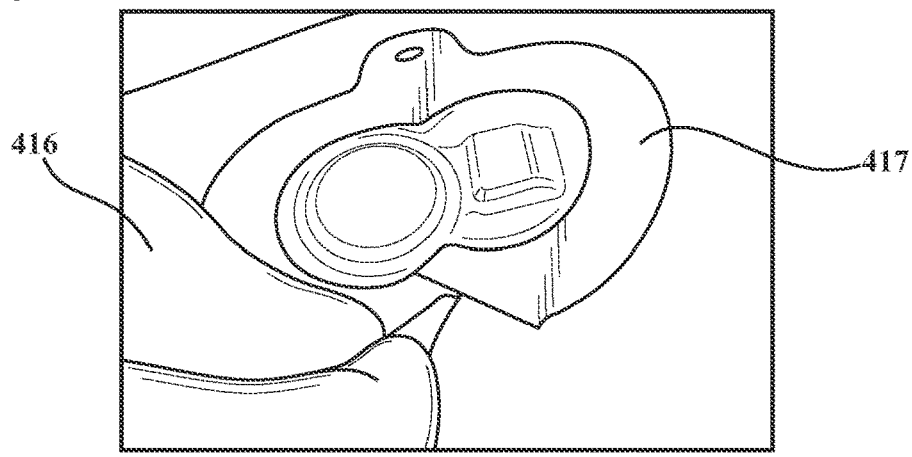
Fig. 9F
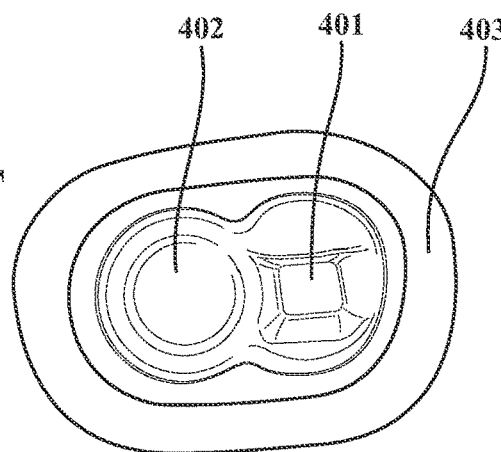
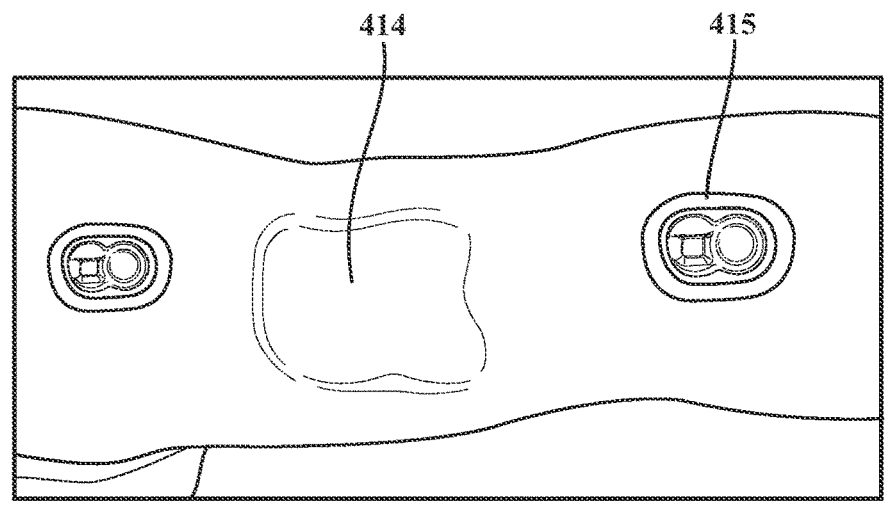
Fig. 9G

SYSTEMS AND METHODS FOR MONITORING PHYSICAL THERAPY OF THE KNEE AND OTHER JOINTS

CROSS-REFERENCE

This application is a continuation of PCT Application No. PCT/US2017/059286, filed Oct. 31, 2017, which claims the benefit of U.S. Provisional Application Nos. 62/455,986, filed Feb. 7, 2017, and 62/415,155, filed Oct. 31, 2016, which are incorporated herein by reference in their entirety.

BACKGROUND

Outcomes of joint surgeries (e.g., total hip arthroplasty, ACL repair, rotator cuff repair, etc.) vary and results depend on patient compliance with prescribed physiotherapies. Non-compliance with the prescribed therapies may be attributed to: (i) uncertainty or lack of clarity about how much or how little to perform an exercise (i.e., how much should the joint flex or extend), (ii) lack of supervision or reminders to perform an exercise (e.g., ice and elevate joint every two hours), (iii) lack of feedback or information on the patients progress (e.g., the joint is moving 5° more this week compared to last week), and (iv) lack of visibility by the clinician of the patients progress (i.e., clinician may only see the patient 3 weeks post-surgery), among other things.

There are therefore needs for improved systems, devices, and methods to monitor and encourage patient compliance with prescribed physical therapies.

References of interest may include the following: U.S. Pat. Nos. 9,008,784 and 9,271,858; and, U.S. Publication Nos. 20150045700, 20160007909, 20160202755, 20160213924, 2016022015, 20160242646, 20160302721, and 20160310140.

SUMMARY

This patent application describes systems, devices, and methods for post-surgical joint range of motion measurement, activity monitoring, as well as monitoring compliance with post-operative extremity elevation and cooling recommendations.

An exemplary device may measure and monitor joint position, motion, activity, swelling, and temperature, among other parameters, providing feedback for both patients and medical practitioners to facilitate patient compliance and improved outcomes.

An exemplary system may comprise (i) sensor(s) to be attached to a joint of the patient, (ii) applications running on a computing device of the patient and medical practitioner, such as a personal computer, laptop computer, smart speaker, smart home hub, smartphone, tablet, or wearable computer, and (iii) a cloud-based backend system to connect to the applications.

In one aspect, disclosed herein are systems for monitoring a joint of a subject, the system comprising: a plurality of adherent sensors for adhering to skin adjacent the joint, each adherent sensor comprising an adherent surface, a mechanical sensing element for sensing one or more mechanical parameters of the joint, and a transmitter; a local computing device in communication with at least one adherent sensor of the plurality of adherent sensors to receive measurement data from the at least one adherent sensor; and a remote computing device in communication with the local computing device to receive the measurement data and provide analysis of the measurement data to the local computing device, the local computing device providing the analysis to the subject. In some embodiments, at least one adherent sensor of the plurality of adherent sensors comprises a replaceable enclosure and a sensor assembly removable from the enclosure, the replaceable enclosure comprising the adherent surface and the sensor assembly comprising the mechanical sensing element and the transmitter. In some embodiments, the sensor assembly further comprises a power source comprising one or more of a power supply, a battery, a capacitor, or an energy harvesting element. In some embodiments, the at least one adherent sensor of the plurality of adherent sensors comprises an activation element coupled to the power source and the at least one adherent sensor is activated by at least partially removing the activation element. In some embodiments, the at least one adherent sensor of the plurality of adherent sensors is configured to be worn by the subject for at least six to eight weeks and the replaceable enclosure is configured to be replaced after one to two weeks of use while the sensor assembly is continually used after replacement of the replaceable enclosure. In some embodiments, the mechanical sensing element comprises one or more of a strain sensor, a force sensor, a flex sensor, a pressure sensor, an accelerometer, a magnetometer, a gyroscope, a potentiometer, a barometer, a piezoelectric sensor, a pressurized tube sensor, a coiled conductor sensor, a magnetic sensor. In some embodiments, the mechanical sensing element is configured to measure one or more of an elevation of the adherent sensor, a pitch, roll, or yaw of the adherent sensor, an orientation of the adherent sensor relative to gravity, an orientation of the adherent sensor relative to a paired adherent sensor, an orientation of the adherent sensor relative to the joint, motion of the adherent sensor, motion of the joint, motion of tissue adjacent the joint, a deformation of the adherent sensor, stress on the adherent sensor, or strain on the adherent sensor. In some embodiments, the at least one adherent sensor of the plurality of adherent sensors further comprises one or more of a temperature sensor, a humidity sensor, an electrical impedance sensor, an acoustic impedance sensor, an electromyography (EMG) sensor, an oxygen sensor, a pH sensor, an optical sensor, an ultrasound sensor, a glucose sensor, or a biomarker sensor. In some embodiments, the measurement data comprises one or more of an elevation of the at least one adherent sensor, a pitch, roll, or yaw of the at least one adherent sensor, an elevation of the at least one adherent sensor relative to a paired adherent sensor of the plurality of adherent sensors, a temperature of the skin adjacent the joint, motion of the at least one adherent sensor, motion of the at least one adherent sensor relative to the paired adherent sensor, an orientation of the at least one adherent sensor, an orientation of the at least one adherent sensor relative to the paired adherent sensor, an orientation of the at least one adherent sensor relative to the joint, a stretching or shrinkage of the at least one adherent sensor, an oxygenation of tissue adjacent the joint, a humidity of the tissue adjacent the joint, a muscle activity of the joint, an electrical impedance of the tissue adjacent the joint, an acoustic impedance of the tissue adjacent the joint, or one or more biomarkers. In some embodiments, the local computing device comprises one or more of a personal computer, a laptop computer, a tablet computer, a smart phone, a smart TV, a gaming console, a digital media player, a smart speaker, a smart home, a smart watch, a VR/AR goggle or glasses, or a wearable computing device. In some embodiments, the remote computing device comprises one or more of a server, a workstation, a personal computer, a laptop computer, a tablet computer, a smart phone, a smart TV, a gaming console, a digital media player, a smart speaker, a smart home, a smart watch, a VR/AR goggle or glasses, or a wearable computing device. In some embodiments, the plurality of adherent sensors are configured to communicate with one another wirelessly. In some embodiments, the plurality of adherent sensors are configured to communicate with one another wirelessly with a wireless data transfer protocol comprising one or more of Near Field Communication (NFC), wireless USB, ultra-wide-band, ultraband, Wi-Fi, Bluetooth, Bluetooth LE, ZigBee, WiMax, Thread, LoRa, LPWA, an IoT networking protocol, a radio-wave based protocol, a microwave based protocol, an infrared based protocol, or a sound-wave based protocol. In some embodiments, wherein the plurality of adherent sensors are configured to communicate with the local computing device wirelessly. In some embodiments, the plurality of adherent sensors are configured to communicate with one another wirelessly with a wireless data transfer protocol comprising one or more of Near Field Communication (NFC), wireless USB, ultra-wide-band, ultraband, Wi-Fi, Bluetooth, Bluetooth LE, ZigBee, WiMax, Thread, LoRa, LPWA, an IoT networking protocol, a radio-wave based protocol, a microwave based protocol, an infrared based protocol, or a sound-wave based protocol. In some embodiments, one or more of the local computing device or the remote computing device is configured to determine one or more of a range of motion of the joint, a range of flexion of the joint, a range of extension of the joint, a range of rotation of the joint, a motion pattern of the joint, a gait of the subject, a position of the joint, an orientation of the joint, a placement of the plurality of adherent sensors relative to the joint, a compliance of the subject to a joint cooling or heating protocol, a compliance of the subject to a movement protocol, a compliance of the subject for muscle activation/inactivation, swelling of the joint, inflammation of the joint, edema of the joint, impact on the joint, or a physical therapy progress of the subject based on the received measurement data. In some embodiments, one or more of the local computing device or the remote computing device is configured to determine placements and orientations of the plurality of adherent sensors relative to the joint adjacent response and determine one or more of a range of motion of the joint, a range of flexion of the joint, a range of extension of the joint, a range of rotation of the joint, a motion pattern of the joint, a gait of the subject, a position of the joint, or an orientation of the joint based on the determined placement and orientations of the plurality of adherent sensors relative to the joint. In some embodiments, the analysis of the measurement data is automatically generated by the remote computing device. In some embodiments, the systems disclosed herein further comprises a medical professional computing device in communication with the remote computing device to access one or more of the measurement data or at least a first portion of the analysis, and wherein at least a second portion of the analysis of the measurement data is provided by the medical professional through the medical professional computing device. In some embodiments, the medical professional computing device comprises one or more of a personal computer, a laptop computer, a tablet computer, a smart phone, a smart TV, a gaming console, a digital media player, a smart speaker, a smart home, a smart watch, or a wearable computing device. In some embodiments, the local computing device is configured to provide the analysis to the subject via one or more of an audio user interface or a video user interface of the local computing device. In some embodiments, the local computing device is configured to further provide one or more of a reminder, an alarm, a tip, an insight, or an instruction to the subject. In some embodiments, the local computing device is configured to further receive input from the subject and transmit the received input to the remote computing device. In some embodiments, the input comprises one or more of a self-diagnosis parameter, a progress of a physical therapy protocol, a compliance to a physical therapy protocol, or a biometric parameter of the subject. In some embodiments, the joint comprises one or more of an ankle, a knee, a hip, a spine, a neck, a shoulder, an elbow, or a wrist.

In another aspect, disclosed herein are methods for monitoring a joint of a subject over a course of therapy, the method comprising: providing a plurality of adherent sensors adhered to skin adjacent the joint, each adherent sensor comprising an adherent surface, a mechanical sensing element for sensing one or more mechanical parameters of the joint, and a transmitter; measuring measurement data with at least one adherent sensor of the plurality of adherent sensors; transmitting the measurement data from the at least one adherent sensor to a local computing device, the local computing device being in communication with a remote computing device and being configured to transmit the measurement data thereto; receiving the measurement data with the remote computing device; providing analysis of the measurement data to the local computing device from the remote computing device; and providing the analysis to the subject with the local computing device. In some embodiments, at least one adherent sensor of the plurality of adherent sensors comprises a replaceable enclosure and a sensor assembly removable from the enclosure, the replaceable enclosure comprising the adherent surface and the sensor assembly comprising the mechanical sensing element and the transmitter, and wherein the replaceable enclosure is replaced while the sensor assembly is continually used over the course of therapy. In some embodiments, the sensor assembly further comprises a power source comprising one or more of a power supply, a battery, a capacitor, or an energy harvesting element. In some embodiments, the at least one adherent sensor of the plurality of adherent sensors comprises an activation element coupled to the power source and the at least one adherent sensor is activated by at least partially removing the activation element. In some embodiments, the at least one adherent sensor of the plurality of adherent sensors is configured to be worn by the subject for at least six to eight weeks and the replaceable enclosure is configured to be replaced after one to two weeks of use while the sensor assembly is continually used after replacement of the replaceable enclosure. In some embodiments, the mechanical sensing element comprises one or more of a strain sensor, a force sensor, a flex sensor, a pressure sensor, an accelerometer, a magnetometer, a gyroscope, a potentiometer, a barometer, a piezoelectric sensor—a pressurized tube sensor, a coiled conductor sensor, a magnetic sensor. In some embodiments, measuring the measurement data comprises measuring one or more of an elevation of the adherent sensor, an orientation of the adherent sensor relative to gravity, an orientation of the adherent sensor relative to a paired adherent sensor, an orientation of the adherent sensor relative to the joint, motion of the adherent sensor, motion of the joint, motion of tissue adjacent the joint, a deformation of the adherent sensor, a pitch of the adherent sensor, a roll of the adherent sensor, a yaw of the adherent sensor, stress on the adherent sensor, or strain on the adherent sensor with the mechanical sensing element of the at least one adherent sensor. In some embodiments, the at least one adherent sensor of the plurality of adherent sensors further comprises one or more of a temperature sensor, a humidity sensor, an electrical impedance sensor, an acoustic impedance sensor, an electromyography (EMG) sensor, an oxygen sensor, a pH sensor, an optical sensor, an ultrasound sensor, a glucose sensor, or a biomarker sensor. In some embodiments, measuring the measurement data comprises measuring one or more of an elevation of the at least one adherent sensor, an elevation of the at least one adherent sensor relative to a paired adherent sensor of the plurality of adherent sensors, a temperature of the skin adjacent the joint, motion of the at least one adherent sensor, a pitch of the at least one adherent sensor, a roll of the at least one adherent sensor, a yaw of the at least one adherent sensor, motion of the at least one adherent sensor relative to the paired adherent sensor, an orientation of the at least one adherent sensor, an orientation of the at least one adherent sensor relative to the paired adherent sensor, an orientation of the at least one adherent sensor relative to the joint, a stretching or shrinkage of the at least one adherent sensor, an oxygenation of tissue adjacent the joint, a humidity of the tissue adjacent the joint, a muscle activity of the joint, an electrical impedance of the tissue adjacent the joint, an acoustic impedance of the tissue adjacent the joint, or one or more biomarkers.

In some embodiments, the local computing device comprises one or more of a personal computer, a laptop computer, a tablet computer, a smart phone, a smart TV, a gaming console, a digital media player, a smart speaker, a smart home, a smart watch, a VR/AR goggle or glasses, or a wearable computing device. In some embodiments, the remote computing device comprises one or more of a server, a workstation, a personal computer, a laptop computer, a tablet computer, a smart phone, a smart TV, a gaming console, a digital media player, a smart speaker, a smart home, a smart watch, a VR/AR goggle or glasses, or a wearable computing device. In some embodiments, the plurality of adherent sensors are configured to communicate with one another wirelessly. In some embodiments, the plurality of adherent sensors are configured to communicate with one another wirelessly with a wireless data transfer protocol comprising one or more of Near Field Communication (NFC), wireless USB, ultra-wide-band, ultraband, Wi-Fi, Bluetooth, Bluetooth LE, ZigBee, WiMax, Thread, LoRa, LPWA, an IoT networking protocol, a radio-wave based protocol, a microwave based protocol, an infrared based protocol, or a sound-wave based protocol. In some embodiments, the plurality of adherent sensors is configured to communicate with the local computing device wirelessly. In some embodiments, the plurality of adherent sensors are configured to communicate with one another wirelessly with a wireless data transfer protocol comprising one or more of Near Field Communication (NFC), wireless USB, ultra-wide-band, ultraband, Wi-Fi, Bluetooth, Bluetooth LE, ZigBee, WiMax, Thread, LoRa, LPWA, an IoT networking protocol, a radio-wave based protocol, a microwave based protocol, an infrared based protocol, or a sound-wave based protocol. In some embodiments, the systems disclosed herein further comprises determining one or more of a range of motion of the joint, a range of flexion of the joint, a range of extension of the joint, a range of rotation of the joint, a motion pattern of the joint, a gait of the subject, a position of the joint, an orientation of the joint, a placement of the plurality of adherent sensors relative to the joint, a compliance of the subject to a joint cooling or heating protocol, a compliance of the subject to a movement protocol, a compliance of the subject for muscle activation/inactivation swelling of the joint, inflammation of the joint, edema of the joint, impact on the joint, or a physical therapy progress of the subject based on the received measurement data with one or more of the local computing device or the remote computing device. In some embodiments, the systems disclosed herein further comprises determining one or more of placements and orientations of the plurality of adherent sensors relative to the joint adjacent response and determine one or more of a range of motion of the joint, a range of flexion of the joint, a range of extension of the joint, a range of rotation of the joint, a motion pattern of the joint, a gait of the subject, a position of the joint, or an orientation of the joint based on the determined placement and orientations of the plurality of adherent sensors relative to the joint with one or more of the local computing device or the remote computing device. In some embodiments, the systems disclosed herein further comprise automatically generating the analysis of the measurement data with the remote computing device. In some embodiments, providing analysis of the measurement data to the local computing device from the remote computing device comprises providing a medical professional computing device access to the remote computing device to access one or more of the measurement data or at least a first portion of the analysis, receiving at least a second portion of the analysis from the medical professional computing device as provided by the medical professional with the remote computing device, compiling at least the first and second portions of the analysis, and transmitting the compiled analysis to the local computing device.

In some embodiments, the medical professional computing device comprises one or more of a personal computer, a laptop computer, a tablet computer, a smart phone, a smart TV, a gaming console, a digital media player, a smart speaker, a smart home, a smart watch, or a wearable computing device. In some embodiments, the local computing device provides the analysis to the subject via one or more of an audio user interface or a video user interface of the local computing device. In some embodiments, the systems disclosed herein further comprise providing one or more of a reminder, an alarm, a tip, an insight, or an instruction to the subject with the local computing device. In some embodiments, the systems disclosed herein further comprise receiving input from the subject with the local computing device and transmitting the received input to the remote computing device with the local computing device. In some embodiments, the input comprises one or more of a self-diagnosis parameter, a progress of a physical therapy protocol, a compliance to a physical therapy protocol, or a biometric parameter of the subject. In some embodiments, the joint comprises one or more of an ankle, a knee, a hip, a spine, a neck, a shoulder, an elbow, or a wrist.

In another aspect, disclosed herein are methods for monitoring a joint of a subject over a course of therapy, the method comprising: activating a first and second adherent sensors, each adherent sensor comprising a replaceable enclosure and a sensor assembly removable from the replaceable enclosure; pairing one or more of the first or second adherent sensors to one another or to a local computing device; adhering the first and second adherent sensors to skin adjacent the joint; and receiving measurement data from one or more of the first or second adherent sensors adhered to the skin adjacent the joint, the measurement data being measured by the sensor assembly of one or more of the first or second adherent sensors. In some embodiments, the sensor assembly of each adherent sensor comprises one or more of a power supply, battery, or energy harvesting element. In some embodiments, each adherent sensor comprises an activation element coupled to the power supply, battery, or energy harvesting element and the at least one adherent sensor is activated by at least partially removing the activation element. In some embodiments, the first and second adherent sensors are coupled to the joint to measure measurement data for at least six to eight weeks. In some embodiments, the methods disclosed herein further comprises, after one to two weeks of use, removing the sensor assembly of the first or second adherent sensor from their respective replaceable enclosure, enclosing the removed sensor assembly with a new replaceable enclosure, and re-adhering the first or second adherent sensor onto the skin adjacent the joint. In some embodiments, the methods disclosed herein further comprises repeatedly replacing the replaceable enclosure of the first or second adherent sensor every one to two weeks of use. In some embodiments, pairing the one or more of the first or second adherent sensors to one another or to the local computing device comprises pairing the first and second adherent sensors to one another in a master-slave relationship. In some embodiments, pairing the one or more of the first or second adherent sensors to one another or to the local computing device comprises pairing each of the first and second adherent sensors individually to the local computing device. In some embodiments, the local computing device is a computing device of the subject or a medical professional. In some embodiments, the first and second adherent sensors are configured to communicate with one another wirelessly. In some embodiments, the first and second adherent sensors are configured to communicate with the local computing device wirelessly. In some embodiments, the first and second adherent sensors are adhered to the skin adjacent the joint in an operating room. In some embodiments, the first and second adherent sensors are adhered to the skin adjacent the joint in an operating room before, during, or after a surgical operation is performed on the joint. In some embodiments, the measurement data is received by one or more of a local computing device of the subject, a remote computing device, or a local computing device of a medical professional. In some embodiments, the methods disclosed herein further comprise providing an analysis of the measurement data to the subject. In some embodiments, the joint comprises one or more of an ankle, a knee, a hip, a spine, a neck, a shoulder, an elbow, or a wrist. In some embodiments, the joint comprises a knee, and wherein adhering the first and second adherent sensors to the skin adjacent the joint comprises adhering the first sensor to skin over or adjacent quadriceps of the subject and adhering the second sensor over or adjacent the shin of the subject.

In yet another aspect, disclosed herein are methods for monitoring a joint of a subject, the method comprising: providing first and second adherent sensors adhered to skin adjacent the joint; measuring motion of the first and second adherent sensors adhered to the skin adjacent the joint; identifying one or more cycles of flexion and extension of the joint from the measured motion; identifying one or more impacts on the joint from the measured motion; determining a gait pattern of the subject based on the identified one or more cycles of flexion and extension and the identified one or more impacts on the joint, the gait pattern indicated by a coincidence of the one or more cycles of flexion and extension with the one or more impacts on the joint. In some embodiments, the methods disclosed herein further comprise monitoring the gait pattern for one or more gait inconsistencies. In some embodiments, determining the gait pattern comprises distinguishing walking of the subject from a free movement of the joint of the subject. In some embodiments, the joint comprises one or more of a hip, a knee, or an ankle of the subject. In some embodiments, the motion of the first and second adherent sensors is measured with one or more of a strain sensor, a force sensor, a flex sensor, a pressure sensor, an accelerometer, a magnetometer, a gyroscope, a potentiometer, a barometer, a piezoelectric sensor, a pressurized tube sensor, a coiled conductor sensor, and a magnetic sensor, of the first or second adherent sensors.

In yet another aspect, disclosed herein are methods for monitoring a joint of a subject, the method comprising: providing first and second adherent sensors adhered to skin adjacent the joint; measuring a mechanical parameter of the joint with one or more of the first or second adherent sensors; and determining an elevation, a pitch, roll, yaw, or a combination thereof of the joint based on the measured mechanical parameter. In some embodiments, determining the elevation of the joint comprises detecting and comparing relative positions of the first and second sensors. In some embodiments, one or more of the first or second sensors comprise one or more magnetometers. In some embodiments, one or more of the first or second sensors comprise one or more barometers. In some embodiments, the methods disclosed herein further comprises determining if the subject is standing, sitting, lying down in a prone position, or lying down in a supine position based on the determined elevation, pitch, roll, yaw, or the combination thereof. In some embodiments, determining the elevation of the joint comprises tracking the elevation of the joint over a time period to establish a baseline elevation of the joint and identifying deviations from the baseline elevation. In some embodiments, determining the subject's compliance with a therapeutic protocol based on the identified deviations from the baseline elevation.

In yet another aspect, disclosed herein are methods for monitoring a joint of a subject, the method comprising: providing first and second adherent sensors adhered to skin adjacent the joint; measuring a mechanical parameter of the joint with one or more of the first or second adherent sensors; measuring a temperature of the skin adjacent the joint with one or more of the first or second adherent sensors; and determining an inflammatory response or an edema of the joint based on the measured mechanical parameter and the measured temperature of the skin. In some embodiments, measuring the mechanical parameter of the joint comprises measuring a stretching or contraction of the one or more of the first or second adherent sensors. In some embodiments, the stretching or contraction of the one or more of the first or second adherent sensors is in a direction transverse to a direction of flexion and extension of the joint. In some embodiments, determining the inflammatory response comprises identifying a coincidence of stretching of the first or second adherent sensors with an increase in measured temperature. In some embodiments, determining an inflammatory response or an edema of the joint further comprises one or more of measuring a change in inductance of a conductive ink trace on one or more of the first or second adherent sensors, measuring an acoustic impedance of tissue adjacent the joint with one or more of the first or second adherent sensors, measuring oxygen saturation of the tissue adjacent the joint with one or more of the first or second adherent sensors, measuring a change in wireless signal strength with one or more of the first or second adherent sensors, or measuring electrical impedance of tissue adjacent the joint with one or more of the first or second adherent sensors.

In yet another aspect, disclosed herein are methods for monitoring a joint of a subject, the method comprising: providing first and second adherent sensors adhered to skin adjacent the joint; measuring a mechanical parameter of the joint with one or more of the first or second adherent sensors; determining an inflammatory response or an edema of the joint based on the measured mechanical parameter. In some embodiments, measuring the mechanical parameter of the joint comprises measuring a stretching or contraction of the one or more of the first or second adherent sensors. In some embodiments, the stretching or contraction of the one or more of the first or second adherent sensors is in a direction transverse to a direction of flexion and extension of the joint. In some embodiments, determining an inflammatory response or an edema of the joint further comprises one or more of measuring a change in inductance of a conductive ink trace on one or more of the first or second adherent sensors, measuring an acoustic impedance of tissue adjacent the joint with one or more of the first or second adherent sensors, measuring oxygen saturation of the tissue adjacent the joint with one or more of the first or second adherent sensors, measuring a change in wireless signal strength with one or more of the first or second adherent sensors, or measuring electrical impedance of tissue adjacent the joint with one or more of the first or second adherent sensors.

In still yet another aspect, disclosed herein are methods for monitoring a knee of a subject, the method comprising: providing a first adherent sensor adhered near a shin of the subject; providing a second adherent sensor adhered near quadriceps of the subject; determining an orientation of the first adherent sensor adhered near the shin relative to a direction of flexion and extension of the knee; determining an orientation of the second sensor adhered near the quadriceps relative to the direction of flexion and extension of the knee; measuring movement of the first and second adherent sensors; and determining one or more of a range of motion, a magnitude of motion, or a direction of movement of the knee based on the measured movement of the first and second adherent sensors and the determined orientations of the first and second sensors relative to the direction and extension of the knee.

In still yet another aspect, disclosed herein are systems for monitoring a joint of a subject, the system comprising: a computing device for the subject, the computing device comprising a user interface and a digital processing device configured to: receive measurement data from one or more sensors coupled to the joint, store the received measurement data, receive input from the subject through the user interface, transmit the received measurement data and received input to a remote computing device, receive one or more of an analysis of the transmitted measurement data and received input or a treatment regimen from the remote computing device, and provide one or more of the received analysis or treatment regimen to the subject through the user interface. In some embodiments, the digital processing device is further configured to authenticate the one or more sensors prior to coupling to the one or more sensors to receive the measurement data. In some embodiments, the digital processing device is further configured to authenticate the subject through the user interface prior to receiving the input from the subject. In some embodiments, the digital processing device is further configured to set a sampling interval for receiving the measurement data from the one or more sensors. In some embodiments, the digital processing device is further configured to set a transmission interval for transmitting the measurement data to the remote computing device. In some embodiments, the digital processing device is configured to provide the one or more of the received analysis or the treatment regimen by providing one or more of an alarm, a notification, a reminder, a goal, or a communication interface with a medical professional to the subject. In some embodiments, the digital processing device is further configured to generate a real-time analysis of the received measurement data. In some embodiments, the digital processing device is configured to transmit the real-time analysis to one or more of the remote computing device or a computing device of a medical professional. In some embodiments, the digital processing device is configured to display the real-time analysis to the subject through the user interface. In some embodiments, the real-time analysis comprises one or more of a range of motion of the joint, a temperature of the joint, or an elevation of the joint. In some embodiments, the input from the subject comprises one or more of a recorded event, a progression in a therapeutic protocol, or feedback on the therapeutic protocol from the subject.

In still yet another aspect, disclosed herein are systems for monitoring a joint of a subject, the system comprising: a computing device for a medical professional monitoring the subject, the computing device comprising a user interface and a digital processing device configured to: provide measurement data of the subject to the medical professional through the user interface, the measurement data being received from a remote computing device and originating from one or more sensors coupled to the joint to measure the measurement data and transmit the measurement data to the remote computing device, providing input from the subject to the medical professional through the user interface, the input being received from a local computing device of the subject, receiving an analysis of one or more of the measurement data or subject input from the medical professional through the user interface, receiving a treatment regimen from the medical professional through the user interface, and transmitting one or more of the received analysis or received treatment regimen to the remote computing device, the remote computing device transmitting the one or more of the received analysis or received treatment regimen to the local computing device of the subject. In some embodiments, the user interface comprises a two-way communication interface between the medical professional and the subject. In some embodiments, the measurement data is provided to the medical professional in real-time. In some embodiments, the digital processing device is further configured to authenticate the medical professional through the user interface prior to receiving the input from the subject. In some embodiments, the digital processing device is further configured to set a sampling interval for receiving the measurement data from the one or more sensors. In some embodiments, the digital processing device is further configured to set a transmission interval for the local computing device of the subject to transmit the measurement data. In some embodiments, one or more of the analysis of the one or more of the measurement data or the subject input or treatment regimen is generated by the medical professional based at least partially on an automated analysis of one or more of the measurement data or the subject input. In some embodiments, the automated analysis is generated by the digital processing device. In some embodiments, the automated analysis is generated by the remote computing device and provided therefrom. In some embodiments, the digital processing device is further configured to generate a real-time analysis of the received measurement data. In some embodiments, the digital processing device is configured to display the real-time analysis to the medical professional through the user interface. In some embodiments, the real-time analysis comprises one or more of a range of motion of the joint, a temperature of the joint, or an elevation of the joint.

In some embodiments, the digital processing device is further configured to generate a progress report for the subject and the user interface is configured to display the progress report to the medical professional.

In still yet another aspect, disclosed herein are systems for monitoring a joint of a subject, the system comprising: a remote computing device in communication with local computing devices for both the subject and a medical professional monitoring the subject, the remote computing device comprising a digital processing device configured to: receive measurement data from the local computing device of the subject, the measurement data originating from one or more sensors coupled to the joint to measure the measurement data and transmit the measurement data to the local computing device, receive input from the subject from the local computing device of the subject, store one or more of the received measurement data or received input in a database, generate an analysis of one or more of the received measurement data or received input from the subject, generate a treatment regimen based on one or more of the received measurement data or received input from the subject, and transmit one or more of the generated analysis or generated treatment regimen to one or more of the local computing device of the subject or the local computing device of the medical professional. In some embodiments, the remote computing device is configured to provide to one or more of the subject or the medical professional access thereto through a user interface. In some embodiments, the user interface comprises a web portal. In some embodiments, the digital processing device is configured authenticate the one or more of the subject or the medical professional prior to providing the access. In some embodiments, the digital processing device is configured to generate the treatment regimen by selecting select the treatment regimen from a plurality of treatment regimens stored in a database based on one or more of the received measurement data or received input. In some embodiments, the digital processing device is configured to generate one or more of the analysis or the treatment regimen by transmitting one or more of the measurement data or the input from the subject to the medical professional and receiving an input from the medical professional in response. In some embodiments, one or more of the analysis of the one or more of the measurement data or the subject input or treatment regimen is generated by the medical professional based at least partially on an automated analysis of one or more of the measurement data or the subject input. In some embodiments, the automated analysis is generated by the digital processing device. In some embodiments, the digital processing device is configured to provide an intermediary for two-way communication between the medical professional and the subject. In some embodiments, the digital processing device is further configured to set a sampling interval for receiving the measurement data from the one or more sensors. In some embodiments, the digital processing device is further configured to set a transmission interval for the local computing device of the subject to transmit the measurement data.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the present disclosure are set forth with particularity in the appended claims. A better understanding of the features and advantages of the present disclosure will be obtained by reference to the following detailed description that sets forth illustrative embodiments, in which the principles of the present disclosure are utilized, and the accompanying drawings of which:

FIGS. 2A-2D show an exemplary embodiment of a mobile application of the systems and methods disclosed herein; in this case, a user interface that allows a user or a patient to review and manage physical activities monitored using the systems and methods herein.

FIGS. 4A-4C show an exemplary embodiment of the systems and methods disclosed herein; in this case, a sensor and a pouch for enclosing the sensor(s) therewithin.

FIGS. 5A-5C show an exemplary embodiment of the systems and methods disclosed herein; in this case, the activation via removal of an activation element of the sensor(s) disclosed herein.

FIGS. 7A-7D show an exemplary embodiment of the systems and methods disclosed herein; in this case, inserting a sensor into a pouch.

FIGS. 8A-8B show an exemplary embodiment of the systems and methods disclosed herein; in this case, sealing a sensor within a pouch.

FIGS. 9A-9G show an exemplary embodiment of the systems and methods disclosed herein; in this case, application of the sensor to a patient.

DETAILED DESCRIPTION

Figure 1:
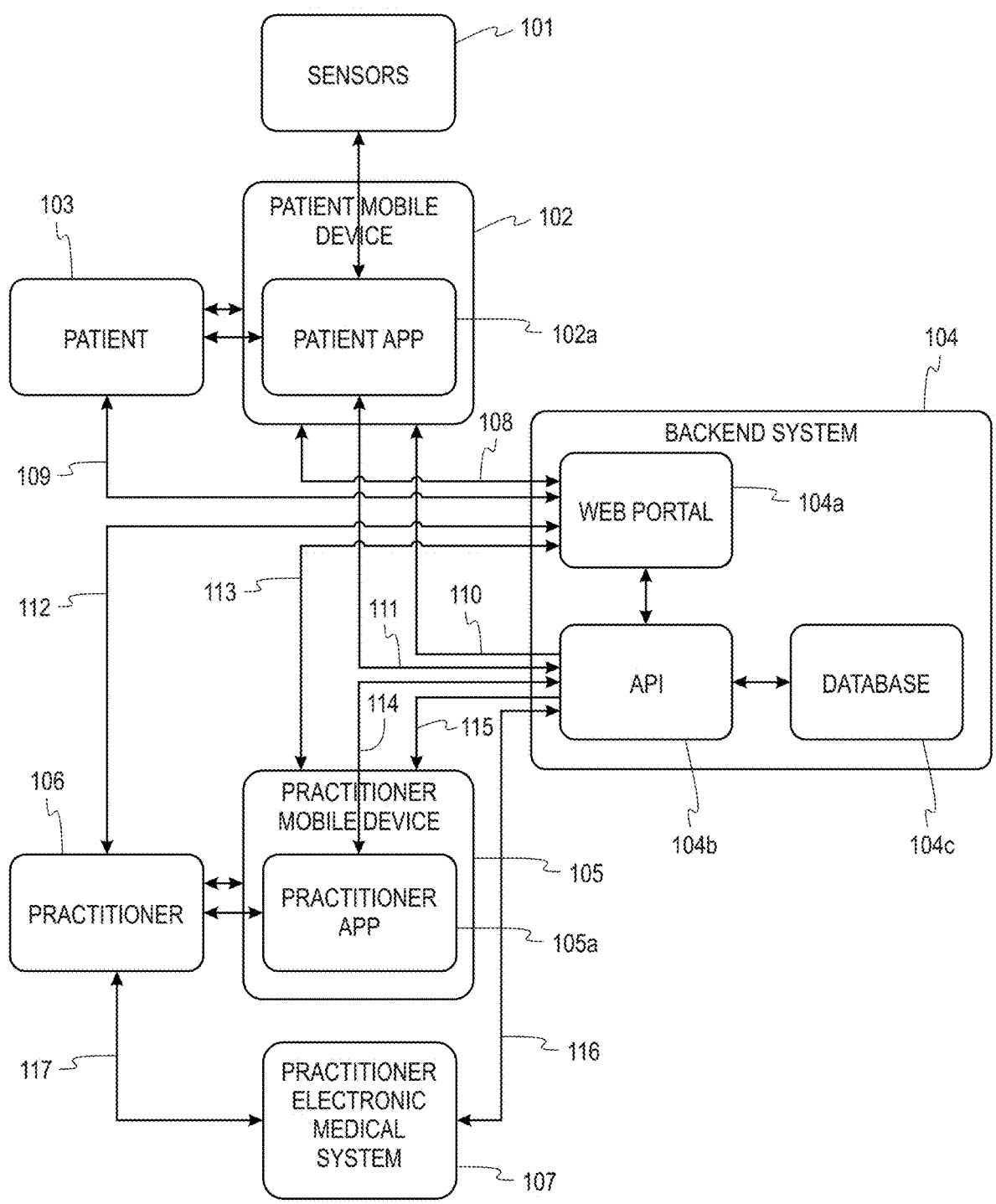
FIG. 1 shows an exemplary diagram of the systems and methods for monitoring physical therapy of the knee and other joints disclosed herein.

In some embodiments, disclosed herein are systems for monitoring a joint of a subject, the system comprising: a plurality of adherent sensors for adhering to skin adjacent the joint, each adherent sensor comprising an adherent surface, a mechanical sensing element for sensing one or more mechanical parameters of the joint, and a transmitter; a local computing device in communication with at least one adherent sensor of the plurality of adherent sensors to receive measurement data from the at least one adherent sensor; and a remote computing device in communication with the local computing device to receive the measurement data and provide analysis of the measurement data to the local computing device, the local computing device providing the analysis to the subject. In some embodiments, at least one adherent sensor of the plurality of adherent sensors comprises a replaceable enclosure and a sensor assembly removable from the enclosure, the replaceable enclosure comprising the adherent surface and the sensor assembly comprising the mechanical sensing element and the transmitter. In some embodiments, the sensor assembly further comprises a power source comprising one or more of a power supply, a battery, a capacitor, or an energy harvesting element. In some embodiments, the at least one adherent sensor of the plurality of adherent sensors comprises an activation element coupled to the power source and the at least one adherent sensor is activated by at least partially removing the activation element. In some embodiments, the at least one adherent sensor of the plurality of adherent sensors is configured to be worn by the subject for at least six to eight weeks and the replaceable enclosure is configured to be replaced after one to two weeks of use while the sensor assembly is continually used after replacement of the replaceable enclosure. In some embodiments, the mechanical sensing element comprises one or more of a strain sensor, a force sensor, a flex sensor, a pressure sensor, an accelerometer, a magnetometer, a gyroscope, a potentiometer, a barometer, a piezoelectric sensor—a pressurized tube sensor, a coiled conductor sensor, a magnetic sensor. In some embodiments, the mechanical sensing element is configured to measure one or more of an elevation of the adherent sensor, a pitch, roll, or yaw of the adherent sensor, an orientation of the adherent sensor relative to gravity, an orientation of the adherent sensor relative to a paired adherent sensor, an orientation of the adherent sensor relative to the joint, motion of the adherent sensor, motion of the joint, motion of tissue adjacent the joint, a deformation of the adherent sensor, stress on the adherent sensor, or strain on the adherent sensor. In some embodiments, the at least one adherent sensor of the plurality of adherent sensors further comprises one or more of a temperature sensor, a humidity sensor, an electrical impedance sensor, an acoustic impedance sensor, an electromyography (EMG) sensor, an oxygen sensor, a pH sensor, an optical sensor, an ultrasound sensor, a glucose sensor, or a biomarker sensor. In some embodiments, the measurement data comprises one or more of an elevation of the at least one adherent sensor, a pitch, roll, or yaw of the at least one adherent sensor, an elevation of the at least one adherent sensor relative to a paired adherent sensor of the plurality of adherent sensors, a temperature of the skin adjacent the joint, motion of the at least one adherent sensor, motion of the at least one adherent sensor relative to the paired adherent sensor, an orientation of the at least one adherent sensor, an orientation of the at least one adherent sensor relative to the paired adherent sensor, an orientation of the at least one adherent sensor relative to the joint, a stretching or shrinkage of the at least one adherent sensor, an oxygenation of tissue adjacent the joint, a humidity of the tissue adjacent the joint, a muscle activity of the joint, an electrical impedance of the tissue adjacent the joint, an acoustic impedance of the tissue adjacent the joint, or one or more biomarkers. In some embodiments, the local computing device comprises one or more of a personal computer, a laptop computer, a tablet computer, a smart phone, a smart TV, a gaming console, a digital media player, a smart speaker, a smart home, a smart watch, a VR/AR goggle or glasses, or a wearable computing device. In some embodiments, the remote computing device comprises one or more of a server, a workstation, a personal computer, a laptop computer, a tablet computer, a smart phone, a smart TV, a gaming console, a digital media player, a smart speaker, a smart home, a smart watch, a VR/AR goggle or glasses, or a wearable computing device. In some embodiments, the plurality of adherent sensors are configured to communicate with one another wirelessly. In some embodiments, the plurality of adherent sensors are configured to communicate with one another wirelessly with a wireless data transfer protocol comprising one or more of Near Field Communication (NFC), wireless USB, ultra-wide-band, ultraband, Wi-Fi, Bluetooth, Bluetooth LE, ZigBee, WiMax, Thread, LoRa, LPWA, an IoT networking protocol, a radio-wave based protocol, a microwave based protocol, an infrared based protocol, or a sound-wave based protocol. In some embodiments, wherein the plurality of adherent sensors is configured to communicate with the local computing device wirelessly. In some embodiments, the plurality of adherent sensors are configured to communicate with one another wirelessly with a wireless data transfer protocol comprising one or more of Near Field Communication (NFC), wireless USB, ultra-wide-band, ultraband, Wi-Fi, Bluetooth, Bluetooth LE, ZigBee, WiMax, Thread, LoRa, LPWA, an IoT networking protocol, a radio-wave based protocol, a microwave based protocol, an infrared based protocol, or a sound-wave based protocol. In some embodiments, one or more of the local computing device or the remote computing device is configured to determine one or more of a range of motion of the joint, a range of flexion of the joint, a range of extension of the joint, a range of rotation of the joint, a motion pattern of the joint, a gait of the subject, a position of the joint, an orientation of the joint, a placement of the plurality of adherent sensors relative to the joint, a compliance of the subject to a joint cooling or heating protocol, a compliance of the subject to a movement protocol, a compliance of the subject for muscle activation/inactivation, swelling of the joint, inflammation of the joint, edema of the joint, impact on the joint, or a physical therapy progress of the subject based on the received measurement data. In some embodiments, one or more of the local computing device or the remote computing device is configured to determine placements and orientations of the plurality of adherent sensors relative to the joint adjacent response and determine one or more of a range of motion of the joint, a range of flexion of the joint, a range of extension of the joint, a range of rotation of the joint, a motion pattern of the joint, a gait of the subject, a position of the joint, or an orientation of the joint based on the determined placement and orientations of the plurality of adherent sensors relative to the joint. In some embodiments, the analysis of the measurement data is automatically generated by the remote computing device. In some embodiments, the systems disclosed herein further comprises a medical professional computing device in communication with the remote computing device to access one or more of the measurement data or at least a first portion of the analysis, and wherein at least a second portion of the analysis of the measurement data is provided by the medical professional through the medical professional computing device. In some embodiments, the medical professional computing device comprises one or more of a personal computer, a laptop computer, a tablet computer, a smart phone, a smart TV, a gaming console, a digital media player, a smart speaker, a smart home, a smart watch, or a wearable computing device. In some embodiments, the local computing device is configured to provide the analysis to the subject via one or more of an audio user interface or a video user interface of the local computing device. In some embodiments, the local computing device is configured to further provide one or more of a reminder, an alarm, a tip, an insight, or an instruction to the subject. In some embodiments, the local computing device is configured to further receive input from the subject and transmit the received input to the remote computing device. In some embodiments, the input comprises one or more of a self-diagnosis parameter, a progress of a physical therapy protocol, a compliance to a physical therapy protocol, or a biometric parameter of the subject. In some embodiments, the joint comprises one or more of an ankle, a knee, a hip, a spine, a neck, a shoulder, an elbow, or a wrist.

In another aspect, disclosed herein are methods for monitoring a joint of a subject over a course of therapy, the method comprising: providing a plurality of adherent sensors adhered to skin adjacent the joint, each adherent sensor comprising an adherent surface, a mechanical sensing element for sensing one or more mechanical parameters of the joint, and a transmitter; measuring measurement data with at least one adherent sensor of the plurality of adherent sensors; transmitting the measurement data from the at least one adherent sensor to a local computing device, the local computing device being in communication with a remote computing device and being configured to transmit the measurement data thereto; receiving the measurement data with the remote computing device; providing analysis of the measurement data to the local computing device from the remote computing device; and providing the analysis to the subject with the local computing device. In some embodiments, at least one adherent sensor of the plurality of adherent sensors comprises a replaceable enclosure and a sensor assembly removable from the enclosure, the replaceable enclosure comprising the adherent surface and the sensor assembly comprising the mechanical sensing element and the transmitter, and wherein the replaceable enclosure is replaced while the sensor assembly is continually used over the course of therapy. In some embodiments, the sensor assembly further comprises a power source comprising one or more of a power supply, a battery, a capacitor, or an energy harvesting element. In some embodiments, the at least one adherent sensor of the plurality of adherent sensors comprises an activation element coupled to the power source and the at least one adherent sensor is activated by at least partially removing the activation element. In some embodiments, the at least one adherent sensor of the plurality of adherent sensors is configured to be worn by the subject for at least six to eight weeks and the replaceable enclosure is configured to be replaced after one to two weeks of use while the sensor assembly is continually used after replacement of the replaceable enclosure. In some embodiments, the mechanical sensing element comprises one or more of a strain sensor, a force sensor, a flex sensor, a pressure sensor, an accelerometer, a magnetometer, a gyroscope, a potentiometer, a barometer, a piezoelectric sensor—a pressurized tube sensor, a coiled conductor sensor, a magnetic sensor. In some embodiments, measuring the measurement data comprises measuring one or more of an elevation of the adherent sensor, an orientation of the adherent sensor relative to gravity, an orientation of the adherent sensor relative to a paired adherent sensor, an orientation of the adherent sensor relative to the joint, motion of the adherent sensor, motion of the joint, motion of tissue adjacent the joint, a deformation of the adherent sensor, a pitch of the adherent sensor, a roll of the adherent sensor, a yaw of the adherent sensor, stress on the adherent sensor, or strain on the adherent sensor with the mechanical sensing element of the at least one adherent sensor. In some embodiments, the at least one adherent sensor of the plurality of adherent sensors further comprises one or more of a temperature sensor, a humidity sensor, an electrical impedance sensor, an acoustic impedance sensor, an electromyography (EMG) sensor, an oxygen sensor, a pH sensor, an optical sensor, an ultrasound sensor, a glucose sensor, or a biomarker sensor. In some embodiments, measuring the measurement data comprises measuring one or more of an elevation of the at least one adherent sensor, an elevation of the at least one adherent sensor relative to a paired adherent sensor of the plurality of adherent sensors, a temperature of the skin adjacent the joint, motion of the at least one adherent sensor, a pitch of the at least one adherent sensor, a roll of the at least one adherent sensor, a yaw of the at least one adherent sensor, motion of the at least one adherent sensor relative to the paired adherent sensor, an orientation of the at least one adherent sensor, an orientation of the at least one adherent sensor relative to the paired adherent sensor, an orientation of the at least one adherent sensor relative to the joint, a stretching or shrinkage of the at least one adherent sensor, an oxygenation of tissue adjacent the joint, a humidity of the tissue adjacent the joint, a muscle activity of the joint, an electrical impedance of the tissue adjacent the joint, an acoustic impedance of the tissue adjacent the joint, or one or more biomarkers. In some embodiments, the local computing device comprises one or more of a personal computer, a laptop computer, a tablet computer, a smart phone, a smart TV, a gaming console, a digital media player, a smart speaker, a smart home, a smart watch, a VR/AR goggle or glasses, or a wearable computing device. In some embodiments, the remote computing device comprises one or more of a server, a workstation, a personal computer, a laptop computer, a tablet computer, a smart phone, a smart TV, a gaming console, a digital media player, a smart speaker, a smart home, a smart watch, a VR/AR goggle or glasses, or a wearable computing device. In some embodiments, the plurality of adherent sensors are configured to communicate with one another wirelessly. In some embodiments, the plurality of adherent sensors are configured to communicate with one another wirelessly with a wireless data transfer protocol comprising one or more of Near Field Communication (NFC), wireless USB, ultra-wide-band, ultraband, Wi-Fi, Bluetooth, Bluetooth LE, ZigBee, WiMax, Thread, LoRa, LPWA, an IoT networking protocol, a radio-wave based protocol, a microwave based protocol, an infrared based protocol, or a sound-wave based protocol. In some embodiments, the plurality of adherent sensors is configured to communicate with the local computing device wirelessly. In some embodiments, the plurality of adherent sensors are configured to communicate with one another wirelessly with a wireless data transfer protocol comprising one or more of Near Field Communication (NFC), wireless USB, ultrawide-band, ultraband, Wi-Fi, Bluetooth, Bluetooth LE, ZigBee, WiMax, Thread, LoRa, LPWA, an IoT networking protocol, a radio-wave based protocol, a microwave based protocol, an infrared based protocol, or a sound-wave based protocol. In some embodiments, the systems disclosed herein further comprises determining one or more of a range of motion of the joint, a range of flexion of the joint, a range of extension of the joint, a range of rotation of the joint, a motion pattern of the joint, a gait of the subject, a position of the joint, an orientation of the joint, a placement of the plurality of adherent sensors relative to the joint, a compliance of the subject to a joint cooling or heating protocol, a compliance of the subject to a movement protocol, a compliance of the subject for muscle activation/inactivation swelling of the joint, inflammation of the joint, edema of the joint, impact on the joint, or a physical therapy progress of the subject based on the received measurement data with one or more of the local computing device or the remote computing device. In some embodiments, the systems disclosed herein further comprises determining one or more of placements and orientations of the plurality of adherent sensors relative to the joint adjacent response and determine one or more of a range of motion of the joint, a range of flexion of the joint, a range of extension of the joint, a range of rotation of the joint, a motion pattern of the joint, a gait of the subject, a position of the joint, or an orientation of the joint based on the determined placement and orientations of the plurality of adherent sensors relative to the joint with one or more of the local computing device or the remote computing device. In some embodiments, the systems disclosed herein further comprise automatically generating the analysis of the measurement data with the remote computing device. In some embodiments, providing analysis of the measurement data to the local computing device from the remote computing device comprises providing a medical professional computing device access to the remote computing device to access one or more of the measurement data or at least a first portion of the analysis, receiving at least a second portion of the analysis from the medical professional computing device as provided by the medical professional with the remote computing device, compiling at least the first and second portions of the analysis, and transmitting the compiled analysis to the local computing device.

In some embodiments, the medical professional computing device comprises one or more of a personal computer, a laptop computer, a tablet computer, a smart phone, a smart TV, a gaming console, a digital media player, a smart speaker, a smart home, a smart watch, or a wearable computing device. In some embodiments, the local computing device provides the analysis to the subject via one or more of an audio user interface or a video user interface of the local computing device. In some embodiments, the systems disclosed herein further comprise providing one or more of a reminder, an alarm, a tip, an insight, or an instruction to the subject with the local computing device. In some embodiments, the systems disclosed herein further comprise receiving input from the subject with the local computing device and transmitting the received input to the remote computing device with the local computing device. In some embodiments, the input comprises one or more of a self-diagnosis parameter, a progress of a physical therapy protocol, a compliance to a physical therapy protocol, or a biometric parameter of the subject. In some embodiments, the joint comprises one or more of an ankle, a knee, a hip, a spine, a neck, a shoulder, an elbow, or a wrist.

In some embodiments, disclosed herein are methods for monitoring a joint of a subject over a course of therapy, the method comprising: activating a first and second adherent sensors, each adherent sensor comprising a replaceable enclosure and a sensor assembly removable from the replaceable enclosure; pairing one or more of the first or second adherent sensors to one another or to a local computing device; adhering the first and second adherent sensors to skin adjacent the joint; and receiving measurement data from one or more of the first or second adherent sensors adhered to the skin adjacent the joint, the measurement data being measured by the sensor assembly of one or more of the first or second adherent sensors. In some embodiments, the sensor assembly of each adherent sensor comprises one or more of a power supply, battery, or energy harvesting element. In some embodiments, each adherent sensor comprises an activation element coupled to the power supply, battery, or energy harvesting element and the at least one adherent sensor is activated by at least partially removing the activation element. In some embodiments, the first and second adherent sensors are coupled to the joint to measure measurement data for at least six to eight weeks. In some embodiments, the methods disclosed herein further comprises, after one to two weeks of use, removing the sensor assembly of the first or second adherent sensor from their respective replaceable enclosure, enclosing the removed sensor assembly with a new replaceable enclosure, and re-adhering the first or second adherent sensor onto the skin adjacent the joint. In some embodiments, the methods disclosed herein further comprises repeatedly replacing the replaceable enclosure of the first or second adherent sensor every one to two weeks of use. In some embodiments, pairing the one or more of the first or second adherent sensors to one another or to the local computing device comprises pairing the first and second adherent sensors to one another in a master-slave relationship. In some embodiments, pairing the one or more of the first or second adherent sensors to one another or to the local computing device comprises pairing each of the first and second adherent sensors individually to the local computing device. In some embodiments, the local computing device is a computing device of the subject or a medical professional. In some embodiments, the first and second adherent sensors are configured to communicate with one another wirelessly. In some embodiments, the first and second adherent sensors are configured to communicate with the local computing device wirelessly. In some embodiments, the first and second adherent sensors are adhered to the skin adjacent the joint in an operating room. In some embodiments, the first and second adherent sensors are adhered to the skin adjacent the joint in an operating room before, during, or after a surgical operation is performed on the joint. In some embodiments, the measurement data is received by one or more of a local computing device of the subject, a remote computing device, or a local computing device of a medical professional. In some embodiments, the methods disclosed herein further comprise providing an analysis of the measurement data to the subject. In some embodiments, the joint comprises one or more of an ankle, a knee, a hip, a spine, a neck, a shoulder, an elbow, or a wrist. In some embodiments, the joint comprises a knee, and wherein adhering the first and second adherent sensors to the skin adjacent the joint comprises adhering the first sensor to skin over or adjacent quadriceps of the subject and adhering the second sensor over or adjacent the shin of the subject.

In some embodiments, disclosed herein are methods for monitoring a joint of a subject, the method comprising: providing first and second adherent sensors adhered to skin adjacent the joint; measuring motion of the first and second adherent sensors adhered to the skin adjacent the joint; identifying one or more cycles of flexion and extension of the joint from the measured motion; identifying one or more impacts on the joint from the measured motion; determining a gait pattern of the subject based on the identified one or more cycles of flexion and extension and the identified one or more impacts on the joint, the gait pattern indicated by a coincidence of the one or more cycles of flexion and extension with the one or more impacts on the joint. In some embodiments, the methods disclosed herein further comprise monitoring the gait pattern for one or more gait inconsistencies. In some embodiments, determining the gait pattern comprises distinguishing walking of the subject from a free movement of the joint of the subject. In some embodiments, the joint comprises one or more of a hip, a knee, or an ankle of the subject. In some embodiments, the motion of the first and second adherent sensors is measured with one or more of a strain sensor, a force sensor, a flex sensor, a pressure sensor, an accelerometer, a magnetometer, a gyroscope, a potentiometer, a barometer, a piezoelectric sensor, a pressurized tube sensor, a coiled conductor sensor, and a magnetic sensor, of the first or second adherent sensors.

In some embodiments, disclosed herein are methods for monitoring a joint of a subject, the method comprising: providing first and second adherent sensors adhered to skin adjacent the joint; measuring a mechanical parameter of the joint with one or more of the first or second adherent sensors; and determining an elevation, a pitch, roll, yaw, or a combination thereof of the joint based on the measured mechanical parameter. In some embodiments, determining the elevation of the joint comprises detecting and comparing relative positions of the first and second sensors. In some embodiments, one or more of the first or second sensors comprise one or more magnetometers. In some embodiments, one or more of the first or second sensors comprise one or more barometers. In some embodiments, the methods disclosed herein further comprises determining if the subject is standing, sitting, lying down in a prone position, or lying down in a supine position based on the determined elevation, pitch, roll, yaw, or the combination thereof. In some embodiments, determining the elevation of the joint comprises tracking the elevation of the joint over a time period to establish a baseline elevation of the joint and identifying deviations from the baseline elevation. In some embodiments, determining the subject's compliance with a therapeutic protocol based on the identified deviations from the baseline elevation.

In some embodiments, disclosed herein are methods for monitoring a joint of a subject, the method comprising: providing first and second adherent sensors adhered to skin adjacent the joint; measuring a mechanical parameter of the joint with one or more of the first or second adherent sensors; measuring a temperature of the skin adjacent the joint with one or more of the first or second adherent sensors; and determining an inflammatory response or an edema of the joint based on the measured mechanical parameter and the measured temperature of the skin. In some embodiments, measuring the mechanical parameter of the joint comprises measuring a stretching or contraction of the one or more of the first or second adherent sensors. In some embodiments, the stretching or contraction of the one or more of the first or second adherent sensors is in a direction transverse to a direction of flexion and extension of the joint. In some embodiments, determining the inflammatory response comprises identifying a coincidence of stretching of the first or second adherent sensors with an increase in measured temperature. In some embodiments, determining an inflammatory response or an edema of the joint further comprises one or more of measuring a change in inductance of a conductive ink trace on one or more of the first or second adherent sensors, measuring an acoustic impedance of tissue adjacent the joint with one or more of the first or second adherent sensors, measuring oxygen saturation of the tissue adjacent the joint with one or more of the first or second adherent sensors, measuring a change in wireless signal strength with one or more of the first or second adherent sensors, or measuring electrical impedance of tissue adjacent the joint with one or more of the first or second adherent sensors.

In some embodiments, disclosed herein are methods for monitoring a joint of a subject, the method comprising: providing first and second adherent sensors adhered to skin adjacent the joint; measuring a mechanical parameter of the joint with one or more of the first or second adherent sensors; determining an inflammatory response or an edema of the joint based on the measured mechanical parameter. In some embodiments, measuring the mechanical parameter of the joint comprises measuring a stretching or contraction of the one or more of the first or second adherent sensors. In some embodiments, the stretching or contraction of the one or more of the first or second adherent sensors is in a direction transverse to a direction of flexion and extension of the joint. In some embodiments, determining an inflammatory response or an edema of the joint further comprises one or more of measuring a change in inductance of a conductive ink trace on one or more of the first or second adherent sensors, measuring an acoustic impedance of tissue adjacent the joint with one or more of the first or second adherent sensors, measuring oxygen saturation of the tissue adjacent the joint with one or more of the first or second adherent sensors, measuring a change in wireless signal strength with one or more of the first or second adherent sensors, or measuring electrical impedance of tissue adjacent the joint with one or more of the first or second adherent sensors.

In some embodiments, disclosed herein are methods for monitoring a knee of a subject, the method comprising: providing a first adherent sensor adhered near a shin of the subject; providing a second adherent sensor adhered near quadriceps of the subject; determining an orientation of the first adherent sensor adhered near the shin relative to a direction of flexion and extension of the knee; determining an orientation of the second sensor adhered near the quadriceps relative to the direction of flexion and extension of the knee; measuring movement of the first and second adherent sensors; and determining one or more of a range of motion, a magnitude of motion, or a direction of movement of the knee based on the measured movement of the first and second adherent sensors and the determined orientations of the first and second sensors relative to the direction and extension of the knee.

In some embodiments, disclosed herein are systems for monitoring a joint of a subject, the system comprising: a computing device for the subject, the computing device comprising a user interface and a digital processing device configured to: receive measurement data from one or more sensors coupled to the joint, store the received measurement data, receive input from the subject through the user interface, transmit the received measurement data and received input to a remote computing device, receive one or more of an analysis of the transmitted measurement data and received input or a treatment regimen from the remote computing device, and provide one or more of the received analysis or treatment regimen to the subject through the user interface. In some embodiments, the digital processing device is further configured to authenticate the one or more sensors prior to coupling to the one or more sensors to receive the measurement data. In some embodiments, the digital processing device is further configured to authenticate the subject through the user interface prior to receiving the input from the subject. In some embodiments, the digital processing device is further configured to set a sampling interval for receiving the measurement data from the one or more sensors. In some embodiments, the digital processing device is further configured to set a transmission interval for transmitting the measurement data to the remote computing device. In some embodiments, the digital processing device is configured to provide the one or more of the received analysis or the treatment regimen by providing one or more of an alarm, a notification, a reminder, a goal, or a communication interface with a medical professional to the subject. In some embodiments, the digital processing device is further configured to generate a real-time analysis of the received measurement data. In some embodiments, the digital processing device is configured to transmit the real-time analysis to one or more of the remote computing device or a computing device of a medical professional. In some embodiments, the digital processing device is configured to display the real-time analysis to the subject through the user interface. In some embodiments, the real-time analysis comprises one or more of a range of motion of the joint, a temperature of the joint, or an elevation of the joint. In some embodiments, the input from the subject comprises one or more of a recorded event, a progression in a therapeutic protocol, or feedback on the therapeutic protocol from the subject.

In some embodiments, disclosed herein are systems for monitoring a joint of a subject, the system comprising: a computing device for a medical professional monitoring the subject, the computing device comprising a user interface and a digital processing device configured to: provide measurement data of the subject to the medical professional through the user interface, the measurement data being received from a remote computing device and originating from one or more sensors coupled to the joint to measure the measurement data and transmit the measurement data to the remote computing device, providing input from the subject to the medical professional through the user interface, the input being received from a local computing device of the subject, receiving an analysis of one or more of the measurement data or subject input from the medical professional through the user interface, receiving a treatment regimen from the medical professional through the user interface, and transmitting one or more of the received analysis or received treatment regimen to the remote computing device, the remote computing device transmitting the one or more of the received analysis or received treatment regimen to the local computing device of the subject. In some embodiments, the user interface comprises a two-way communication interface between the medical professional and the subject. In some embodiments, the measurement data is provided to the medical professional in real-time. In some embodiments, the digital processing device is further configured to authenticate the medical professional through the user interface prior to receiving the input from the subject. In some embodiments, the digital processing device is further configured to set a sampling interval for receiving the measurement data from the one or more sensors. In some embodiments, the digital processing device is further configured to set a transmission interval for the local computing device of the subject to transmit the measurement data. In some embodiments, one or more of the analysis of the one or more of the measurement data or the subject input or treatment regimen is generated by the medical professional based at least partially on an automated analysis of one or more of the measurement data or the subject input. In some embodiments, the automated analysis is generated by the digital processing device. In some embodiments, the automated analysis is generated by the remote computing device and provided therefrom. In some embodiments, the digital processing device is further configured to generate a real-time analysis of the received measurement data. In some embodiments, the digital processing device is configured to display the real-time analysis to the medical professional through the user interface. In some embodiments, the real-time analysis comprises one or more of a range of motion of the joint, a temperature of the joint, or an elevation of the joint. In some embodiments, the digital processing device is further configured to generate a progress report for the subject and the user interface is configured to display the progress report to the medical professional.

In some embodiments, disclosed herein are systems for monitoring a joint of a subject, the system comprising: a remote computing device in communication with local computing devices for both the subject and a medical professional monitoring the subject, the remote computing device comprising a digital processing device configured to: receive measurement data from the local computing device of the subject, the measurement data originating from one or more sensors coupled to the joint to measure the measurement data and transmit the measurement data to the local computing device, receive input from the subject from the local computing device of the subject, store one or more of the received measurement data or received input in a database, generate an analysis of one or more of the received measurement data or received input from the subject, generate a treatment regimen based on one or more of the received measurement data or received input from the subject, and transmit one or more of the generated analysis or generated treatment regimen to one or more of the local computing device of the subject or the local computing device of the medical professional. In some embodiments, the remote computing device is configured to provide to one or more of the subject or the medical professional access thereto through a user interface. In some embodiments, the user interface comprises a web portal. In some embodiments, the digital processing device is configured authenticate the one or more of the subject or the medical professional prior to providing the access. In some embodiments, the digital processing device is configured to generate the treatment regimen by selecting select the treatment regimen from a plurality of treatment regimens stored in a database based on one or more of the received measurement data or received input. In some embodiments, the digital processing device is configured to generate one or more of the analysis or the treatment regimen by transmitting one or more of the measurement data or the input from the subject to the medical professional and receiving an input from the medical professional in response. In some embodiments, one or more of the analysis of the one or more of the measurement data or the subject input or treatment regimen is generated by the medical professional based at least partially on an automated analysis of one or more of the measurement data or the subject input. In some embodiments, the automated analysis is generated by the digital processing device. In some embodiments, the digital processing device is configured to provide an intermediary for two-way communication between the medical professional and the subject. In some embodiments, the digital processing device is further configured to set a sampling interval for receiving the measurement data from the one or more sensors. In some embodiments, the digital processing device is further configured to set a transmission interval for the local computing device of the subject to transmit the measurement data.

Overview

In some embodiments, disclosed herein are systems and methods for monitoring physical therapy or physical exercise of the knee and other joints, preferably after a surgical operation. FIG. 1 shows a non-limiting exemplary embodiment of the systems and methods disclosed herein. In this particular embodiment, one or more sensors 101 adherent to the patient communicates to the patient's local computing device 102 via a communications element and measurement data from sensor(s) are received at the patient application 102a of the patient's local computing device. The patient application, optionally a mobile application, transmits through connection 111 the measurement data to the web portal 104a of the backend remote computing device 104, optionally via an application programming interface (API) 104b where the measurement data are processed, analyzed, and/or stored. In this embodiment, the web portal of the backend remote computing device optionally receives input from the patient 103 either directly 109 or via the patient's application 102a. In some embodiments, the web portal utilizes the received measurement data, optionally with received user input, to generate analysis of the measurement data and/or treatment regimen for the patient. The analysis of the measurement data and/or treatment regimen for the patient are transmitted through the connection 111 via the API to the patient's application on the local computing device of the subject and allow the patient 103 to review analysis of the measurement data and monitor his/her progress. In some embodiments, such received input from the subject, measurement data, analysis of the measurement data (generated by the web portal), and/or treatment regimen (generated by the web portal) are stored in a database 104c through the API 104b. In the same embodiment, the received input from the subject, measurement data, analysis of the measurement data (generated by the web portal), and/or optional treatment regimen (generated by the web portal) for the patient are transmitted 114 via the API 104b to the practitioner's application 105a on the local computing device of the medical professional 105 to allow the doctor, physician, or other medical practitioner to review and monitor progress of his/her patient. In some embodiments, the local computing device for a medical professional for monitoring the subject receives measurement data of the subject from the patient's application directly. In this embodiment, the local computing device 105 also receives an analysis of one or more of the measurement data from the medical professional 106 through the practitioner's application 105a optionally based on information received from the backend remote computing device or from the patient's application. In some embodiments, the medical professional provides another treatment regimen through the practitioner's application, and analysis of measurement data (from the practitioner) and treatment regimen (from the practitioner) are transmitted 114 to the remote computing device to be relayed to the patient 114, 111 or stored in the remote computing device 114, 104b, 104c.

Continuing to refer to FIG. 1, in some embodiments, the medical professional or practitioner 106 enters input that can be directly received 112 at the web portal of 104a the backend remote computing device for generating measurement data analysis and/or treatment regimen. Such input may also be transferred to the patient through the connection 111 or stored at the remote computing device with corresponding measurement data analysis and/or treatment regimen 104c. Additional input 117 of the medical practitioner through an electronic medical system which communicates with the backend remote computing device 116 can be optionally incorporated to deliver through connection 111 analysis and treatment regimen to the patient. For example, the doctor, physician, or other medical practitioner may request the electronic medical system to send medical history of the patient related to the measurement data to the web portal so that the medical history can be incorporated in generating analysis of measurement data and/or customized treatment regimen.

Sensing Assemblies and Pouches

In some embodiments, the systems and methods disclosed herein include one or more sensors or equivalent herein sensing elements. In some embodiments, the sensors include one or more adherent sensors for adhering to skin of a subject. In some embodiments, the skin is adjacent to one or more joints of the subject. In some embodiments, a sensor is adhered to a skin which is no more than about 0 cm to about 50 cm to a geometrical center of the joint or to a closest edge of the joint. In some embodiments, the joint comprises one or more of an ankle, a knee, a hip, a spine, a neck, a shoulder, an elbow, a finger, a toe or a wrist. In some embodiments, the sensors detect the relative placement of one another and/or the ranges and orientations of motion relative to one another to identify the joint they are placed thereon, and can further provide this information to one or more other connected devices.

In some embodiments, a sensor herein includes a sensor assembly removable from the enclosure. In some embodiments, the sensor assembly includes a sensing element, a transmitter, a communications element. In some embodiments, the communications element includes a receiver, and/or a transceiver. In some embodiments, the sensor assembly includes a power source comprising one or more of a power supply, a battery, a capacitor, an inductor, a resistor, an energy harvesting element, or an energy transforming element. In some embodiments, the sensor assembly includes a microcontroller (MCU) or a microprocessor (MPU). In some embodiments, the sensor assembly includes an electrical circuit connected to the sensing element, the MCU, the MPU, the receiver, the transmitter, and/or transceiver. In some embodiments, the sensor, the electrical circuit, MCU, and/or MPU can be positioned close enough to each other thereby any two or more of them can be connected to each other either with wires or wirelessly.

Referring to FIGS. 4A-4C, in a particular embodiment, a sensing element 401, and a battery 402 within an enclosure 404 are enclosed in the replaceable pouch including two reversibly attachable pieces, 403a and 403b. In this embodiment, a portion of the pouch 403c is transparent on either or both of the two pieces. FIG. 4B shows the sensor 401 and battery 402 with activation loop 405 cut off and inserted into the pouch; FIG. 4C shows an exemplary embodiment of the the pouch 403.

In some embodiments, the sensing element is a mechanical element. In some embodiments, the sensing element includes one or more of a strain sensor, a force sensor, a flex sensor, a pressure sensor, a stretch sensor, a velocity sensor, an accelerometer, a magnetometer, a gyroscope, a potentiometer, a barometer, a piezoelectric sensor, a pressurized tube sensor, a coiled conductor sensor, a magnetic sensor, or a magnetometer. In some embodiments, the sensing element includes one or more of a temperature sensor, a humidity sensor, an electrical impedance sensor, an acoustic impedance sensor, an electromyography (EMG) sensor, an oxygen sensor, a pH sensor, an optical sensor, an ultrasound sensor, a glucose sensor, a biomarker sensor, a heart rate monitor, a respirometer, an electrolyte sensor, a blood pressure sensor, an EEG sensor, an ECG sensor, a body hydration sensor, a carbon dioxide sensor, a carbon monoxide sensor, a blood alcohol sensor, and a Geiger counter. In some embodiments, the sensing element includes a location sensor (e.g., global positioning system (GPS) sensors, mobile device transmitters enabling location triangulation), vision sensors (e.g., imaging devices capable of detecting visible, infrared, or ultraviolet light, such as cameras), proximity sensors (e.g., LIDAR, time-of-flight cameras), inertial sensors (e.g., inertial measurement units (IMUs)), altitude sensors, conductive-fiber sensor, or field sensors (e.g., magnetometers, electromagnetic sensors). Any suitable number and combination of sensors can be used in a sensing element, such as one, two, three, four, five, or more sensors. For instance, the sensing element may include any suitable combination of active sensors (e.g., sensors that generate and measure energy from their own source) and passive sensors (e.g., sensors that detect available energy). In some embodiments, the sensor herein is an Internet of Things (IoT) sensor, actuator, and/or effectors.

In some embodiments, a sensor or sensing element disclosed here has a size in the range of about 0.1 cm$^2$ to about 50 cm cm$^2$. In some embodiments, a sensor or sensing element 401 disclosed here has a size in the range of about 0.5 cm$^2$ to about 10 cm$^2$. In some embodiments, a sensor or sensing element disclosed here has a size in the range of about 1 cm$^2$ to about 8 cm$^2$. In some embodiments, a sensor or sensing element disclosed here has a size in the range of about 2 cm$^2$ to about 6 cm$^2$. In some embodiments, a sensor or sensing element disclosed here has a size in the range of about 2 cm$^2$ to about 4 cm$^2$. In some embodiments, the enclosure 404 with sensor or sensing element and battery encloses, as in FIG. 4B, has a size in the range of about 5 cm$^2$ to about 30 cm$^2$. In some embodiments, the enclosure with sensor or sensing element and battery encloses, has a size in the range of about 10 cm$^2$ to about 16 cm$^2$. In some embodiments, the pouch 403 has a size in the range of about 10 cm$^2$ to about 50 cm$^2$. In some embodiments, the pouch 403 has a size in the range of about 25 cm$^2$ to about 35 cm$^2$.

In some embodiments, mechanical sensing element is configured to measure one or more of an elevation of the sensor, an orientation of the sensor relative to gravity, an orientation of the sensor relative to a paired sensor, an orientation of the sensor relative to the joint, motion of the adherent sensor, motion of the joint, motion of tissue adjacent the joint, a deformation of the sensor, stress on the adherent sensor, or strain on the adherent sensor. In some embodiments, the orientation of the sensor is relative to a pre-selected fixed reference point, for example, to the ground when the ground stays still. In some embodiments, the orientation of the sensor is relative to its orientation in an earlier or a later time point. In some embodiments, the subtraction of two relative orientations of the sensor at two time points generates movement information of the sensor. In some embodiments, the orientation is two dimensional or three dimensional. In some embodiments, the sensing element measures a velocity, acceleration, a speed, an angular momentum, a shear, a twist, a roll, a yaw, a pitch of the sensor, the joint, or tissue adjacent the joint.

In some embodiments, the measurement data includes one or more of an elevation of the sensor, an elevation of the sensor relative to a paired sensor, an altitude of sensor, an altitude of the sensor relative to a paired sensor, a temperature of the skin adjacent the joint, motion of the sensor, motion of the sensor relative to the paired sensor, an orientation of the sensor, an orientation of the sensor relative to the paired sensor, an orientation of the sensor relative to the joint, a stretching or shrinkage of the sensor, an oxygenation of tissue adjacent the joint, a humidity of the tissue adjacent the joint, a muscle activity of the joint, an electrical impedance of the tissue adjacent the joint, an acoustic impedance of the tissue adjacent the joint, a blood glucose level, a blood alcohol level, a carbon dioxide level, a PH level, a blood pressure level, a heart rate, a body hydration level, one or more electrolytes, or one or more biomarkers.

In some embodiments, a sensor herein includes a replaceable enclosure, for example, a pouch. In some embodiments, the enclosure includes an adherent surface. In some embodiments, the enclosure includes a transparent portion. In some embodiments, the enclosure includes two reversibly attachable pieces. In some embodiments, at least one piece includes a transparent portion as a pouch window. In some embodiments, the enclosure includes an adhesive edge that may be covered by a non-adhesive liner.

Figure 6A:
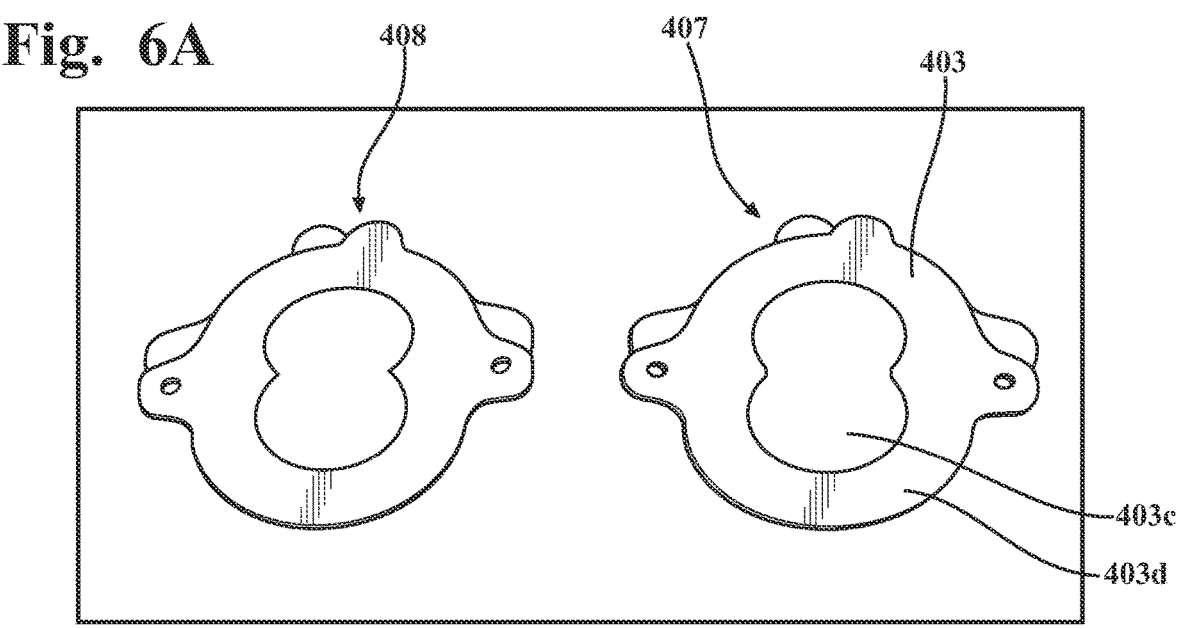
FIGS. 6A-6B show an exemplary embodiment of the systems and methods disclosed herein; in this case, inspecting and opening pouch(es) herein for enclose the sensor therewithin.
Figure 6B:
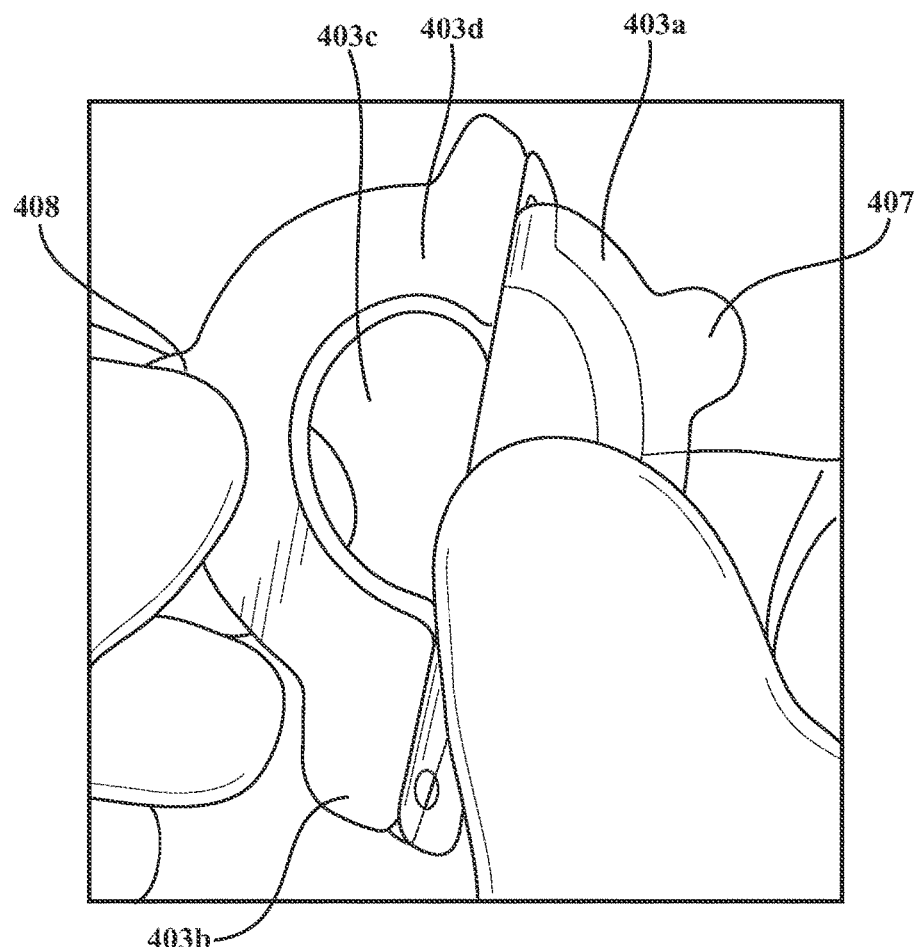

Referring to FIG. 6A, in a particular embodiment, each replaceable pouch 403 includes two attachable pieces 403a, 403b and one piece includes a clear tab 407, the other piece includes a while tab 408 on a top portion of the pouch. In this embodiment, at least one piece of the pouch includes a transparent portion 403c and a non-transparent portion 403d. In some embodiments, one or both of the pieces includes an adhesive surface. In some embodiments, the adhesive surface is close to or at the edge of the pouch. Referring to FIG. 6B, the pouch is opened by separating the two reversibly attachable pieces via pulling the clear and white tabs.

Referring to FIGS. 7A-7B, in a particular embodiment, the sensor 401 along with its battery 402 is inserted into the opened pouch 403. In this particular embodiment, the sensor is inserted by the user holding at least a portion of battery 402 but not putting any pressure on the sensing element. The contoured surface of the sensor 401 is inserted toward the white tab (not shown). In this particular embodiment, the sensor is inserted until fully seated at the bottom of the pouch, thereby the sensor edges are visible from the transparent pouch window 403c.

Referring to FIGS. 7C-7D, in a particular embodiment, after insertion of the sensor, the white release liner 409 may be removed starting from one end of the opening away from the pouch. In some embodiments, the white release liner 409 is attached on one attachment pieces 403b. In some embodiments, the removal of the release liner exposes an adherent surface 410 on at least a part of the non-transparent portion 403d of the pouch thereby enabling adhesion of the two pieces of the pouch. In some embodiments, the adhesive surface may be on both pieces of the pouch. In some embodiments, the adherent surface is close to or at the edge of the pouch.

Referring to FIGS. 8A-8B, in a particular embodiment, the sensor 401 and battery 402 are sealed into the pouch 403 optionally by a medical practitioner 416, and the pouch is closed by pressing the adherent surface 410 at or close to the edges of the pouch. The sealed pouch, in this embodiment, is hold by a medical practitioner or a user by its ear 411.

Figure 9A:
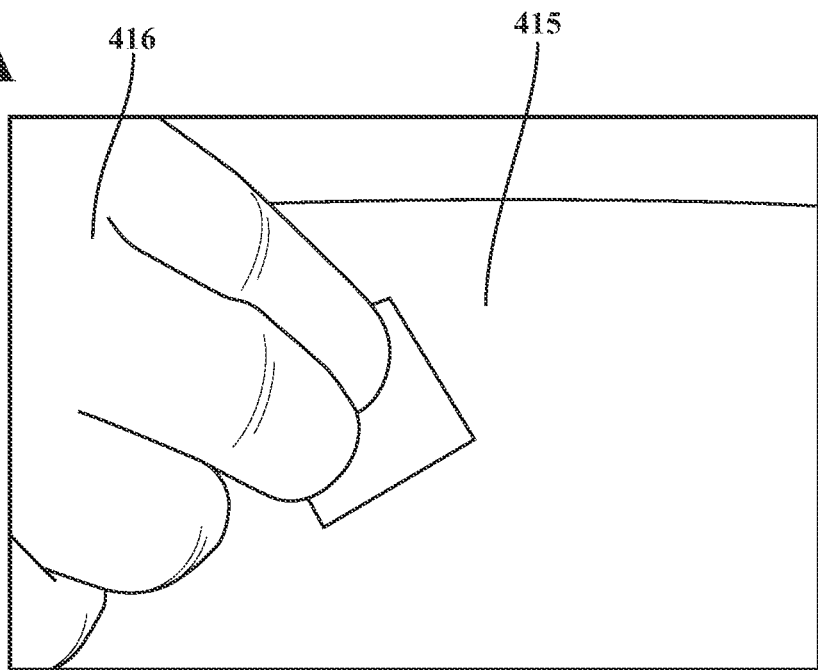
Figure 9B:
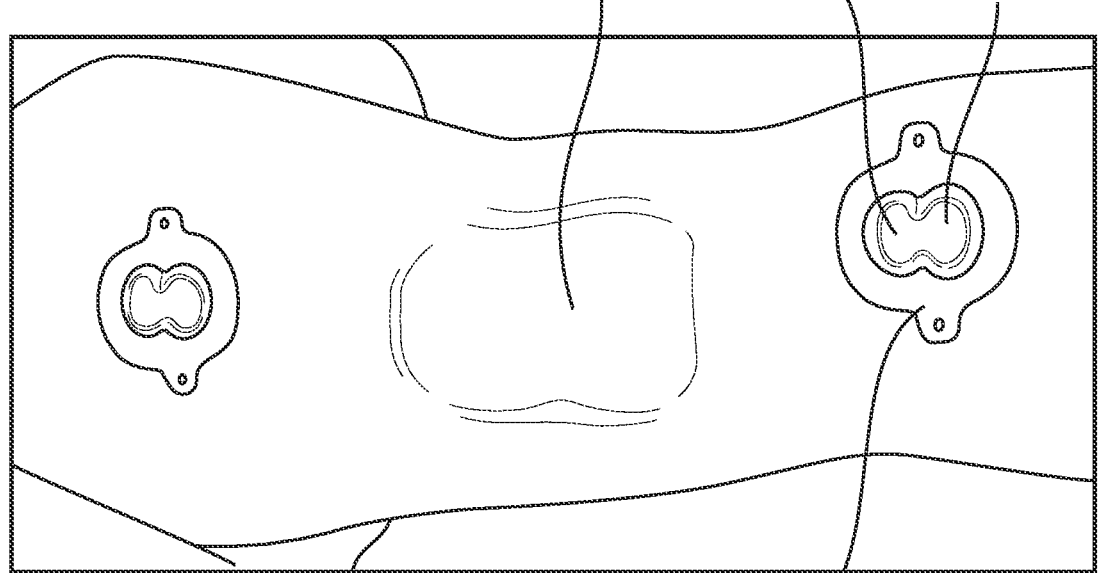

In some embodiments, the sensor application starts with preparing the skin 415 at the application site, as in FIG. 9A, by a medical practitioner 416 or the subject. In some embodiments, the skin is cleaned, optionally with isopropyl alcohol. After skin preparation, the joint 414 to be measured, in this particular embodiment, the knee, is placed in full extension and two sensor assemblies enclosed in corresponding pouches 401, 402, 403 are temporarily placed on skin adjacent the joint to confirm alignment of the sensors, as in FIG. 9B. When the temporary placement of the sensors are aligned, as in FIGS. 9C-9D, the release liner 412 is removed from the back of the sensor to expose an adherent surface 413 that enable attachment of the pouch and the sensor assembly therewithin to the skin. In some embodiments, the release liner 412 is attached on one attachment pieces 403a. In this embodiment, one or more ears 411 of pouch are used for holding the sensor during adherent placement so that contact with the adhesive surface may be avoid. In some embodiments, the non-adhesive or adhesive ear enables easy application of the sensor to the skin and easy removal of a sensor from the skin. The sensor is applied to the skin at the desired application site. Optionally, the sensor is pressed firmly onto the skin to improve adhesion. Referring to FIGS. 9E-9G, in a particular embodiment, the non-transparent, non-adhesive layer 417 at the front of the pouch 403 can be removed. In some embodiments, non-adhesive layer 417 includes the non-transparent portion 403d. In some embodiments, such application process in FIGS. 9A-9F is repeated for a second sensor and any other additional sensors.

In some embodiments, the releasable pouch, 403 herein advantageously encloses and protects the sensor, battery, and other elements of the assembly from exposure to heat, sweat, water, or other external influences that may interfere with the function(s) of the enclosed element. In some embodiments, the pouch enables easy application and easy removal of the sensing assembly without damages to the enclosed elements. In some embodiments, may be replaced without the need to replace the sensing element and other elements enclosed therewithin.

In some embodiments, a releasable pouch 403 disclosed here has a size in the range of about 0.1 $cm^2$ to about 50 $cm^2$. In some embodiments, a pouch disclosed here has a size in the range of about 10 $cm^2$ to about 40 $cm^2$. In some embodiments, a pouch disclosed here has a size in the range of about 25 $cm^2$ to about 35 $cm^2$.

In some embodiments, the pouch is made of one or more materials that are flexible. In some embodiments, the materials including one or more of: polymer, biomaterial, plastic, polyurethane, and polyethylene.

In some embodiments, a sensor or sensing element herein is configured to communicate with other sensor(s) wirelessly. In some embodiments, a sensor or sensing element herein is configured to communicate with the local computing device wirelessly. In some embodiments, a sensor or sensing element here in is configured to communicate with the remote computing device wirelessly.

In some embodiments, the sensors are configured to communicate with one another, with the local computing device, or the remote computing device wirelessly via a receiver, a transmitter, or a transceiver of the sensing assembly with a wireless data transfer protocol. In some embodiments, the receiver, the transmitter, or transceiver is configured to communicate data using one or more wireless data transfer protocols herein. For example, the receiver, the transmitter, or transceiver herein includes a radio transceiver with an antenna or connection for an external antenna for radio frequency signals. In some embodiments, the wireless data transfer protocol includes one or more of Near Field Communication (NFC), wireless USB, ultra-wide-band, ultraband, Wi-Fi, Bluetooth, Bluetooth LE, ZigBee, WiMAX, Thread, LoRa, LPWA, an IoT networking protocol, a radio-wave based protocol, a microwave based protocol, an infrared based protocol, an optical-wave protocol, electromagnetic induction-based protocol, a ultrasonic-wave based protocol, or a sound-wave based protocol.

In some embodiments, the sensing element is connected to a MCU or MPU, and the MCU or MPU is connected to the transmitter, receiver, and/or receiver to enable data transfer from the sensing element to the local computing device or the remote computing device. In some embodiment, such connection is configured to allow controlling of the sensing element from the local or remote computing device.

In some embodiments, a sensor includes an activation element coupled to the power source and the sensor is activated by at least partially removing the activation element. In some embodiments, the activation element is accessible for removal before or after the sensor is properly placed within the replaceable enclosure. In some embodiments, the sensor includes a signal when it is properly activated. In some embodiments, the signal is a visual, audio, or mechanical signal. In some embodiments, the signal is one or more blinks from a LED. In some embodiments, the signal includes a strength or magnitude that is perceivable to a user.

Referring to FIG. 5A, in a particular embodiment, two sensing elements 401, each with a battery 402, are not activated as the activation element 405 remains attached to the corresponding sensing element. Removal of the activation loop by cutting in this particular embodiment, as shown in FIG. 5B activates the sensing element. The successful activation is confirmed by blinking of a LED 406 of the sensing element that is perceivable to a user, as in FIG. 5C. In this particular embodiment, the LED of the sensor blinks more than 5 blinks. In some embodiments, the sensor blinks any number from 1 to 1000. In some embodiments, the sensor vibrates or beeps for confirmation of an activation. In some embodiments, the sensor may transmit any perceivable visual, sound, or mechanical signal to the user to confirm activation.

In some embodiments, the sensor is configured to be worn by the subject for at least six to eight weeks and the replaceable enclosure is configured to be replaced after one to two weeks of use while the sensor assembly is continually used after replacement of the replaceable enclosure. In some embodiments, the sensor is configured to be worn by the subject for at least six to eight weeks and the replaceable enclosure is configured to be replaced after six to eight weeks of use while the sensor assembly is continually used after replacement of the replaceable enclosure. In some embodiments, the sensor is configured to be worn by the subject the replaceable enclosure is configured to be replaced after the skin adhesive fails or starts to show signs of weakening. In some embodiments, the sensor is configured to be worn by the subject for about one to three weeks or until the adhesion to skin has weakened and the replaceable enclosure is configured to be replaced.

In some embodiments, the systems and methods herein includes one or more steps for monitoring a joint of a subject over a course of therapy, the steps (may be in order(s) different from the following) includes: activating one or more sensors disclosed herein by removal of the activation element (FIGS. 5A-5C); pairing one or more of sensors to one or more other sensors and/or to a local computing device; adhering the sensors to skin adjacent the joint; receiving measurement data from one or more of the sensors adhered to the skin adjacent the joint; and providing an analysis of the measurement data to the subject. In some embodiments, after a pre-determined time period, the systems and methods herein includes one or more steps of: removing the sensor assembly of the sensor(s) from their respective replaceable enclosure, enclosing the removed sensor assembly with a new replaceable enclosure, re-adhering the sensor(s) onto the skin adjacent the joint, and repeating receiving measurement data from one or more of the sensors adhered to the skin adjacent the joint; and repeating providing an analysis of the measurement data to the subject. In some embodiments, the activation element is coupled to the power supply, battery, energy harvesting element, an energy transforming element, MCU, MPU, or the electrical circuit and the sensor is activated by at least partially removing the activation element. In some embodiments, the pre-determined time period is in the range of 1 day to 4 weeks. In some embodiments, the pre-determined time period is in the range of 7 day to 10 days. In some embodiments, the pre-determined time period is in the range of 5 day to 9 days. In some embodiments, the pre-determined time period is in the range of 12 day to 16 days. In some embodiments, the pre-determined time period is in the range of 10 day to 12 days. In some embodiments, the pre-determined time period is in the range of 6 day to 15 days. In some embodiments, the systems and methods disclosed herein include repeatedly replacing the replaceable enclosure of the sensor(s), for example, after every one to two weeks of use. In some embodiments, pairing one or more of sensors to one or more other sensors or to the local computing device comprises pairing the sensors in a master-slave relationship. In some embodiments, pairing one or more of the sensors comprises pairing each of the one or more sensors individually to the local computing device. In some embodiments, the joint comprises one or more of an ankle, a knee, a hip, a spine, a neck, a shoulder, an elbow, a finger, a toe, or a wrist. In some embodiments, the joint includes one or more knees, and wherein adhering the sensors to the skin adjacent the joint includes adhering the first sensor to skin over or adjacent quadriceps of the subject and adhering the second sensor over or adjacent the shin of the subject, as shown in FIG. 9G. In some embodiments, one or more sensors are adhered to the skin adjacent the joint in an operating room before, during, or after a surgical operation is performed on the joint. In some embodiments, the measurement data is received by one or more of a local computing device of the subject, a remote computing device, or a local computing device of a medical professional.

In some embodiments, the systems and methods herein are for monitoring a joint of a subject and include one or more steps of the following, not necessarily in following order: providing one or more sensors adhered to skin adjacent the joint; measuring motion of the one or more sensors adhered to the skin adjacent the joint; identifying one or more cycles of flexion and extension of the joint from the measured motion; identifying one or more impacts on the joint from the measured motion; determining a gait pattern of the subject based on the identified one or more cycles of flexion and extension and the identified one or more impacts on the joint, the gait pattern indicated by a coincidence of the one or more cycles of flexion and extension with the one or more impacts on the joint; monitoring the gait pattern for one or more gait inconsistencies. In some embodiments, determining the gait pattern comprises distinguishing walking of the subject from a free movement of the joint of the subject. In some embodiments, the free movement of joint of the subject is when the subject is sitting, lying down, standing with one leg, or in any other positions different from walking, jogging, jumping, or running. In some embodiments, the joint comprises one or more of a hip, a knee, or an ankle of the subject. In some embodiments, the motion of the sensor(s) is measured with one or more sensors disclosed herein. In some embodiments, the one or more sensors includes one or more of a strain sensor, a force sensor, a flex sensor, a stretch sensor, an inertial sensor, an altitude sensor, a pressure sensor, an accelerometer, a magnetometer, a gyroscope, a potentiometer, a barometer, a piezoelectric sensor, a flex sensor, a pressurized tube sensor, a coiled conductor sensor, a magnetic sensor, an inertial sensor, or a magnetometer of the sensor(s).

In some embodiments, the systems and methods herein are for monitoring a joint of a subject and include one or more steps of the following, not necessarily in following order: providing one or more sensor adhered to skin adjacent the joint; measuring a mechanical parameter of the joint with one or more sensors; and determining an elevation of the joint based on the measured mechanical parameter, and determining if the subject is standing, sitting, lying down in a prone position, or lying down in a supine position based on the determined elevation; determining the subject's compliance with a therapeutic protocol based on the identified deviations from the baseline elevation. In some embodiments, determining the elevation of the joint comprises detecting and comparing relative positions of a first and second sensor among one or more sensors. In some embodiments, one or more sensors comprise one or more of: magnetometers, barometers, stretch sensor, gyroscope, flex sensor, conductive fiber sensor, and inertial sensor. In some embodiments, determining the elevation of the joint includes tracking the elevation of the joint over a time period to establish a baseline elevation of the joint and identifying deviations from the baseline elevation. In some embodiments, one of the sensors is adhered to skin over or adjacent quadriceps of the subject and the second sensor over or adjacent the shin of the subject. In some embodiment, the time period is from 1 second to 24 hours.

In some embodiments, the systems and methods herein are for monitoring a joint of a subject and include one or more steps of the following, not necessarily in following order: providing one or more sensors adhered to skin adjacent the joint; measuring a mechanical parameter of the joint with one or more of the sensors; measuring a temperature of the skin adjacent the joint with the sensor(s); and determining an inflammatory response or an edema of the joint based on the measured mechanical parameter and the measured temperature of the skin. In some embodiments, measuring the mechanical parameter of the joint comprises measuring a stretching or contraction of the one or sensors. In some embodiments, the stretching or contraction of the one or more sensors is in a direction, or perpendicular to a direction of flexion and extension of the joint. In some embodiments, the stretching or contraction of the one or more sensors is in a direction, 1106 in FIG. 11, or perpendicular to a current direction of flexion and extension of the joint, 1105 in FIG. 11. In some embodiments, determining the inflammatory response comprises identifying a coincidence of stretching of the sensor(s) with an increase in measured temperature. In some embodiments, determining an inflammatory response or an edema of the joint further comprises one or more of measuring a change in inductance of a conductive ink trace on one or more of the sensor(s), measuring an acoustic impedance of tissue adjacent the joint with one or more of the sensor(s), measuring oxygen saturation of the tissue adjacent the joint with one or more of the sensor(s), measuring a change in wireless signal strength with one or more of the sensor(s), or measuring electrical impedance of tissue adjacent the joint with one or more of the sensor(s). In some embodiments, sensor assembly is programmed to alert measurements or parameters that are out of a pre-determined range or changing from a pre-determined baseline. For example, the sensor assembly including a temperature sensor may be programmed to generate an alert when the sensed temperature is increasing to a value which may indicate inflammation or infection.

In some embodiments, the systems and methods herein are for monitoring a joint of a subject and include one or more steps of the following, not necessarily in following order: providing one or more sensors adhered to skin adjacent the joint; measuring a mechanical parameter of the joint with one or more sensors; determining an inflammatory response or an edema of the joint based on the measured mechanical parameter. In some embodiments, measuring the mechanical parameter of the joint comprises measuring a stretching or contraction of the one or more of the sensors. In some embodiments, the stretching or contraction of the one or more of the sensors is in a direction transverse to a direction of flexion and extension of the joint. In some embodiments, the stretching or contraction of the one or more sensors is in a direction, 1106 in FIG. 11, or perpendicular to a current direction of flexion and extension of the joint, 1105 in FIG. 11. In some embodiments, determining an inflammatory response or an edema of the joint further comprises one or more of measuring a change in inductance of a conductive ink trace on one or more sensors, measuring an acoustic impedance of tissue adjacent the joint with one or more sensors, measuring oxygen saturation of the tissue adjacent the joint with one or more sensors, measuring a change in wireless signal strength with one or more sensors, or measuring electrical impedance of tissue adjacent the joint with one or more sensors.

In some embodiments, the systems and methods herein are for monitoring a joint of a subject and include one or more steps of the following, not necessarily in the following order: providing a first adherent sensor adhered near a shin or lateral to the shin of the subject; providing a second adherent sensor adhered near quadriceps or lateral to the quadriceps of the subject; determining an orientation of the first adherent sensor adhered near the shin relative to a direction of flexion and extension of the knee; determining an orientation of the second sensor adhered near the quadriceps relative to the direction of flexion and extension of the knee; measuring movement of the first and second adherent sensors; and determining one or more of a range of motion, a magnitude of motion, or a direction of movement of the knee based on the measured movement of the first and second adherent sensors and the determined orientations of the first and second sensors relative to the direction and extension of the knee. In some embodiments, the stretching or contraction of the one or more sensors is in a direction, 1106 in FIG. 11, or perpendicular to a current direction of flexion and extension of the joint, 1105 in FIG. 11. In some embodiments, the measurements of the first and second adherent sensors are calibrated against a baseline measurement performed by the medical professional; the calibration can include an offset or the generation of a positioning matrix for each sensor. In some embodiments, the local computing device can transfer and update the positioning matrix to a second set of sensors when the sensor requires replacing.

Local Computing Devices

In some embodiments, the systems and methods disclosed herein includes a local computing device. In some embodiments, the local computing device is a computing device of the subject, the patient, the user, or another user. In some embodiments, the subject, the patient, or the user is the person to whom the sensors are adhered. In some embodiments, another user is a medical professional.

In some embodiments, the local computing device herein includes one or more of an IoT device, a personal computer, a laptop computer, a tablet computer, a smart phone, a smart TV, a gaming console, a digital media player, a smart speaker, a smart home, a smart watch, a virtual reality (VR) or augmented reality (AR) goggle or glasses, a hub, a network operation server, a digital processing device, or a wearable computing device.

In some embodiments, the local computing device includes a digital processing device comprising: at least one processor, an operating system configured to perform executable instructions, a memory, and a computer program including instructions executable by the digital processing device to create an application comprising software modules. In some embodiments, the application is a web or mobile application.

Figure 10B:
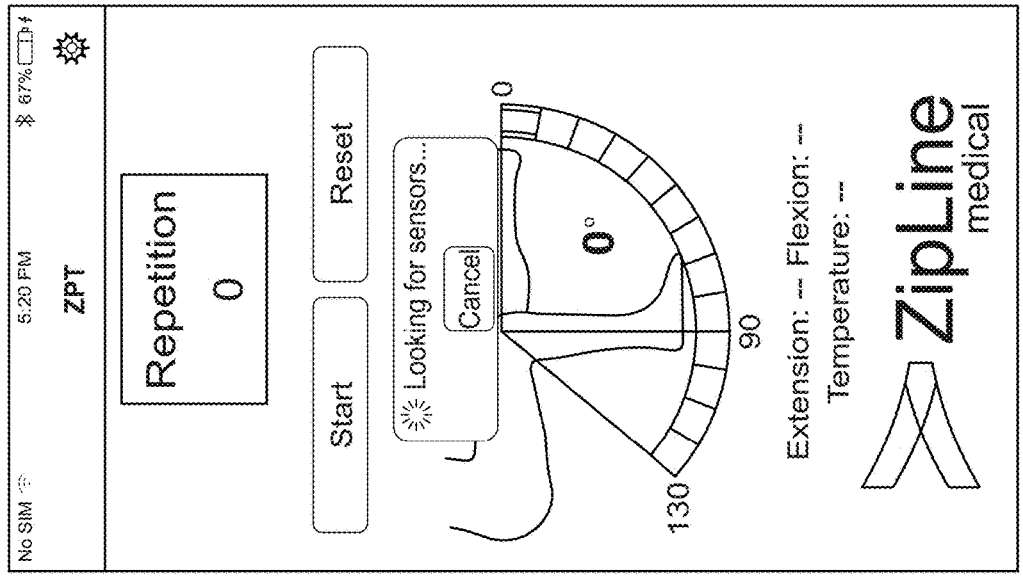
FIGS. 10A-10B show an exemplary embodiment of the systems and methods disclosed herein; in this case, a user interface that allows a user to start an application and couple the sensors to the application.
Figure 10A:
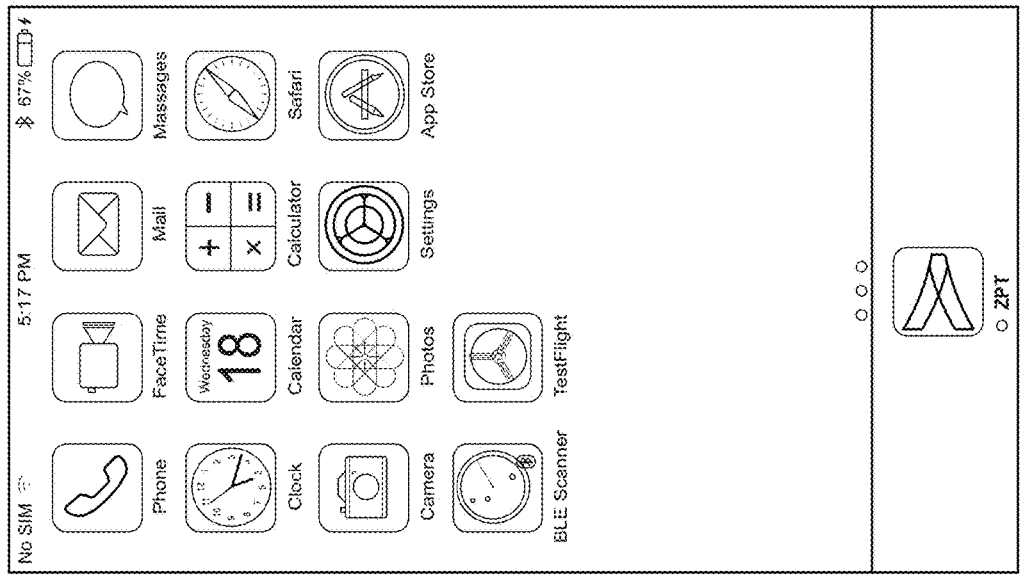

Referring to FIG. 10A, in a particular embodiment, the application is a mobile application. In some embodiments, the local computing device includes a communications element including a transmitter, receiver, and/or transceiver.

In some embodiments, the application of the local computing device allows a user to receive measurement data from the sensing assembly via a receiver or a transceiver. In some embodiments, the application allows a user to determine one or more parameters of the joint or the subject based the received measurement data. In some embodiments, the local computing device is configured to determine one or more of a range of motion of the joint, a range of flexion of the joint, a range of extension of the joint, a range of rotation of the joint, a motion pattern of the joint, a gait of the subject, a position of the joint, an orientation of the joint, a placement of the sensor(s) relative to the joint, a compliance of the subject to a joint cooling or heating protocol, a compliance of the subject to a movement protocol, a compliance of the subject for muscle activation/inactivation, swelling of the joint, inflammation of the joint, edema of the joint, mechanical or physical impact on the joint, treatment effect on the joint, or a physical therapy progress of the subject based on the received measurement data. Referring to FIG. 10B, in a particular embodiment, when the application starts or opens by the user, the application automatically locate and connect to the sensors that has been registered. In this particular embodiment, for first time use of the application, the application connects/couples to the first plurality of sensors it finds. In some embodiments, upon initialization, the application connects/couples to the first two sensors it finds. the In some embodiments, the application finds all sensors that meet a pre-selected criteria, for examples, proximity, with a detectable Bluetooth signal, and let the user selects the sensors to connect/couple. In some embodiments, the application registers all the sensors that the user selected and automatically couples to one or more of them in the future. In some embodiments, the user may select "cancel" when no sensor is required.

Figures 11, 12A:
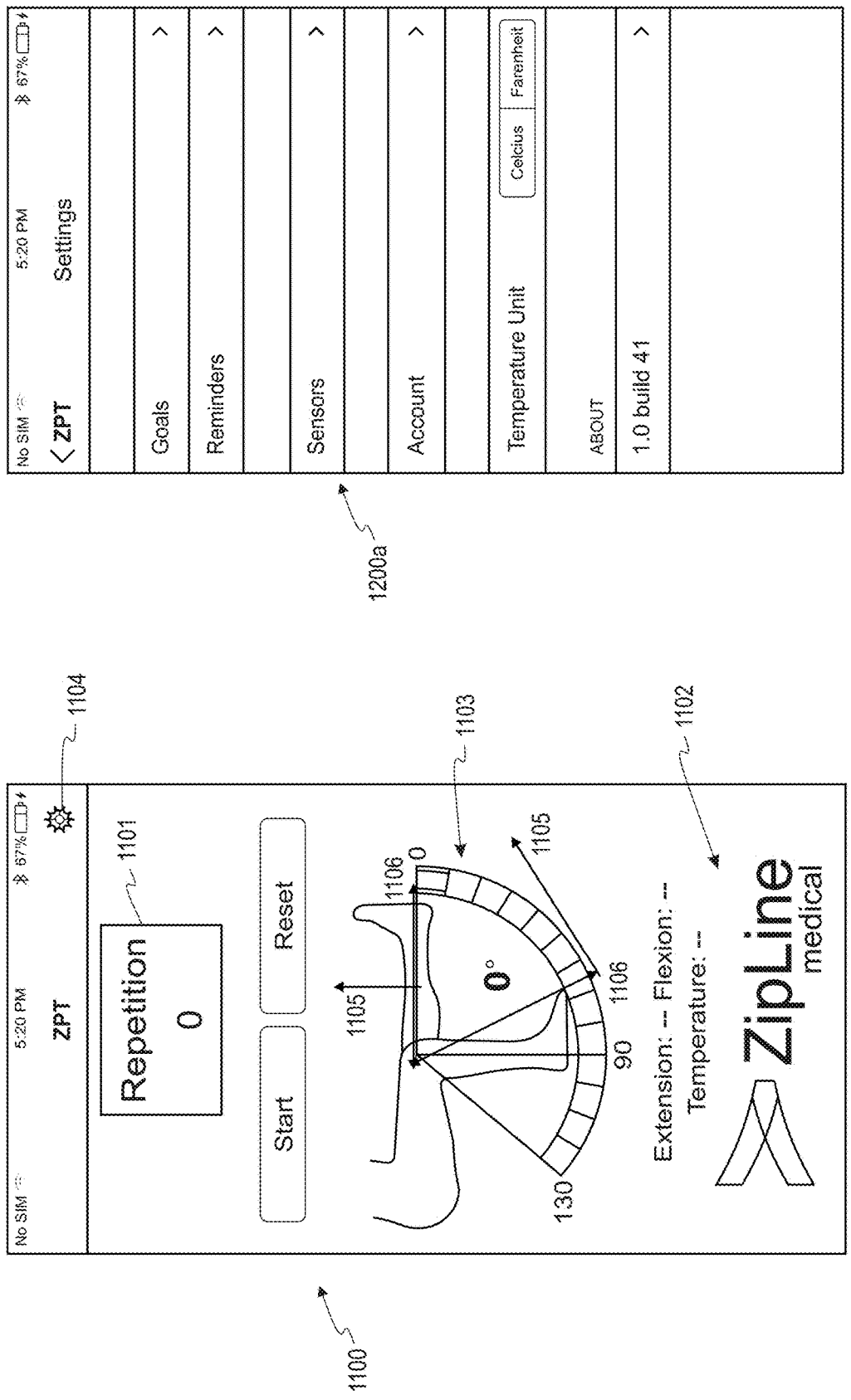
FIG. 11 shows an exemplary embodiment of the systems and methods disclosed herein; in this case, a user interface that allows a user to view range of motion measurements.
FIG. 12A shows an exemplary embodiment of the systems and methods disclosed herein; in this case, a user interface that allows a user to adjust settings.

Referring to FIGS. 2A and 11, in a particular embodiment, the systems and methods herein provide a user interface 200a and 1100, respectively, that allows a user to measure range of motion (ROM) and visualize the measurement data. In this embodiment, the user can interact with a "start" button and the application automatically record a number of repetitions 201, 1101 of flexion and extension, and for each flexion and extension, a flexion and an extension angle, respectively. In the same embodiment, the application also automatically analyzes and displays the maximum flexion angle and minimum extension angle 202, 203, 1102, 1103 based on the recorded number of repetitions. In this embodiment, the application records a current temperature 1102 measured by the sensor. In some embodiments, the application allows a user to review a picture and/or an animation 203, 1103 in real-time that indicate the current flexion and extension angle or the current maximum flexion angle and minimum extension angle. In the same embodiment, when the user interacts with a "stop" button, the application stops the recording, temporarily caches the recording, and/or sends the recorded data to the remote cloud storage. In some embodiments, the therapeutic protocol goal flexion and extension angles are presented to the user and audible and visual cues are provided when the goals are achieved. In some embodiments, the number of repetitions is automatically set in compliance with the therapeutic protocol. In some embodiments, history data that have not been collected from each sensor are automatically collected and sent to the remote cloud storage after the user interacts with the stop button. In some embodiments, the application prompts the user to select if he or she wants to send the most recent recording and/or history data after each recording.

Referring to FIG. 2B, in a particular embodiment, the application provides a user interface 200b to allow a user to visualize summary of progress based on recording for a pre-selected period of time, e.g., a day. In this particular embodiment, the visualization includes a picture and/or an animation 204 that indicates the maximum flexion angle and minimum extension angle during the pre-selected period of time. In this embodiment, the application allows a user to visualize repetitions REPS. In the same embodiment, the application allows a user to visualize suggested treatment or actions based on the measured and record summary of progress. Such suggested treatment is advantageous shown with a picture and/or animation 205 to indicate one or more period of time during a day that one or more treatment actions should be taken place. In this case, icing 206 is suggested to repeat three times a day, and elevation 206 is suggested to be taken place during most of the evening hours and some day-time hours.

Figure 2D:
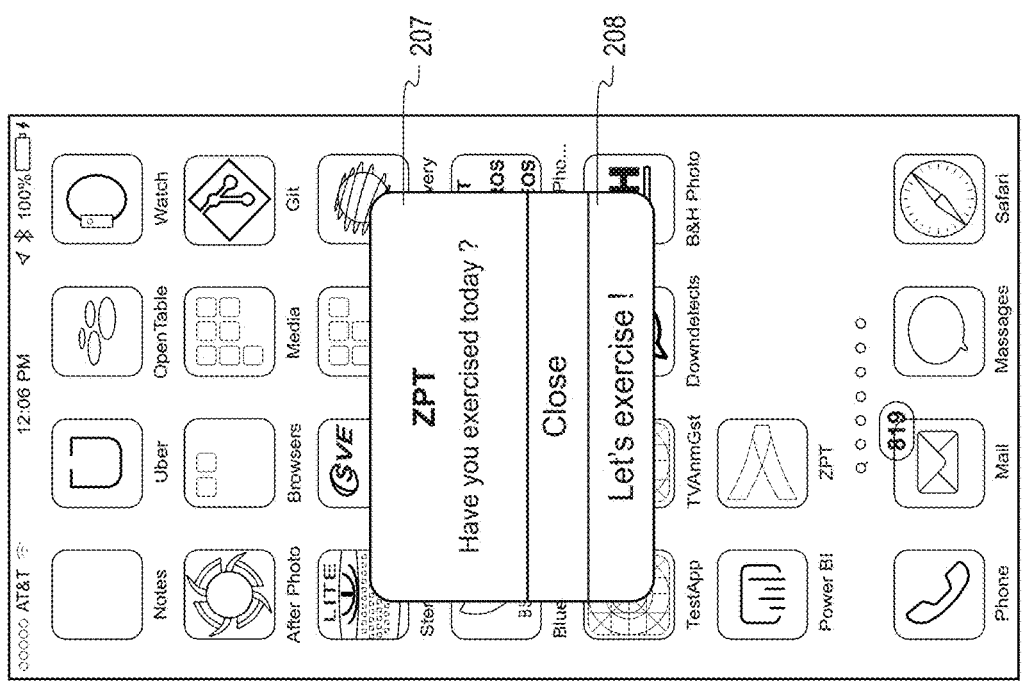
Figure 2C:
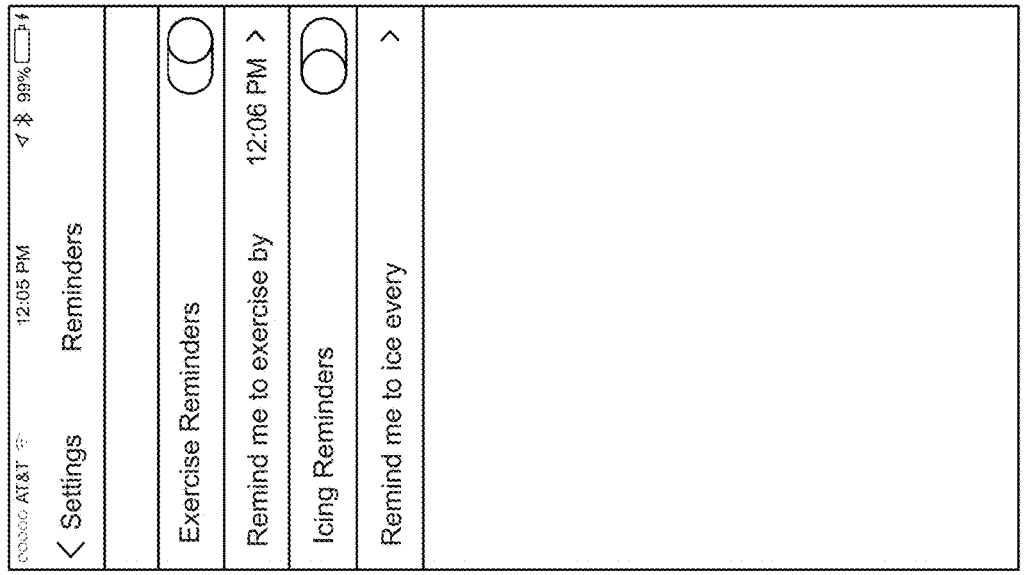

Referring to FIG. 2C, in a particular embodiment, the application provides the user the user interface 200c to visualize and adjust reminder settings. In this case, the user can set one or more reminders for different exercises so that the application sends a reminder before the schedule exercise(s) are to be started. In the same cases, the user can set icing reminders. In some embodiments, the user adjusts one or more different reminders based on information provided about his/her summary of progress and suggested treatment (s) or actions as in FIG. 2B.

Referring to FIG. 2D, in a particular embodiment, a pre-set or automatically generated reminder pops up at the user's mobile device. In some embodiments, the reminder includes a picture, a text message 207, a sound, a mechanical effect, and/or a link 208 that allows the user to start the application via interaction with the link.

Figures 12B, 12C:
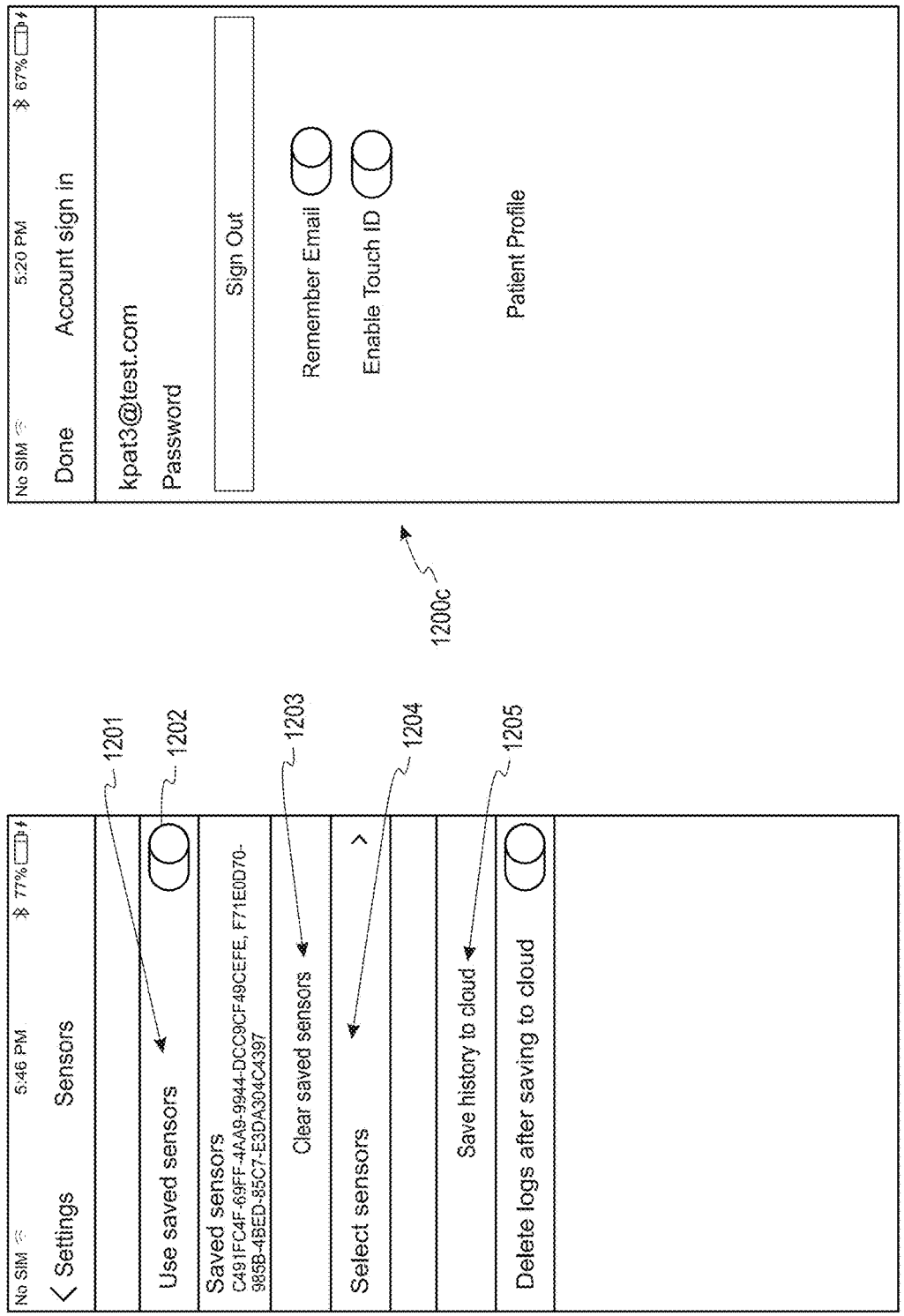
FIG. 12B shows an exemplary embodiment of the systems and methods disclosed herein; in this case, a user interface that allows a user to select sensor(s).
FIG. 12C shows an exemplary embodiment of the systems and methods disclosed herein; in this case, a user interface that allows a user to sign in to allow sensor data to be sent to a cloud service.

Referring to FIG. 12A, in a particular embodiment, the application provides a user interface 1200a to allow a user to adjust settings by interaction with the gear icon 1104 in FIG. 11, optionally on the top right corner of the user interface. In this embodiment, the application then provides a user interface that allows a user to visualize different settings. In this embodiment, the settings include one or more goals, one or more reminders, one or more selection of sensors, and account information management. For example, the user may set a reminder to perform knee flexion exercise and a different reminder to perform knee extension exercise. In some embodiments, if a user is rehabilitating both knees, the user may select the respective set of sensors to exercise a particular knee. Referring to FIG. 12B, in a particular embodiment, after a user select "sensor" in FIG. 12A, the application then provides a user interface 1200b that allows a user to visualize user-saved sensors 1201, each saved sensor with a unique identifier. In the same embodiments, the user can select one or more user-saved sensors to be on or off 1202 to ensure the correct sensors are connected to the application before a recording. If an incorrect sensor is connected, the user can press "clear saved sensors" 1203 and the application reconnect to sensors as if the user first uses the application and no sensors have been registered as in FIG. 10B. If the user knows the unique identifier of one or more sensor(s) that he or she wants to connect, the sensor can be selected from the "select sensor" 1204. In this particular embodiment, a selected sensor can signal a visual, audio, or mechanical signal to help identify the sensor and/or confirm sensor selection. In the same embodiment, current sensor selection and/or sensor selection history 1205 is temporarily cached in a log and transmitted to a remote storage.

Referring to FIG. 12C, in an embodiment, the user is provided with a user interface 1200c that allows the user to sign in to his or her. Signing-in in some cases is required for sensor data to be sent to remote cloud storage. In this embodiment, an email address is used as the login, once the password is confirmed, the touch ID of the mobile device can be used to re-login therefore the initial login is the only time required for the user to manually login.

In some embodiments, the application of the local computing device allows a user to send control data to the sensing assembly via a transmitter or a transceiver. In some embodiments, the control data is based on the measurement data received.

In some embodiments, the local computing device or the remote computing device is configured to determine placements and orientations of the sensor(s) relative to the joint adjacent response and determine one or more of a range of motion of the joint, a range of flexion of the joint, a range of extension of the joint, a range of rotation of the joint, a motion pattern of the joint, a gait of the subject, a position of the joint, or an orientation of the joint based on the determined placement and orientations of the sensor(s) relative to the joint. In some embodiments, the motion, flexion, extension, rotation, position or orientation is two dimensional or three dimensional.

In some embodiments, the local computing device disclosed herein is a computing device for the subject. In some embodiments, the local computing device includes a user interface, a communications element and a digital processing device configured to: passively receive or actively pull measurement data from one or more sensors coupled to the joint via the communications element, store the received measurement data, receive input from the subject through the user interface, transmit the received measurement data and received input to a remote computing device via the communications element, receive one or more of an analysis of the transmitted measurement data and received input or a treatment regimen from the remote computing device via the communication element, and provide one or more of the received analysis or treatment regimen to the subject at the user interface. In some embodiments, the communications element includes a transmitter, a receiver, and/or a transceiver. In some embodiments, the digital processing device is further configured to authenticate the one or more sensors prior to coupling to the one or more sensors to receive the measurement data. In some embodiments, digital processing device is further configured to locate one or more sensors prior to coupling to the one or more sensors. In some embodiments, the digital processing device is further configured to authenticate the subject through the user interface prior to receiving the input from the subject. In some embodiments, the digital processing device is further configured to set a sampling interval for receiving the measurement data from the one or more sensors. In some embodiments, the digital processing device is further configured to set a transmission interval for transmitting the measurement data to the remote computing device. In some embodiments, the sampling interval or the transmission interval is fixed. In some embodiments, the sampling interval or the transmission interval is in the range of about 10 minutes to about 24 hours. In some embodiment, the sampling is automatically or manually started after a user finishes a new section so that there is measurement data at the sensor(s) haven't transmitted to the local computing device. In some embodiments, the digital processing device is configured to provide one or more of the received analysis or the treatment regimen by providing one or more of an alarm, a notification, a reminder, a goal, a summary of progress, or a communication interface with a medical professional to the subject. In some embodiments, providing the one or more of the received analysis or the treatment regimen includes provide a visual, sound, or mechanical signal. In some embodiments, the visual signal includes a picture, a color, an animation, a link, an interactive media, or the like. In some embodiments, the digital processing device is further configured to generate a real-time analysis of the received measurement data. In some embodiments, the digital processing device is configured to transmit the real-time analysis to one or more of the remote computing device or a computing device of a medical practitioner. In some embodiments, the digital processing device is configured to display the real-time analysis to the subject through the user interface, for example, as in FIG. 2B. In some embodiments, the real-time analysis comprises one or more of a range of motion of the joint, a temperature of the joint, or an elevation of the joint. In some embodiments, the input from the subject comprises one or more of: sensor related information, physical treatment related information, a recorded physical treatment event, a self-diagnosis, a symptom, a drug, a progression in a therapeutic protocol or treatment protocol, a medical history, feedback about a current or previous treatment protocol, feedback about a previous surgical operation, or feedback on the current or previous treatment protocol. In some embodiments, the real-time analysis includes one or more of a range of motion of the joint, a range of flexion of the joint, a range of extension of the joint, a range of rotation of the joint, a motion pattern of the joint, a gait of the subject, a position of the joint, or an orientation of the joint based on the determined placement and orientations of the sensor(s) relative to the joint. In some embodiments, the motion, flexion, extension, rotation, position or orientation is two dimensional or three dimensional.

Referring to FIG. 1, in some embodiments, the local computing device 102 may allow the patient to access the web portal 104 of the backend remote computing device 104*a* directly without accessing the patient's application 108. In some embodiments, the local computing device 102 may allow the patient to access a third party web portal (not shown) 110 via the API 104*b* optionally provided at the backend remote computing device 104.

In some embodiments, the systems and methods herein include a computing device for a medical professional for monitoring the subject, the computing device comprising a user interface and a digital processing device configured to: provide measurement data of the subject to the medical practitioner through the user interface, the measurement data being received from a remote computing device and originating from one or more sensors coupled to the joint to measure the measurement data and transmit the measurement data to the remote computing device; providing input from the subject to the medical practitioner through the user interface, the input being received from a local computing device of the subject via a communications element; receiving an analysis of one or more of the measurement data or subject input from the medical professional through the user interface; receiving a treatment regimen from the medical professional through the user interface, and transmitting one or more of the received analysis or received treatment regimen to the remote computing device, the remote computing device transmitting the one or more of the received analysis or received treatment regimen to the local computing device of the subject. In some embodiments, the user interface is a two-way communication interface between the medical professional and the subject. In some embodiments, the measurement data is provided to the medical practitioner in real-time. In some embodiments, the digital processing device is further configured to authenticate the medical professional through the user interface prior to receiving the input from the subject. In some embodiments, the digital processing device is further configured to set a sampling interval for receiving the measurement data from the one or more sensors. In some embodiments, the digital processing device is further configured to set a transmission interval for the local computing device of the subject to transmit the measurement data. In some embodiments, one or more of the analysis of the one or more of the measurement data or the subject input or treatment regimen is generated by the medical professional based at least partially on an automated analysis of one or more of the measurement data or the subject input. In some embodiments, the automated analysis is generated by the digital processing device. In some embodiments, the automated analysis is generated by the remote computing device and provided therefrom. In some embodiments, the analysis of the measurement data is automatically generated by the local computing device, optionally after receiving the measurement data. In some embodiments, the digital processing device is further configured to generate a real-time analysis of the received measurement data. In some embodiments, the digital processing device is configured to display the real-time analysis to the medical professional through the user interface. In some embodiments, the real-time analysis comprises one or more of a range of motion of the joint, a temperature of the joint, or an elevation of the joint. In some embodiments, the digital processing device is further configured to generate a progress report for the subject and the user interface is configured to display the progress report to the medical professional.

Referring to FIG. 1, in some embodiments, the local computing device 105 for the medical practitioner may allow the practitioner to access the web portal 104 of the backend remote computing device 104*a* directly without accessing the practitioner's application 113. In some embodiments, the local computing device 105 may allow the practitioner to access a third party web portal (not shown) 115 via the API 104*b* optionally provided at the backend remote computing device 104.

Figure 3A:
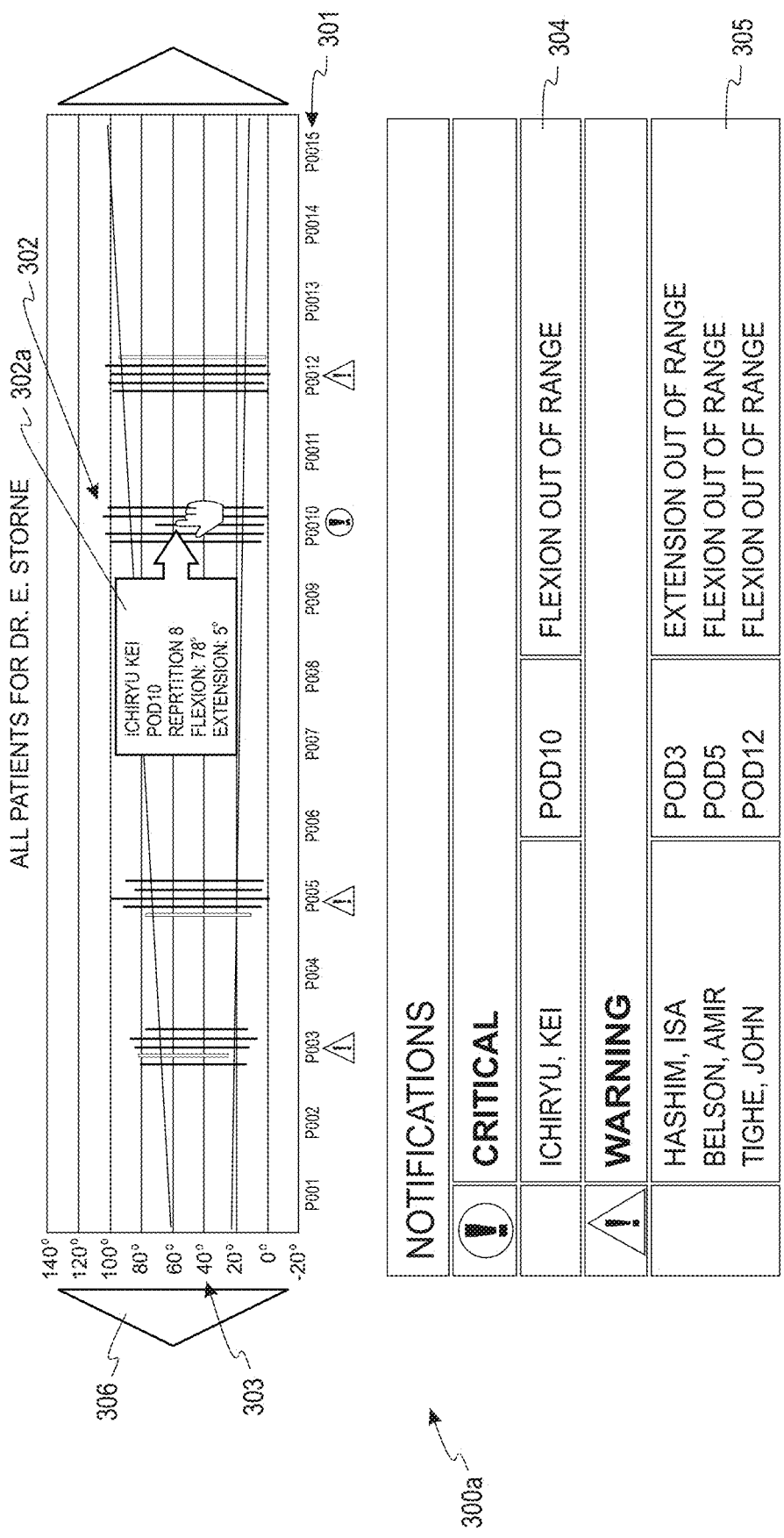
FIGS. 3A-3B show an exemplary embodiment of a mobile application of the systems and methods disclosed herein; in this case, a user interface that allows a medical professional to review and manage patients' progress monitored using the systems and methods herein.

Referring to FIG. 3A, in a particular embodiment, a user interface 300*a* is provided to a doctor, physician, or other medical practitioner for reviewing summary of his patients' progress. In this embodiment, each patient is given a unique patient identifier 301, and the patient's maximum flexion angles and minimum extension angles for each day is shown 302. The vertical axis 303 shows different flexion and extension angles. In the same embodiments, the patient's progress is color coded based on pre-set rules by the doctor, physician, or other medical practitioner, optionally customized for each patient according to the patient's medical history. Hence, the doctor, physician, or other medical practitioner can conveniently and easily detect any warnings or critical events regarding one or more of his patients. In some embodiments, real-time notification is sent to the doctor, physician, or other medical practitioner, when a warning 305 or a critical event 305 is detected. In this embodiment, the notifications 304, 305 are optionally displayed at the same user interface to the doctor, physician, or other medical practitioner. The doctor, physician, or other medical practitioner interacts with a color coded event 302 of one of his patient to review further details 302a of the patient and the details, such as the maximum flexion and minimum extension angles. In this embodiment, the doctor, physician, or other medical practitioner can also interact with the big arrows 306 to browse more patients' summary of progress.

Figure 3B:
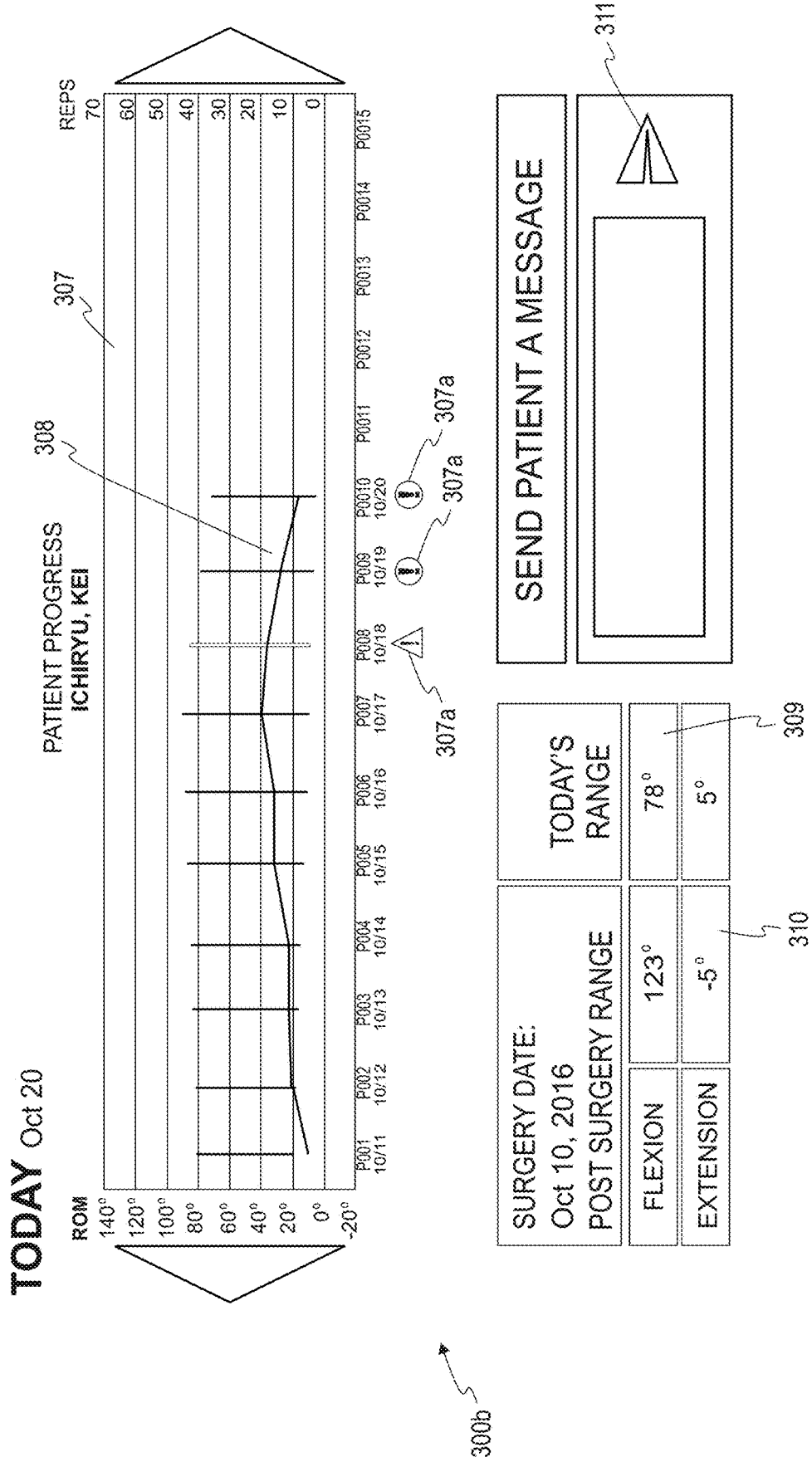

Referring to FIG. 3B, in a particular embodiment, the user interface 300b may allow the user to interact with the patient's unique identifier, the detailed summary 302 or 302a, to further review the patient's detailed information and progress. In this embodiment, the patient's ranges of motion 307 and number of repetitions of exercises 308 on different dates following the patient's operation on October 10 are displayed and color-coded with specific warning signs 307a and the doctor, physician, or other medical practitioner can clearly identify the warning and critical events on the last three dates in the patient's summary. In this embodiment, the doctor, physician, or other medical practitioner is allowed to view this patient's operation date and a suggested or measured range of motion for this patient 310 in comparison with the current range of motion of the patient 309. The doctor, physician, or other medical practitioner, in this embodiment, is provided with an interface that allows his to send a message to the patient 311. In some embodiments, the current range of motion is provided to the user interface for the subject and/or to the sensors themselves, and alerts, such as audio or visual alerts, can be provided to subject with the subject's mobile device and/or the sensors themselves if the range is exceed or close to being exceeded. In some embodiments where the sensor includes a temperature sensor, the sensor assembly could be programmed to alert on increased temp, which may indicate inflammation or infection.

In some embodiments, the local computing device for the subject, the local computing device for the medical professional or the remote computing device herein includes a mobile application provided to a digital processing device, for example, a mobile device. In some embodiments, the mobile application is provided to a mobile digital processing device at the time it is manufactured. In other embodiments, the mobile application is provided to a mobile digital processing device via the computer network described herein.

In view of the disclosure provided herein, a mobile application is created by techniques known to those of skill in the art using hardware, languages, and development environments known to the art. Those of skill in the art will recognize that mobile applications are written in several languages. Suitable programming languages include, by way of non-limiting examples, C, C++, C #, Objective-C, Swift, Java™, Javascript, Pascal, Object Pascal, Python™, Ruby, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Android Studio, Celsius, B4X, Bedrock, Flash Lite, .NET Compact Framework, Rhomobile, Visual Studio, WorkLight Mobile Platform, Xamarin, and Xcode. Other development environments are available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Those of skill in the art will recognize that several commercial forums are available for distribution of mobile applications including, by way of non-limiting examples, Apple® App Store, Google® Play, Chrome WebStore, BlackBerry® App World, App Store for Palm devices, App Catalog for webOS, Windows® Marketplace for Mobile, Ovi Store for Nokia® devices, Samsung® Apps, and Nintendo® DSi Shop.

Remote Computing Devices

Figure 13:
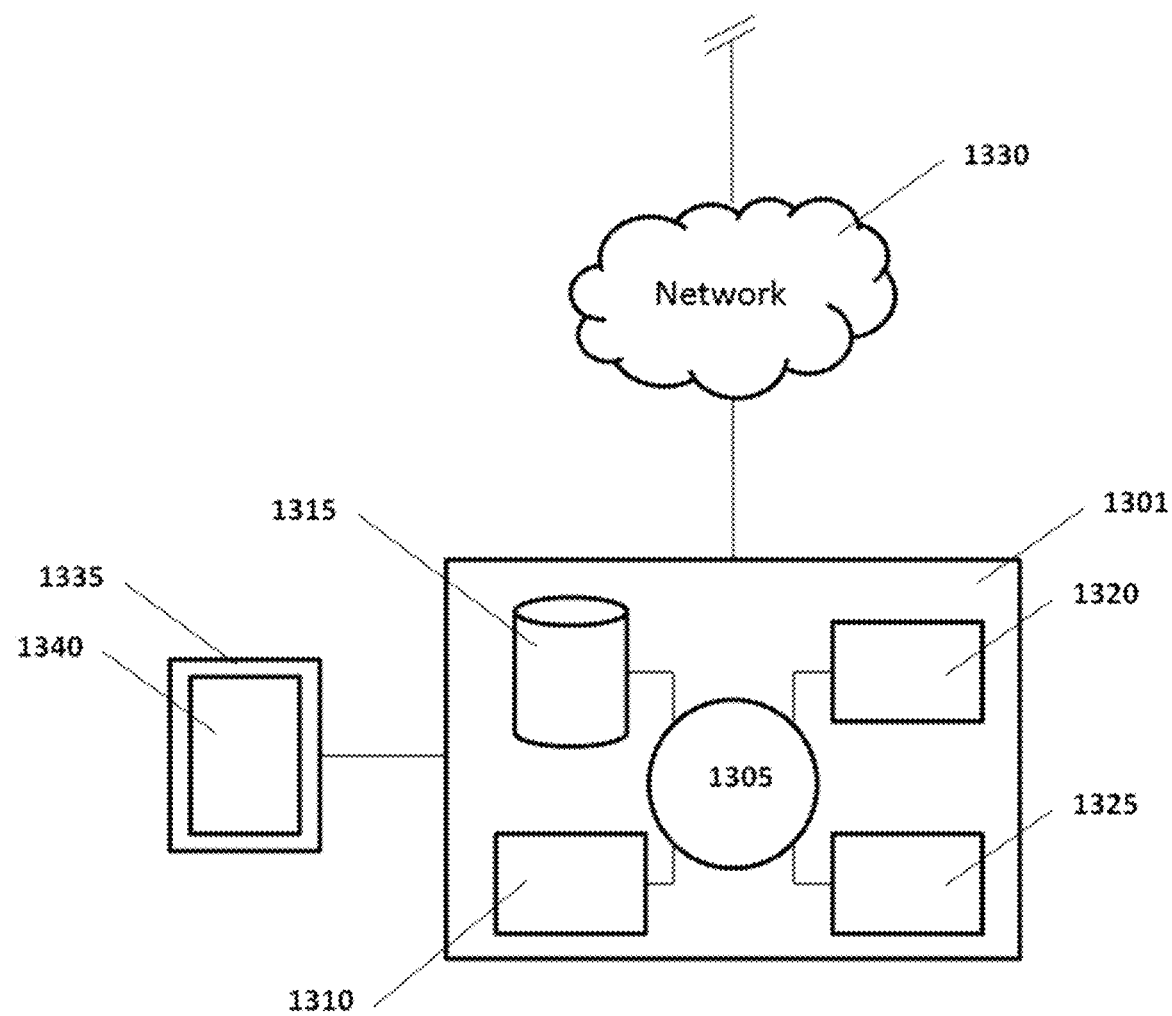
FIG. 13 shows a non-limiting schematic diagram of a digital processing device; in this case, a device with one or more CPUs, a memory, a communication interface, and a display.

In some embodiments, the systems or methods disclosed herein include a remote computing device. Non-limiting exemplary embodiments of the remote computing device are shown in FIGS. 1, 13. In some embodiments, the remote computing device includes one or more of an IoT device, a hub, a network operation server, a workstation, a personal computer, a laptop computer, a tablet computer, a smart phone, a smart TV, a gaming console, a digital media player, a smart speaker, a smart home, a smart watch, a VR/AR goggle or glasses, a digital processing device, or a wearable computing device.

In some embodiments, the remote computing device includes a web application, a web portal, a mobile application a software module, a computer program, or the like that is executable by the computing device, for example, web portal 104a in FIG. 1. In some embodiments, the local or remote computing device includes a digital processing device comprising: at least one processor, an operating system configured to perform executable instructions, a memory, and a computer program including instructions executable by the digital processing device to create an application comprising software modules. In some embodiments, the application is a web or mobile application. In some embodiments, the remote computing device includes a database. In some embodiments, the remote computing device includes a communications element, a transmitter, receiver, and/or transceiver. In some embodiments, the remote computing device includes an application programming interface (API), for example, 104b in FIG. 1.

In some embodiments, the remote computing device is configured to determine one or more of a range of motion of the joint, a range of flexion of the joint, a range of extension of the joint, a range of rotation of the joint, a motion pattern of the joint, a gait of the subject, a position of the joint, an orientation of the joint, a placement of the sensor(s) relative to the joint, a compliance of the subject to a joint cooling or heating protocol, a compliance of the subject to a movement protocol, a compliance of the subject for muscle activation/ inactivation, swelling of the joint, inflammation of the joint, edema of the joint, mechanical or physical impact on the joint, treatment effect on the joint, or a physical therapy progress of the subject based on the received measurement data.

In some embodiments, the local computing device or the remote computing device is configured to determine placements and orientations of the sensor(s) relative to the joint adjacent response and determine one or more of a range of motion of the joint, a range of flexion of the joint, a range of extension of the joint, a range of rotation of the joint, a motion pattern of the joint, a gait of the subject, a position of the joint, or an orientation of the joint based on the determined placement and orientations of the sensor(s) relative to the joint.

In some embodiments, the analysis of the measurement data is automatically generated by the remote computing device. In some embodiments, the analysis of the measurement data is automatically generated by the local computing device.

In some embodiments, the systems or methods disclosed herein includes a medical professional computing device in communication with the remote computing device or the local computing device to access one or more of the measurement data or at least a first portion of the analysis, and wherein at least a second portion of the analysis of the measurement data is provided by the medical professional through the medical professional computing device.

In some embodiments, the medical professional computing device comprises one or more of an IoT device, a hub, a network operation server, a workstation, a personal computer, a laptop computer, a tablet computer, a smart phone, a smart TV, a gaming console, a digital media player, a smart speaker, a smart home, a smart watch, a VR/AR goggle or glasses, a digital processing device, or a wearable computing device.

In some embodiments, the local computing device is configured to provide the analysis to the subject via one or more of an audio user interface or a video user interface of the local computing device. In some embodiments, the local computing device is configured to further provide one or more of a reminder, an alarm, a tip, an insight, or an instruction to the subject. In some embodiments, the local computing device is configured to further receive input from the subject and transmit the received input to the remote computing device. In some embodiments, the input comprises one or more of a self-diagnosis parameter, a progress of a physical therapy protocol, a compliance to a physical therapy protocol, or a biometric parameter of the subject.

In some embodiments, the systems or methods disclosed herein include a remote computing device in communication with local computing devices for both the subject and a medical professional monitoring the subject via a communications element. In some embodiments, the remote computing device includes a digital processing device (equivalently as a digital processing device herein) and configured to perform one or more of the following: receive measurement data from the local computing device of the subject, the measurement data originating from one or more sensors coupled to the joint to measure the measurement data and transmit the measurement data to the local computing device, receive input(s) from the subject from the local computing device of the subject, store one or more of the received measurement data or received input in a database, generate an analysis of one or more of the received measurement data or received input from the subject, generating a treatment regimen based on one or more of the received measurement data or received input from the subject, and transmit one or more of the generated analysis or generated treatment regimen to one or more of the local computing device of the subject or the local computing device of the medical professional. In some embodiments, the remote computing device is configured to provide to one or more of the subject or the medical professional access thereto through a user interface. In some embodiments, the user interface comprises a web portal. In some embodiments, the web portal includes a web application, a mobile application, a software module, a computer program disclosed herein. In some embodiments, the digital processing device is configured authenticate the one or more of the subject or the medical professional prior to providing the access. In some embodiments, the digital processing device is configured to generate the treatment regimen by selecting select the treatment regimen from a plurality of treatment regimens stored in a database based on one or more of the received measurement data or received input. In some embodiments, the digital processing device is configured to generate one or more of the analysis or the treatment regimen by transmitting one or more of the measurement data or the input from the subject to the medical practitioner and receiving an input from the medical practitioner in response. In some embodiments, one or more of the analysis of the one or more of the measurement data or the subject input or treatment regimen is generated by the medical professional based at least partially on an automated analysis of one or more of the measurement data or the subject input. In some embodiments, the automated analysis is generated by the processor. In some embodiments, the digital processing device is configured to provide an intermediary for two-way communication between the medical professional and the subject. In some embodiments, the digital processing device is further configured to set a sampling interval for receiving the measurement data from the one or more sensors. In some embodiments, the digital processing device is further configured to set a transmission interval for the local computing device of the subject to transmit the measurement data.

In some embodiments, the systems or methods disclosed herein may be integrated with an incision closure device, for example, as described in details in U.S. Pat. Nos. 8,323,313, 9,050,086, 9,089,328, 9,474,529, 9,554,799, 9,544,800, 9,561,034, and 9,642,621 and U.S. patent application Ser. Nos. 13/665,160 and 15/369,293, which are incorporated herein. In some embodiments, the sensor assembly, pouch, or both may be detachably integrated with the incision closure device so that when the closure device is removed from the patient the sensor could stay on the patient. In some embodiments, the sensor assembly may detect whether it is being used in conjunction with such closure devices and may communicate this to a local and/or remote computing device. An application on the local and/or remote computing device may also concurrently track the use of wound closure devices and the progress of wound or incision healing.

Digital Processing Device

In some embodiments, the platforms, systems, media, and methods described herein include a digital processing device or use of the same. In some embodiments, the local computing device for the subject, the local computing device for the medical professional, and/or the remote computing device herein includes a digital processing device. In further embodiments, the digital processing device includes one or more hardware central processing units (CPUs) or general purpose graphics processing units (GPGPUs) that carry out the device's functions. In still further embodiments, the digital processing device further comprises an operating system configured to perform executable instructions. In some embodiments, the digital processing device is optionally connected to a computer network. In further embodiments, the digital processing device is optionally connected to the Internet such that it accesses the World Wide Web. In still further embodiments, the digital processing device is optionally connected to a cloud computing infrastructure. In other embodiments, the digital processing device is optionally connected to an intranet. In other embodiments, the digital processing device is optionally connected to a data storage device.

In accordance with the description herein, suitable digital processing devices include, by way of non-limiting examples, server computers, desktop computers, laptop computers, notebook computers, sub-notebook computers, netbook computers, netpad computers, set-top computers, media streaming devices, handheld computers, Internet appliances, mobile smartphones, tablet computers, personal digital assistants, video game consoles, and vehicles. Those of skill in the art will recognize that many smartphones are suitable for use in the system described herein. Those of skill in the art will also recognize that select televisions, video players, and digital music players with optional computer network connectivity are suitable for use in the system described herein. Suitable tablet computers include those with booklet, slate, and convertible configurations, known to those of skill in the art.

In some embodiments, the digital processing device includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X/macOS, UNIX®, and UNIX-like operating systems such as GNU/Linux®. In some embodiments, the operating system is provided by cloud computing. Those of skill in the arts will also recognize that suitable cloud computing include, by way of non-limiting examples, Amazon AWS, Google Cloud, Microsoft Azure. Those of skill in the art will also recognize that suitable mobile smart phone operating systems include, by way of non-limiting examples, Nokia® Symbian OS, Apple iOS®, Research In Motion® BlackBerry OS®, Google® Android®, Microsoft® Windows Phone® OS, Microsoft® Windows Mobile® OS, Linux®, and Palm® WebOS®. Those of skill in the art will also recognize that suitable media streaming device operating systems include, by way of non-limiting examples, Apple TV®, Roku®, Boxee®, Google TV®, Google Chromecast®, Amazon Fire®, and Samsung® HomeSync®. Those of skill in the art will also recognize that suitable video game console operating systems include, by way of non-limiting examples, Sony® PS3®, Sony® PS4®, Microsoft® Xbox 360®, Microsoft Xbox One, Nintendo Wii®, Nintendo® Wii U®, and Ouya®.

In some embodiments, the device includes a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In other embodiments, the device is a storage device including, by way of non-limiting examples, CD-ROMs, DVDs, flash memory devices, magnetic disk drives, magnetic tapes drives, optical disk drives, and cloud computing based storage. In further embodiments, the storage and/or memory device is a combination of devices such as those disclosed herein.

In some embodiments, the digital processing device includes a display to send visual information to a user. In some embodiments, the display is a liquid crystal display (LCD). In further embodiments, the display is a thin film transistor liquid crystal display (TFT-LCD). In some embodiments, the display is an organic light emitting diode (OLED) display. In various further embodiments, on OLED display is a passive-matrix OLED (PMOLED) or active-matrix OLED (AMOLED) display. In some embodiments, the display is a plasma display. In other embodiments, the display is a video projector. In yet other embodiments, the display is a head-mounted display in communication with the digital processing device, such as a VR headset. In further embodiments, suitable VR headsets include, by way of non-limiting examples, HTC Vive, Oculus Rift, Samsung Gear VR, Microsoft HoloLens, Razer OSVR, FOVE VR, Zeiss VR One, Avegant Glyph, Freefly VR headset, and the like. In still further embodiments, the display is a combination of devices such as those disclosed herein.

In some embodiments, the digital processing device includes an input device to receive information from a user. In some embodiments, the input device is a keyboard. In some embodiments, the input device is a pointing device including, by way of non-limiting examples, a mouse, trackball, track pad, joystick, game controller, or stylus. In some embodiments, the input device is a touch screen or a multi-touch screen. In other embodiments, the input device is a microphone to capture voice or other sound input. In other embodiments, the input device is a video camera or other sensor to capture motion or visual input. In further embodiments, the input device is a Kinect, Leap Motion, or the like. In still further embodiments, the input device is a combination of devices such as those disclosed herein.

Referring to FIG. 13, in a particular embodiment, an exemplary digital processing device 1301 is programmed or otherwise configured to receive measurement data from a local computing device of the subject, analyze measurement data, store measurement, transmit analysis to the local computing device of the subject and local computing device of the medical professional, and receive analysis from the local computing device of the medical professional. The device 1301 can regulate various aspects of transfer of the measurement data, analysis of the measurement data, and storage of the measurement data, of the present disclosure. In this embodiment, the digital processing device 1301 includes a central processing unit (CPU, also "processor" and "computer processor" herein) 1305, which can be a single core or multi core processor, or a plurality of processors for parallel processing. The digital processing device 1301 also includes memory or memory location 1310 (e.g., random-access memory, read-only memory, flash memory), electronic storage unit 1315 (e.g., hard disk), communication interface 1320 (e.g., network adapter) for communicating with one or more other systems, and peripheral devices 1325, such as cache, other memory, data storage and/or electronic display adapters. The memory 1310, storage unit 1315, interface 1320 and peripheral devices 1325 are in communication with the CPU 1305 through a communication bus (solid lines), such as a motherboard. The storage unit 1315 can be a data storage unit (or data repository) for storing data. The digital processing device 1301 can be operatively coupled to a computer network ("network") 1330 with the aid of the communication interface 1320. The network 1330 can be the Internet, an internet and/or extranet, or an intranet and/or extranet that is in communication with the Internet. The network 1330 in some cases is a telecommunication and/or data network. The network 1330 can include one or more computer servers, which can enable distributed computing, such as cloud computing. The network 130, in some cases with the aid of the device 1301, can implement a peer-to-peer network, which may enable devices coupled to the device 101 to behave as a client or a server.

Continuing to refer to FIG. 13, the CPU 1305 can execute a sequence of machine-readable instructions, which can be embodied in a program or software. The instructions may be stored in a memory location, such as the memory 1310. The instructions can be directed to the CPU 1305, which can subsequently program or otherwise configure the CPU 1305 to implement methods of the present disclosure. Examples of operations performed by the CPU 1305 can include fetch, decode, execute, and write back. The CPU 1305 can be part of a circuit, such as an integrated circuit. One or more other components of the device 1301 can be included in the circuit. In some cases, the circuit is an application specific integrated circuit (ASIC) or a field programmable gate array (FPGA).

Continuing to refer to FIG. 13, the storage unit 1315 can store files, such as drivers, libraries and saved programs. The storage unit 1315 can store user data, e.g., user preferences and user programs. The digital processing device 1301 in some cases can include one or more additional data storage units that are external, such as located on a remote server that is in communication through an intranet or the Internet.

Continuing to refer to FIG. 13, the digital processing device 1301 can communicate with one or more remote computer systems through the network 1330. For instance, the device 1301 can communicate with a remote computer system of a user. Examples of remote computer systems include personal computers (e.g., portable PC), slate or tablet PCs (e.g., Apple® iPad, Samsung® Galaxy Tab), telephones, Smart phones (e.g., Apple® iPhone, Android-enabled device, Blackberry®), or personal digital assistants.

Methods as described herein can be implemented by way of machine (e.g., computer processor) executable code stored on an electronic storage location of the digital processing device 1301, such as, for example, on the memory 1310 or electronic storage unit 1315. The machine executable or machine readable code can be provided in the form of software. During use, the code can be executed by the processor 1305. In some cases, the code can be retrieved from the storage unit 1315 and stored on the memory 1310 for ready access by the processor 1305. In some situations, the electronic storage unit 1315 can be precluded, and machine-executable instructions are stored on memory 1310.

Non-Transitory Computer Readable Storage Medium

In some embodiments, the systems and methods disclosed herein include one or more non-transitory computer readable storage media encoded with a program including instructions executable by the operating system of an optionally networked digital processing device. In some embodiments, the local computing device for the subject, for the medical practitioner and/or the remote computing device includes one or more non-transitory computer readable storage media. In further embodiments, a computer readable storage medium is a tangible component of a digital processing device. In still further embodiments, a computer readable storage medium is optionally removable from a digital processing device. In some embodiments, a computer readable storage medium includes, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media.

Web Application

In some embodiments, the local computing device for the subject, the local computing device for the medical professional or the remote computing device herein includes a web application, a web portal, or use of the same. In light of the disclosure provided herein, those of skill in the art will recognize that a web application, in various embodiments, utilizes one or more software frameworks and one or more database systems. In some embodiments, a web application is created upon a software framework such as Microsoft® .NET, Bootstrap, and/or Ruby on Rails (RoR). In some embodiments, a web application utilizes one or more database systems including, by way of non-limiting examples, relational, non-relational, object oriented, associative, and XML database systems. In further embodiments, suitable relational database systems include, by way of non-limiting examples, Microsoft® SQL Server, mySQL™, and Oracle®. Those of skill in the art will also recognize that a web application, in various embodiments, is written in one or more versions of one or more languages. A web application may be written in one or more markup languages, presentation definition languages, client-side scripting languages, server-side coding languages, database query languages, or combinations thereof. In some embodiments, a web application is written to some extent in a markup language such as Hypertext Markup Language (HTML), Extensible Hypertext Markup Language (XHTML), or eXtensible Markup Language (XML). In some embodiments, a web application is written to some extent in a presentation definition language such as Cascading Style Sheets (CSS). In some embodiments, a web application is written to some extent in a client-side scripting language such as Asynchronous Javascript and XML (AJAX), Flash® Actionscript, Javascript, or Silverlight®. In some embodiments, a web application is written to some extent in a server-side coding language such as Active Server Pages (ASP), ColdFusion®, Perl, Java™ JavaServer Pages (JSP), Hypertext Preprocessor (PHP), Python™, Ruby, Tcl, Smalltalk, WebDNA®, or Groovy. In some embodiments, a web application is written to some extent in a database query language such as Structured Query Language (SQL). In some embodiments, a web application integrates enterprise server products such as IBM® Lotus Domino®. In some embodiments, a web application includes a media player element. In various further embodiments, a media player element utilizes one or more of many suitable multimedia technologies including, by way of non-limiting examples, Adobe® Flash®, HTML 5, Apple® QuickTime®, Microsoft® Silverlight®, Java™, and Unity®.

Figure 14:
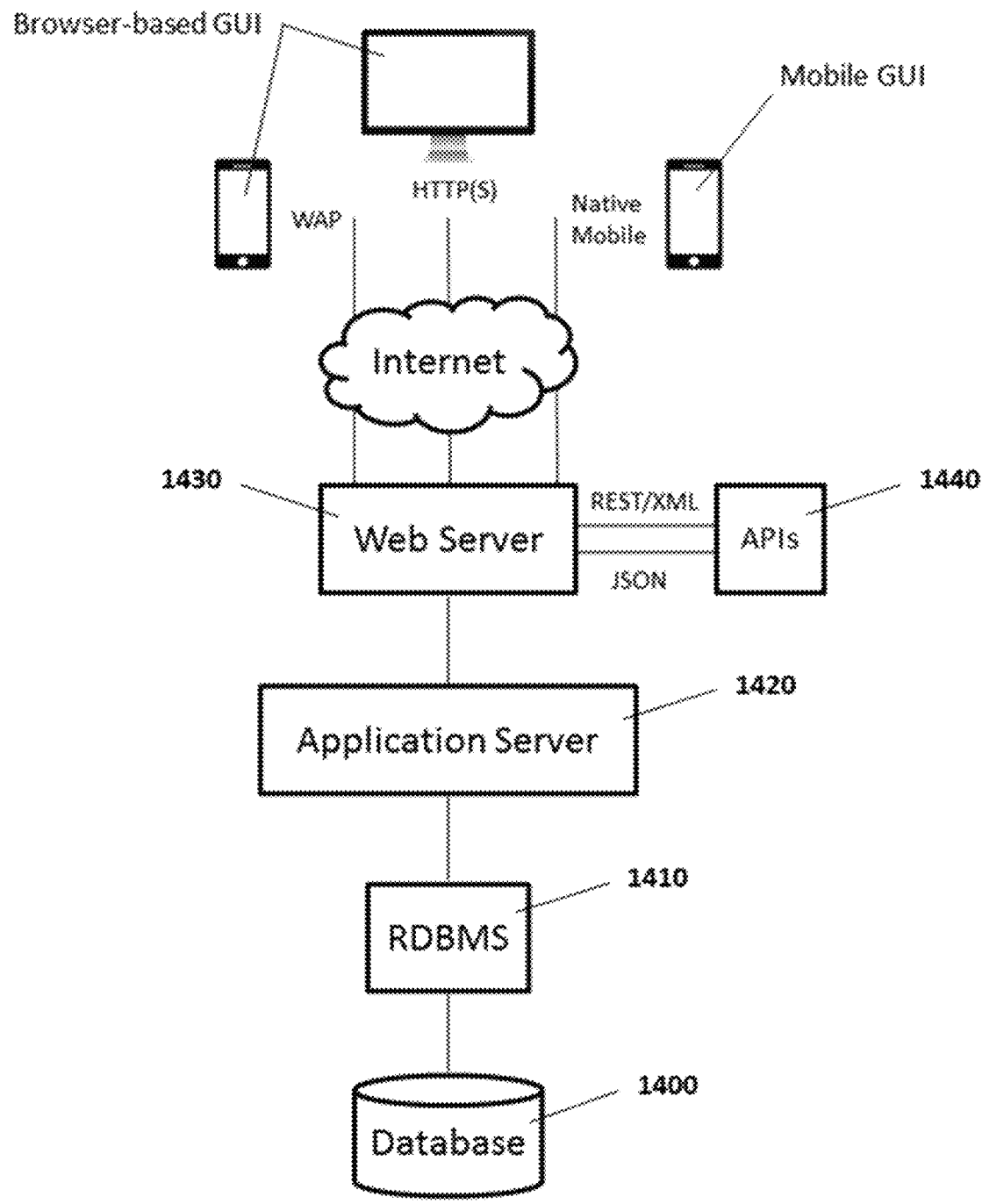
FIG. 14 shows a non-limiting schematic diagram of a web/mobile application provision system; in this case, a system providing browser-based and/or native mobile user interfaces.

Referring to FIG. 14, in a particular embodiment, an application provision system comprises one or more databases 1400 accessed by a relational database management system (RDBMS) 1410. Suitable RDBMSs include Firebird, MySQL, PostgreSQL, SQLite, Oracle Database, Microsoft SQL Server, IBM DB2, IBM Informix, SAP Sybase, SAP Sybase, Teradata, and the like. In this embodiment, the application provision system further comprises one or more application severs 1420 (such as Java servers, .NET servers, PHP servers, and the like) and one or more web servers 1430 (such as Apache, IIS, GWS and the like). The web server(s) optionally expose one or more web services via app application programming interfaces (APIs) 1440. Via a network, such as the Internet, the system provides browser-based and/or mobile native user interfaces.

Figure 15:
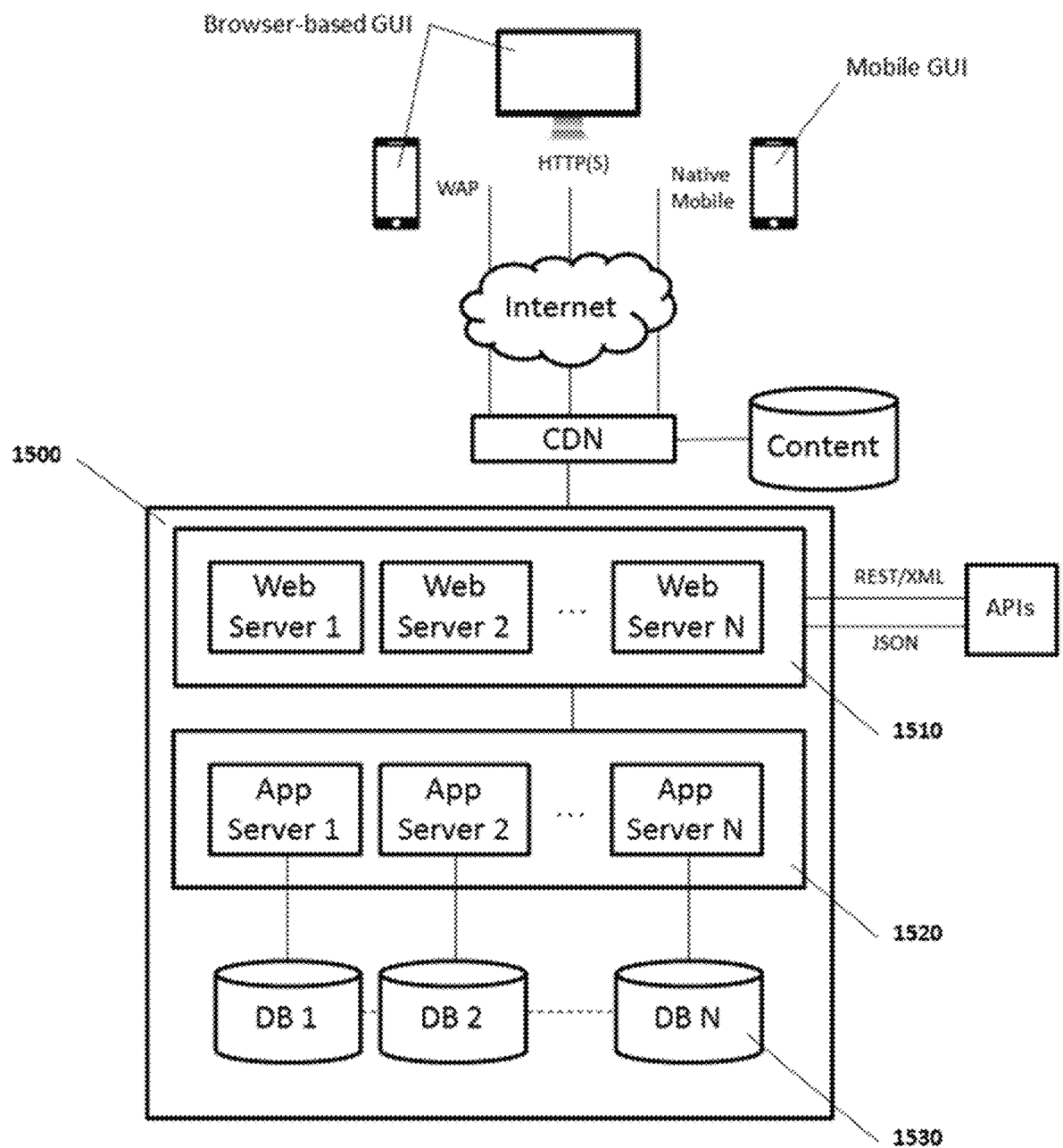
FIG. 15 shows a non-limiting schematic diagram of a cloud-based web/mobile application provision system; in this case, a system comprising an elastically load balanced, auto-scaling web server and application server resources as well synchronously replicated databases.

Referring to FIG. 15, in a particular embodiment, an application provision system alternatively has a distributed, cloud-based architecture 1500 and comprises elastically load balanced, auto-scaling web server resources 1510 and application server resources 1520 as well synchronously replicated databases 1530.

Software Modules

In some embodiments, the platforms, systems and methods disclosed herein include software, server, and/or database modules, or use of the same. In some embodiments, the local computing device for the subject, the local computing device for the medical professional or the remote computing device herein includes a software module or use of the same. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

Databases

In some embodiments, the systems and methods disclosed herein include one or more databases, or use of the same. In some embodiments, the local computing device for the subject, the local computing device for the medical professional or the remote computing device herein includes a database or use of the same. In view of the disclosure provided herein, those of skill in the art will recognize that many databases are suitable for storage and retrieval of measurement data, analysis of measurement data and treatment regimen generated by the remote computing device, analysis of measurement data and treatment regimen generated by the local computing device for the medical professional. In various embodiments, suitable databases include, by way of non-limiting examples, relational databases, non-relational databases, object oriented databases, object databases, entity-relationship model databases, associative databases, and XML databases. Further non-limiting examples include SQL, PostgreSQL, MySQL, Oracle, DB2, and Sybase. In some embodiments, a database is internet-based. In further embodiments, a database is web-based. In still further embodiments, a database is cloud computing-based. In other embodiments, a database is based on one or more local computer storage devices.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

Unless otherwise defined, all technical terms used herein have the same meaning as commonly understood by one of ordinary skill in the art to which this disclosure belongs. As used in this specification and the appended claims, the singular forms "a," "an," and "the" include plural references unless the context clearly dictates otherwise. Any reference to "or" herein is intended to encompass "and/or" unless otherwise stated. As used in this specification and the claims, unless otherwise stated, the term "about," and "approximately" refers to variations of less than or equal to +/−1%, +/−2%, +/−3%, +/−4%, +/−5%, +/−6%, +/−7%, +/−8%, +/−9%, +/−10%, +/−11%, +/−12%, +/−14%, +/−15%, or +/−20% of the numerical value depending on the embodiment. As a non-limiting example, about 100 meters represents a range of 95 meters to 105 meters (which is +/−5% of 100 meters), 90 meters to 110 meters (which is +/−10% of 100 meters), or 85 meters to 115 meters (which is +/−15% of 100 meters) depending on the embodiments.

While preferred embodiments of the present disclosure have been shown and described herein, it will be obvious to those skilled in the art that such embodiments are provided by way of example only. Numerous variations, changes, and substitutions will now occur to those skilled in the art without departing from the scope of the present disclosure. It should be understood that various alternatives to the embodiments of the present disclosure described herein may be employed in practicing the present disclosure. It is intended that the following claims define the scope of invention and that methods and structures within the scope of these claims and their equivalents be covered thereby.

What is claimed is:

1. A method for monitoring a joint of a subject over a course of therapy, the method comprising:
   providing a plurality of adherent sensors adhered to skin adjacent the joint, each adherent sensor comprising an adherent surface, a mechanical sensing element for sensing one or more mechanical parameters of the joint, and a transmitter;
   measuring measurement data with at least one adherent sensor of the plurality of adherent sensors;
   transmitting the measurement data from the at least one adherent sensor to a local computing device, the local computing device being in communication with a remote computing device and being configured to transmit the measurement data thereto;

receiving the measurement data with the remote computing device;

providing analysis of the measurement data to the local computing device from the remote computing device; and providing the analysis to the subject with the local computing device, wherein at least one adherent sensor of the plurality of adherent sensors comprises a replaceable enclosure and a sensor assembly removable from the enclosure, the replaceable enclosure comprising the adherent surface and the sensor assembly comprising the mechanical sensing element and the transmitter, wherein the replaceable enclosure is replaced while the sensor assembly is continually used over the course of therapy, wherein the replaceable enclosure comprises a pouch in which the sensor assembly is inserted, wherein the adherent surface comprises an adhesive, and wherein the sensor assembly of each adherent sensor comprises at least one power source selected from a group consisting of: a power supply, a battery, and an energy harvesting element.

2. The method of claim 1, wherein the at least one adherent sensor of the plurality of adherent sensors comprises an activation element coupled to the power source and the at least one adherent sensor is activated by at least partially removing the activation element.

3. The method of claim 1, wherein the at least one adherent sensor of the plurality of adherent sensors is configured to be worn by the subject for at least six to eight weeks and the replaceable enclosure is configured to be replaced after one to two weeks of use while the sensor assembly is continually used after replacement of the replaceable enclosure.

4. The method of claim 1, wherein the mechanical sensing element comprises one or more of a strain sensor, a force sensor, a flex sensor, a pressure sensor, an accelerometer, a magnetometer, a gyroscope, a potentiometer, a barometer, a piezoelectric sensor, a pressurized tube sensor, a coiled conductor sensor, or a magnetic sensor.

5. The method of claim 1, wherein measuring the measurement data comprises measuring one or more of an elevation of the adherent sensor, an orientation of the adherent sensor relative to gravity, an orientation of the adherent sensor relative to a paired adherent sensor, an orientation of the adherent sensor relative to the joint, motion of the adherent sensor, motion of the joint, motion of tissue adjacent the joint, a deformation of the adherent sensor, a pitch of the adherent sensor, a roll of the adherent sensor, a yaw of the adherent sensor, stress on the adherent sensor, or strain on the adherent sensor with the mechanical sensing element of the at least one adherent sensor.

6. The method of claim 1, wherein the at least one adherent sensor of the plurality of adherent sensors further comprises one or more of a temperature sensor, a humidity sensor, an electrical impedance sensor, an acoustic impedance sensor, an electromyography (EMG) sensor, an oxygen sensor, a pH sensor, an optical sensor, an ultrasound sensor, a glucose sensor, or a biomarker sensor.

7. The method of claim 1, wherein measuring the measurement data comprises measuring one or more of an elevation of the at least one adherent sensor, an elevation of the at least one adherent sensor relative to a paired adherent sensor of the plurality of adherent sensors, a temperature of the skin adjacent the joint, motion of the at least one adherent sensor, a pitch of the at least one adherent sensor, a roll of the at least one adherent sensor, a yaw of the at least one adherent sensor, motion of the at least one adherent sensor relative to the paired adherent sensor, an orientation of the at least one adherent sensor, an orientation of the at least one adherent sensor relative to the paired adherent sensor, an orientation of the at least one adherent sensor relative to the joint, a stretching or shrinkage of the at least one adherent sensor, an oxygenation of tissue adjacent the joint, a humidity of the tissue adjacent the joint, a muscle activity of the joint, an electrical impedance of the tissue adjacent the joint, an acoustic impedance of the tissue adjacent the joint, or one or more biomarkers.

8. The method of claim 1, wherein the local computing device comprises one or more of a personal computer, a laptop computer, a tablet computer, a smart phone, a smart television (TV), a gaming console, a digital media player, a smart speaker, a smart home, a smart watch, a virtual reality/augmented reality (VR/AR) goggle or glasses, or a wearable computing device.

9. The method of claim 1, wherein the remote computing device comprises one or more of a server, a workstation, a personal computer, a laptop computer, a tablet computer, a smart phone, a smart television (TV), a gaming console, a digital media player, a smart speaker, a smart home, a smart watch, a virtual reality/augmented reality (VR/AR) goggle or glasses, or a wearable computing device.

10. The method of claim 1, wherein the plurality of adherent sensors are configured to communicate with one another wirelessly.

11. The method of claim 10, wherein the plurality of adherent sensors are configured to communicate with one another wirelessly with a wireless data transfer protocol comprising one or more of Near Field Communication (NFC), wireless universal serial bus (USB), ultra-wide-band, ultraband, Wi-Fi, Bluetooth, Bluetooth LE, ZigBee, WiMax, Thread, Long Range kLoRa), Low-Power Wide-Area (LPWA), an Internet of Things (IoT) networking protocol, a radio-wave based protocol, a microwave based protocol, an infrared based protocol, or a sound-wave based protocol.

12. The method of claim 1, wherein the plurality of adherent sensors are configured to communicate with the local computing device wirelessly.

13. The method of claim 12, wherein the plurality of adherent sensors are configured to communicate with one another wirelessly with a wireless data transfer protocol comprising one or more of Near Field Communication (NFC), wireless wireless universal serial bus (USB, ultra-wide-band, ultraband, Wi-Fi, Bluetooth, Bluetooth LE, Zig-Bee, WiMax, Thread, Long Range ILoRa), Low-Power Wide-Area (LPWA), an Internet of Things IoTinetworking protocol, a radio-wave based protocol, a microwave based protocol, an infrared based protocol, or a sound-wave based protocol.

14. The method of claim 1, further comprising determining one or more of a range of motion of the joint, a range of flexion of the joint, a range of extension of the joint, a range of rotation of the joint, a motion pattern of the joint, a gait of the subject, a position of the joint, an orientation of the joint, a placement of the plurality of adherent sensors relative to the joint, a compliance of the subject to a joint cooling or heating protocol, a compliance of the subject to a movement protocol, a compliance of the subject for muscle activation/inactivation swelling of the joint, inflammation of the joint, edema of the joint, impact on the joint, or a physical therapy progress of the subject based on the received measurement data with one or more of the local computing device or the remote computing device.

15. The method of claim 1, further comprising determining one or more of placements and orientations of the plurality of adherent sensors relative to the joint and determine one or more of a range of motion of the joint, a range of flexion of the joint, a range of extension of the joint, a range of rotation of the joint, a motion pattern of the joint, a gait of the subject, a position of the joint, or an orientation of the joint based on the determined placement and orientations of the plurality of adherent sensors relative to the joint with one or more of the local computing device or the remote computing device.

16. The method of claim 1, further comprising automatically generating the analysis of the measurement data with the remote computing device.

17. The method of claim 16, wherein providing analysis of the measurement data to the local computing device from the remote computing device comprises providing a medical professional computing device access to the remote computing device to access one or more of the measurement data or at least a first portion of the analysis, receiving at least a second portion of the analysis from the medical professional computing device as provided by the medical professional with the remote computing device, compiling at least the first and second portions of the analysis, and transmitting the compiled analysis to the local computing device.

18. The method of claim 17, wherein the medical professional computing device comprises one or more of a personal computer, a laptop computer, a tablet computer, a smart phone, a smart TV, a gaming console, a digital media player, a smart speaker, a smart home, a smart watch, or a wearable computing device.

19. The method of claim 1, wherein the local computing device provides the analysis to the subject via one or more of an audio user interface or a video user interface of the local computing device.

20. The method of claim 1, further comprising providing one or more of a reminder, an alarm, a tip, an insight, or an instruction to the subject with the local computing device.

21. The method of claim 1, further comprising receiving input from the subject with the local computing device and transmitting the received input to the remote computing device with the local computing device.

22. The method of claim 21, wherein the input comprises one or more of a self-diagnosis parameter, a progress of a physical therapy protocol, a compliance to a physical therapy protocol, or a biometric parameter of the subject.

23. The method of claim 1, wherein the joint comprises one or more of an ankle, a knee, a hip, a spine, a neck, a shoulder, an elbow, or a wrist.

* * * * *